United States Patent
Zemlok et al.

(10) Patent No.: US 11,607,284 B2
(45) Date of Patent: Mar. 21, 2023

(54) ROBOTIC SURGICAL ASSEMBLIES

(71) Applicant: Covidien LP, Mansfield, MA (US)

(72) Inventors: Mike Zemlok, Prospect, CT (US); Jaimeen Kapadia, Cambridge, MA (US); Mark MacLeod, Southbury, CT (US); Chi Min Seow, New Haven, CT (US); Josiah Rosmarin, Sebring, FL (US)

(73) Assignee: COVIDIEN LP, Mansfield, MA (US)

( * ) Notice: Subject to any disclaimer, the term of this patent is extended or adjusted under 35 U.S.C. 154(b) by 1156 days.

(21) Appl. No.: 16/303,968

(22) PCT Filed: May 23, 2017

(86) PCT No.: PCT/US2017/033935
§ 371 (c)(1),
(2) Date: Nov. 21, 2018

(87) PCT Pub. No.: WO2017/205333
PCT Pub. Date: Nov. 30, 2017

(65) Prior Publication Data
US 2020/0337792 A1    Oct. 29, 2020

Related U.S. Application Data

(60) Provisional application No. 62/341,774, filed on May 26, 2016, provisional application No. 62/341,804, (Continued)

(51) Int. Cl.
*A61B 34/00* (2016.01)
*A61B 34/37* (2016.01)
(Continued)

(52) U.S. Cl.
CPC .............. *A61B 34/71* (2016.02); *A61B 18/12* (2013.01); *A61B 34/35* (2016.02); *A61B 34/37* (2016.02);
(Continued)

(58) Field of Classification Search
CPC . B25J 15/04; B25J 9/1045; B25J 9/104; B25J 9/4035; B25J 9/0021;
(Continued)

(56) References Cited

U.S. PATENT DOCUMENTS 2,777,340 A    1/1957    Hettwer et al.
2,957,353 A    10/1960   Babacz
(Continued)

FOREIGN PATENT DOCUMENTS

CA    2451558 A1    1/2003
CN    1547454 A     11/2004
(Continued)

OTHER PUBLICATIONS

Australian Office Action dated Feb. 17, 2021, issued in related AU Appln. No. 2017272072, 4 pages.
(Continued)

*Primary Examiner* — Jocelin C Tanner
(74) *Attorney, Agent, or Firm* — Carter, DeLuca & Farrell, LLP

(57) ABSTRACT

A surgical instrument holder includes a carriage, a housing, and a drive assembly. The carriage is configured for engagement to a surgical robotic arm and for supporting an instrument drive unit. The housing extends from the carriage and defines a channel. The drive assembly includes a pulley, a belt, and an annular member. The pulley is rotatably disposed within the housing and in operable engagement with a motor of the carriage such that actuation of the motor rotates the pulley. The belt is rotatably disposed within the
(Continued)

housing and in operable engagement with the pulley such that rotation of the pulley effects rotation of the belt. The annular member is disposed within the channel of the housing and configured for non-rotatable receipt of an instrument drive unit. The annular member is in operable engagement with the belt such that rotation of the belt effects rotation of the annular member.

21 Claims, 65 Drawing Sheets

Related U.S. Application Data filed on May 26, 2016, provisional application No. 62/341,701, filed on May 26, 2016, provisional application No. 62/341,720, filed on May 26, 2016, provisional application No. 62/341,714, filed on May 26, 2016, provisional application No. 62/341,761, filed on May 26, 2016, provisional application No. 62/341,748, filed on May 26, 2016.

(51) Int. Cl.

| | | |
|---|---|---|
| *A61B 46/23* | (2016.01) | |
| *B25J 9/00* | (2006.01) | |
| *B25J 9/10* | (2006.01) | |
| *A61B 46/10* | (2016.01) | |
| *A61B 90/50* | (2016.01) | |
| *A61B 34/35* | (2016.01) | |
| *A61B 18/12* | (2006.01) | |
| *B25J 5/00* | (2006.01) | |
| *B25J 9/04* | (2006.01) | |
| *B25J 15/00* | (2006.01) | |
| *B25J 15/04* | (2006.01) | |
| *B25J 19/00* | (2006.01) | |
| *A61B 34/30* | (2016.01) | |
| *A61B 17/00* | (2006.01) | |
| *A61B 18/00* | (2006.01) | |

(52) U.S. Cl.
CPC .............. *A61B 34/70* (2016.02); *A61B 34/74* (2016.02); *A61B 34/76* (2016.02); *A61B 46/10* (2016.02); *A61B 46/23* (2016.02); *A61B 90/50* (2016.02); *B25J 5/00* (2013.01); *B25J 9/0021* (2013.01); *B25J 9/0024* (2013.01); *B25J 9/04* (2013.01); *B25J 9/104* (2013.01); *B25J 9/108* (2013.01); *B25J 9/1035* (2013.01); *B25J 9/1045* (2013.01); *B25J 15/0019* (2013.01); *B25J 15/0408* (2013.01); *B25J 19/0041* (2013.01); *A61B 34/30* (2016.02); *A61B 2017/0084* (2013.01); *A61B 2017/00411* (2013.01); *A61B 2017/00477* (2013.01); *A61B 2017/00836* (2013.01); *A61B 2017/00853* (2013.01); *A61B 2017/00929* (2013.01); *A61B 2018/00178* (2013.01); *A61B 2034/301* (2016.02); *A61B 2034/302* (2016.02); *A61B 2034/715* (2016.02)

(58) Field of Classification Search
CPC ........ A61B 2034/715; A61B 2034/302; A61B 2034/301; A61B 2018/00178; A61B 2017/00929; A61B 2017/00853; A61B 2017/0084; A61B 2017/00836; A61B 2017/00477; A61B 2017/00411; A61B 90/98; A61B 90/90; A61B 90/50; A61B 46/23; A61B 46/10; A61B 46/00; A61B 34/76; A61B 34/74; A61B 34/71; A61B 34/70; A61B 34/37; A61B 34/35; A61B 34/30; A61B 18/12

See application file for complete search history.

(56) References Cited

U.S. PATENT DOCUMENTS

| | | |
|---|---|---|
| 3,111,328 A | 11/1963 | Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,683,772 A | 8/1987 | Colimitra |
| 4,705,038 A | 11/1987 | Sjostrom et al. |
| 4,722,685 A | 2/1988 | de Estrada et al. |
| 4,823,807 A | 4/1989 | Russell et al. |
| 4,862,759 A | 9/1989 | Trevelyan et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,353 A * | 9/1997 | Drake ............... B25J 9/104 901/17 |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Mesi et al. |
| 5,782,396 A | 7/1998 | Mastri et al. |
| 5,782,397 A | 7/1998 | Koukline |
| 5,784,542 A | 7/1998 | Ohm et al. |
| 5,792,573 A | 8/1998 | Pitzen et al. |
| 5,797,536 A | 8/1998 | Smith et al. |
| 5,797,900 A | 8/1998 | Madhani et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |

(56) References Cited

U.S. PATENT DOCUMENTS

| | | |
|---|---|---|
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,451,027 B1 * | 9/2002 | Cooper .............. A61B 1/00149 901/19 |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,554,844 B2 | 4/2003 | Lee et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Drtiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,422,592 B2 | 9/2008 | Morley et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Drtiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,824,401 B2 | 11/2010 | Manzo et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 3,025,199 A1 | 9/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,035,487 B2 | 10/2011 | Malackowski |
| 8,052,024 B2 | 11/2011 | Viola et al. |
| 8,074,859 B2 | 12/2011 | Kostrzewski |
| 8,092,451 B2 | 1/2012 | Schechter et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |

(56) References Cited

U.S. PATENT DOCUMENTS

| | | | |
|---|---|---|---|
| 8,186,587 B2 | 5/2012 | Zmood et al. |
| 8,220,367 B2 | 7/2012 | Hsu |
| 8,235,273 B2 | 8/2012 | Olson et al. |
| 8,237,388 B2 | 8/2012 | Jinno et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,465,476 B2 | 6/2013 | Rogers et al. |
| 8,505,802 B2 | 8/2013 | Viola et al. |
| 8,506,555 B2 * | 8/2013 | Ruiz Morales | A61B 34/76 901/14 |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,192 B2 | 1/2014 | Farascioni et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,925,786 B2 | 1/2015 | Holsten et al. |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 8,998,799 B2 | 4/2015 | Orban, III et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,937,626 B2 | 4/2018 | Rockrohr |
| 10,179,413 B2 | 1/2019 | Rockrohr |
| 2001/0031975 A1 | 10/2001 | Whitman et al. |
| 2002/0032451 A1 | 3/2002 | Tierney et al. |
| 2002/0040217 A1 | 4/2002 | Jinno |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0079884 A1 | 4/2006 | Manzo et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0161138 A1 | 7/2006 | Orban, III |
| 2006/0235436 A1 | 10/2006 | Anderson et al. |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0039256 A1 | 2/2008 | Jinno et al. |
| 2008/0058801 A1 | 3/2008 | Taylor et al. |
| 2008/0103491 A1 | 5/2008 | Omori et al. |
| 2008/0109012 A1 | 5/2008 | Falco et al. |
| 2008/0110958 A1 | 5/2008 | McKenna et al. |
| 2008/0119870 A1 | 5/2008 | Williams |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0245175 A1 | 10/2008 | Jinno et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |

(56) References Cited

U.S. PATENT DOCUMENTS

| | | |
|---|---|---|
| 2009/0299141 A1 | 12/2009 | Downey et al. |
| 2010/0016852 A1 | 1/2010 | Manzo et al. |
| 2010/0016853 A1 | 1/2010 | Burbank |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2010/0228264 A1 | 9/2010 | Robinson et al. |
| 2010/0292708 A1 | 11/2010 | Madhani et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0010616 A1 | 1/2012 | Huang et al. |
| 2012/0074199 A1 | 3/2012 | Olson et al. |
| 2012/0080475 A1 | 4/2012 | Smith et al. |
| 2012/0080485 A1 | 4/2012 | Woodard, Jr. et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0116416 A1 | 5/2012 | Neff et al. |
| 2012/0143002 A1 | 6/2012 | Aranyi et al. |
| 2012/0168485 A1 | 7/2012 | Marczyk et al. |
| 2012/0172924 A1 | 7/2012 | Allen, IV |
| 2012/0199630 A1 | 8/2012 | Shelton, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0020376 A1 | 1/2013 | Shelton, IV et al. |
| 2013/0032629 A1 | 2/2013 | Viola |
| 2013/0093149 A1 | 4/2013 | Saur et al. |
| 2013/0131695 A1 | 5/2013 | Scarfogliero et al. |
| 2013/0158542 A1 | 6/2013 | Manzo et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0325095 A1 | 12/2013 | Ollivier |
| 2013/0331858 A1 | 12/2013 | Devengenzo et al. |
| 2013/0334281 A1 | 12/2013 | Williams |
| 2014/0001236 A1 | 1/2014 | Shelton, IV et al. |
| 2014/0005640 A1 | 1/2014 | Shelton, IV et al. |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0166023 A1 | 6/2014 | Kishi |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0309666 A1 | 10/2014 | Shelton, IV |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2014/0378761 A1 | 12/2014 | Zorn et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0150635 A1 | 6/2015 | Kilroy |
| 2015/0150636 A1 | 6/2015 | Hagn et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2018/0168748 A1 | 6/2018 | Kapadia |

FOREIGN PATENT DOCUMENTS

| | | |
|---|---|---|
| CN | 1957854 A | 5/2007 |
| CN | 101340848 A | 1/2009 |
| CN | 101340852 A | 1/2009 |
| CN | 101495046 A | 7/2009 |
| CN | 102028548 A | 4/2011 |
| CN | 102058437 A | 5/2011 |
| CN | 102247182 A | 11/2011 |
| CN | 103732174 A | 4/2014 |
| CN | 104394793 A | 3/2015 |
| CN | 104619280 A | 5/2015 |
| CN | 105611894 A | 5/2016 |
| DE | 102008053842 A1 | 5/2010 |
| EP | 0443576 A1 | 8/1991 |
| EP | 0705571 A1 | 4/1996 |
| EP | 1563793 A1 | 8/2005 |
| EP | 1769754 A1 | 4/2007 |
| EP | 2316345 A1 | 5/2011 |
| EP | 2668910 A2 | 12/2013 |
| EP | 3416582 A1 | 12/2018 |
| ES | 2333509 A1 | 2/2010 |
| JP | 2005125075 A | 5/2005 |
| JP | 2008528197 A | 7/2008 |
| JP | 2009520573 A | 5/2009 |
| JP | 2009226028 A | 10/2009 |
| JP | 2009297326 A | 12/2009 |
| JP | 2012120884 A | 6/2012 |
| JP | 2013034833 A | 2/2013 |
| JP | 2013103137 A | 5/2013 |
| JP | 2014512888 A | 5/2014 |
| JP | 2015134203 A | 7/2015 |
| JP | 2016513993 A | 5/2016 |

(56) References Cited

FOREIGN PATENT DOCUMENTS

| KR | 20120022521 | A  | 3/2012 |
|----|-------------|----|--------|
| WO | 2011016640  | A2 | 2/2011 |
| WO | 2011037394  | A3 | 8/2011 |
| WO | 2011108840  | A2 | 9/2011 |
| WO | 2012/040984 | A1 | 4/2012 |
| WO | 2015023834  | A1 | 2/2015 |
| WO | 2015142785  | A1 | 9/2015 |
| WO | 2015142793  | A1 | 9/2015 |
| WO | 2016042923  | A1 | 3/2016 |
| WO | 2016043845  | A1 | 3/2016 |

OTHER PUBLICATIONS

Australian Office Action dated Feb. 17, 2021, issued in related AU Appln. No. 2017272081, 4 pages.
Australian Office Action dated Feb. 17, 2021, issued in related AU Appln. No. 2017272085, 4 pages.
Australian Office Action dated Feb. 25, 2021, issued in related Australian Appln. No. 2017272075, 4 pages.
Extended European Search Report dated Feb. 6, 2020 corresponding to counterpart Patent Application EP 17803392.4.
Extended European Search Report corresponding to International Application No. EP 14 18 4882.0 dated May 12, 2015.
Canadian Office Action corresponding to International Application No. CA 2640399 dated May 7, 2015.
Japanese Office Action corresponding to International Application No. JP 2011-197365 dated Mar. 23, 2015.
Japanese Office Action corresponding to International Application No. JP 2011-084092 dated May 20, 2015.
Japanese Office Action corresponding to International Application No. JP 2014-148482 dated Jun. 2, 2015.
Extended European Search Report corresponding to International Application No. EP 14 18 9358.6 dated Jul. 8, 2015.
Extended European Search Report corresponding to International Application No. EP 14 19 6148.2 dated Apr. 23, 2015.
Partial European Search Report corresponding to International Application No. EP 14 19 6704.2 dated May 11, 2015.
Australian Office Action corresponding to International Application No. AU 2010241367 dated Aug. 20, 2015.
Partial European Search Report corresponding to International Application No. EP 14 19 9783.3 dated Sep. 3, 2015.
Extended European Search Report corresponding to International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
Chinese First Office Action corresponding to counterpart Chinese Patent Appln. No. CN 2014800674869 dated Jan. 24, 2018.
Extended European Search Report corresponding to counterpart EP Application No. 14 87 0110.5 dated Mar. 20, 2018.
Chinese Second Office Action corresponding to counterpart Patent Appln. CN 2014800674869 dated Aug. 1, 2018.
International Search Report for (PCT/US2014/061863) dated Jan. 21, 2015; 4 pages.
Japanese Office Action dated Feb. 26, 2021, issued in related Japanese Appln. No. 2018561604, 4 pages.
Japanese Office Action dated Feb. 26, 2021, issued in related Japanese Appln. No. 2018561587, 7 pages.
Chinese Office Action (with English translation), dated Nov. 4, 2019, corresponding to counterpart Chinese Application No. 201780002103.3; 20 total pages.
European Search Repod, dated Dec. 20, 2019, corresponding to counterpart European Application No. 17803383.3; 11 pages.
European Search Report, dated Dec. 20, 2019, corresponding to counterpart European Application No. 17803381.7; 11 pages.
European Communication dated Jan. 24, 2020, corresponding to counterpart European Application No. 17803384.1; 1 page.
Chinese Office Action dated Dec. 18, 2020, issued in related CN Appln. No. 201780028942, 16 pages.
Chinese Office Action dated Dec. 23, 2020, issued in related CN Appln. No. 201780031985, 3 pages.
European Search Report dated Jan. 3, 2020, corresponding to counterpart European Application No. 17803397.3; 7 pages.
Japanese Office Action dated Mar. 3, 2021, issued in related Japanese Appln. No. 2018-561601, 3 pages.
Japanese Office Action dated Mar. 5, 2021, issued in related Japanese Appln. No. 2018-561600, 6 pages.
Japanese Office Action dated Feb. 26, 2021, issued in corresponding Japanese Appln No. 2018-561605, 4 pages.
Indian Office Action dated Jun. 13, 2021, issued in related Indian Appln. No. 201817039273, 5 pages.
Indian Office Action dated Jun. 18, 2021, issued in related Indian Appln. No. 201817039126, 6 pages.
Indian Office Action dated Jun. 16, 2021, issued in related Indian Appln. No. 201817039464, 7 pages.
Australian Office Action dated Nov. 17, 2021, issued in corresponding Australian appln. No. 2017269261, 3 pages.
Indian Office Action dated Jun. 7, 2021, issued in related Indian Application No. 201817039453, 7 pages.

(56) References Cited

OTHER PUBLICATIONS

Indian Office Action dated May 31, 2021, issued in related Indian Application No. 201817039272, 6 pages.
Indian Office Action dated May 27, 2021, issued in related Indian Application No. 201817039460, 5 pages.
Chinese Office Action dated Dec. 1, 2020, issued in corresponding CN Appln. No. 201780028941, 10 pages.
Chinese Office Action dated Dec. 3, 2020, issued in corresponding CN Appln. No. 201780038873, 14 pages.
Chinese Office Action dated Dec. 1, 2020, issued in related Chinese Appln. No. 201780028940, 11 pages.
Chinese Office Action (with English translation), dated May 8, 2020, corresponding to counterpart Chinese Application No. 201780002103.3; 21 total pages.
European Communication dated Jan. 30, 2020 and European Communication dated Jan. 13, 2020 with Supplementary European Search Report, corresponding to counterpart European Application No. 17803386.6; 4 total pages.
Australian Office Action dated Sep. 30, 2021, issued in corresponding AU Application No. 2017269261, 3 pages.
Canadian Office Action dated Sep. 14, 2021, issued in corresponding Canadian Application No. 3,022,145, 8 pages.
Japanese Office Action dated Feb. 26, 2021, issued in related JP Appln. No. 2018-561598, 5 pages.
Chinese Office Action dated Apr. 6, 2021, issued in related Chinese Appln. No. 201780031985, 9 pages.
Australian Office Action dated Apr. 30, 2021, issued in corresponding Australian Appln. No. 2017269262, 3 pages.
Australian Office Action dated May 4, 2021, issued in related AU Appln. No. 2017269271, 3 pages.
Chinese Office Action dated Dec. 24, 2020, issued in corresponding Chinese Appln. No. 201780030972, 10 pages.
Japanese Office Action dated Apr. 6, 2021, issued in related JP Appln. No. 2018-561599, 5 pages.

* cited by examiner

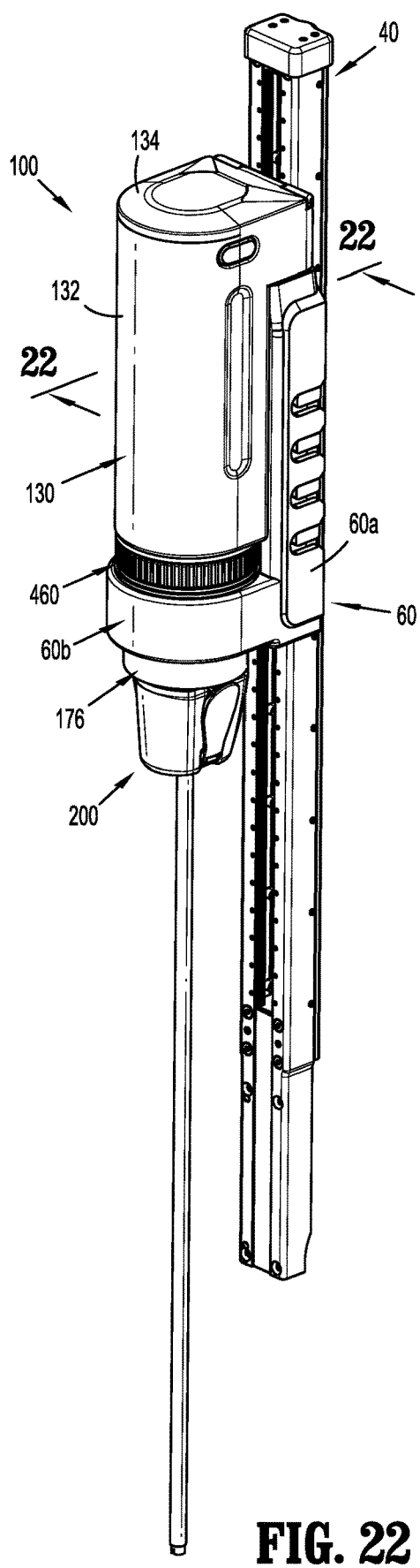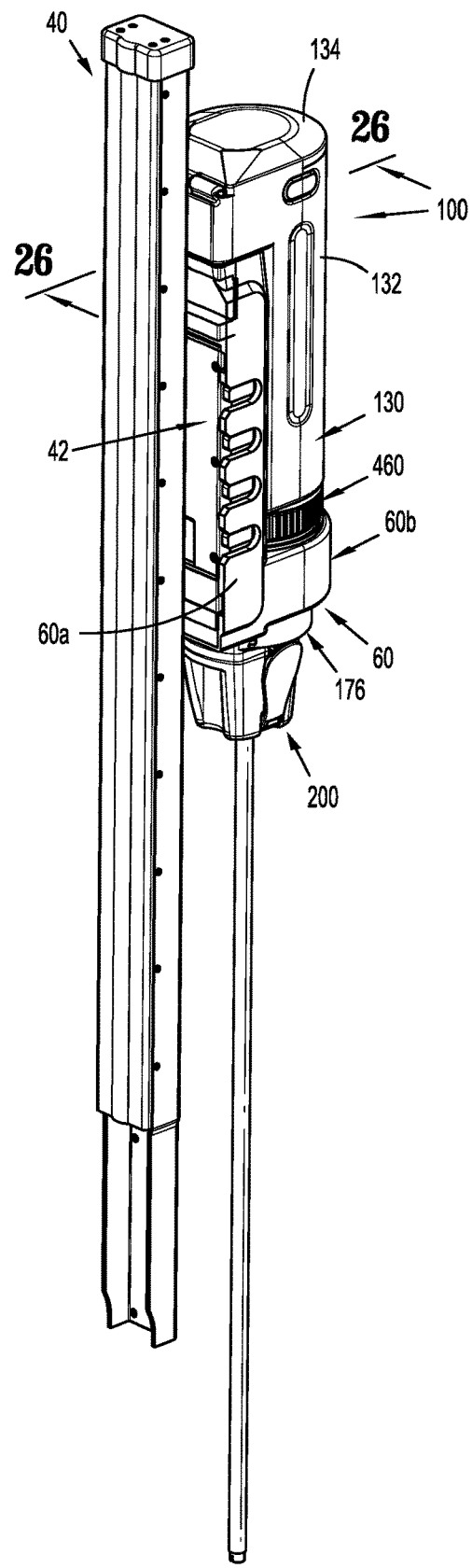
FIG. 22  FIG. 23

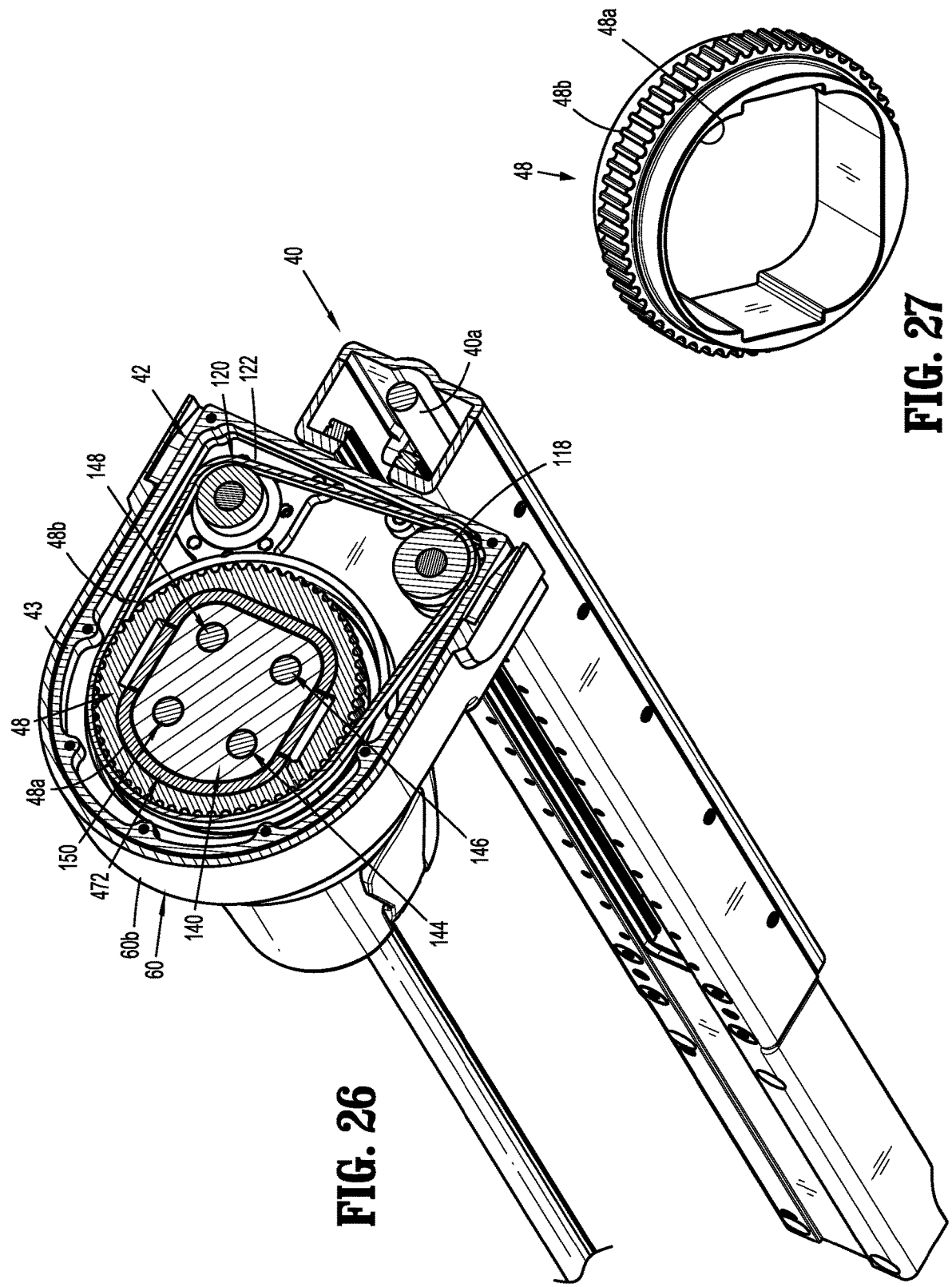

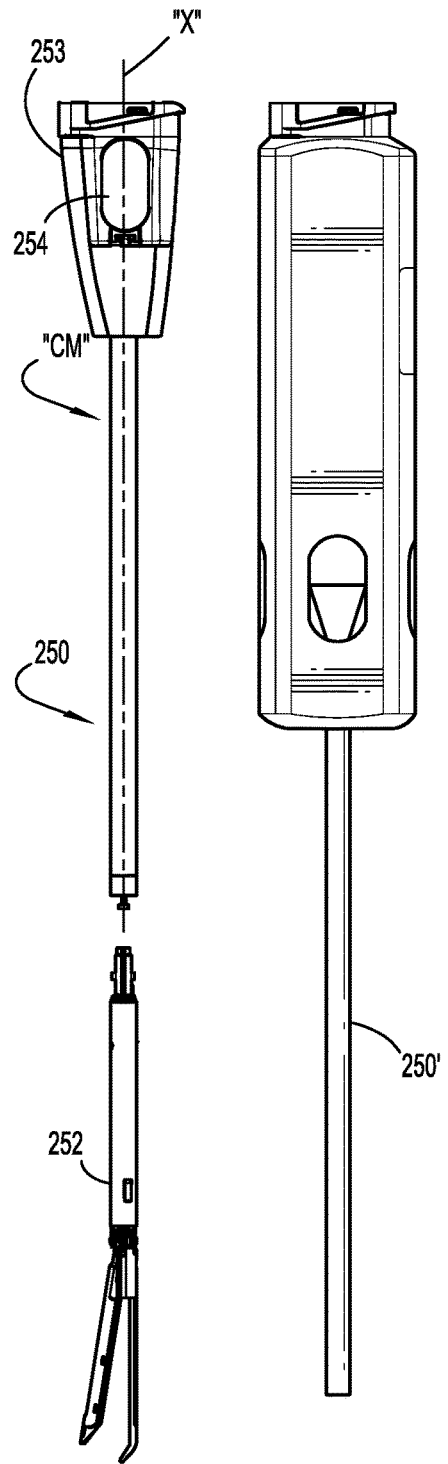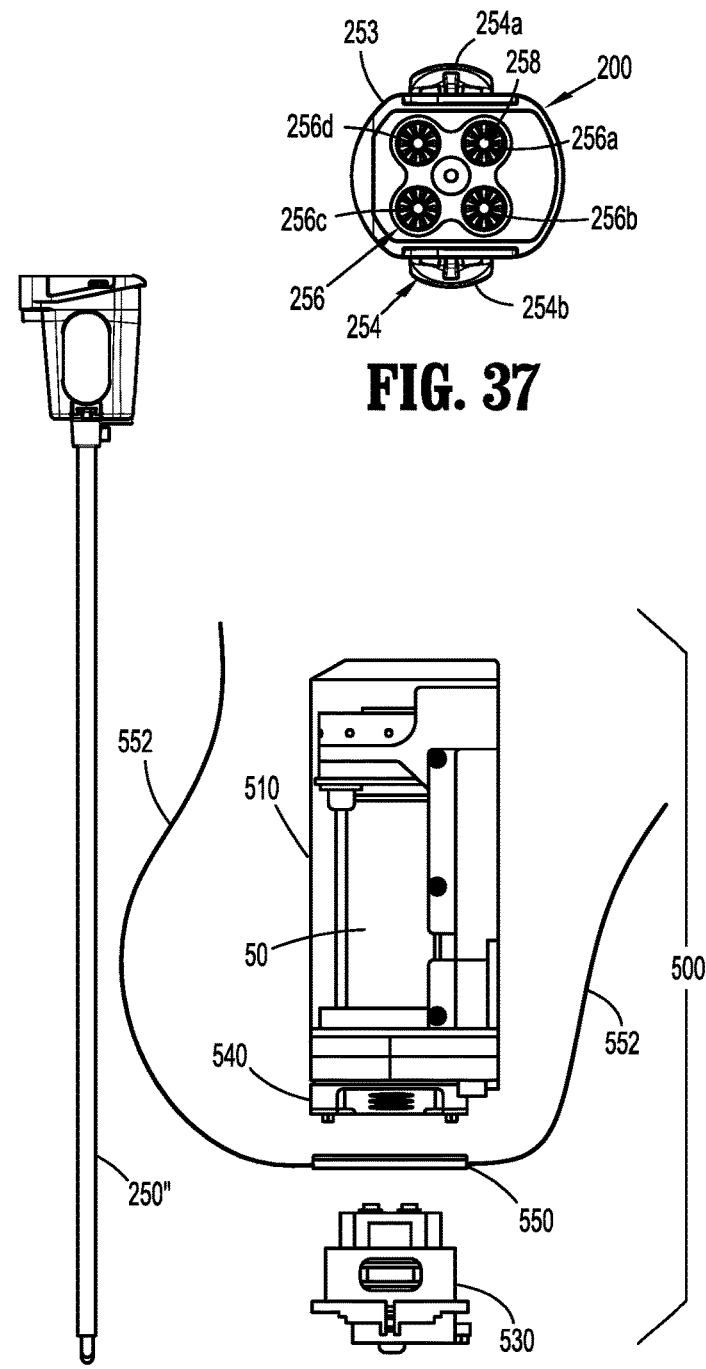
FIG. 37
FIG. 36

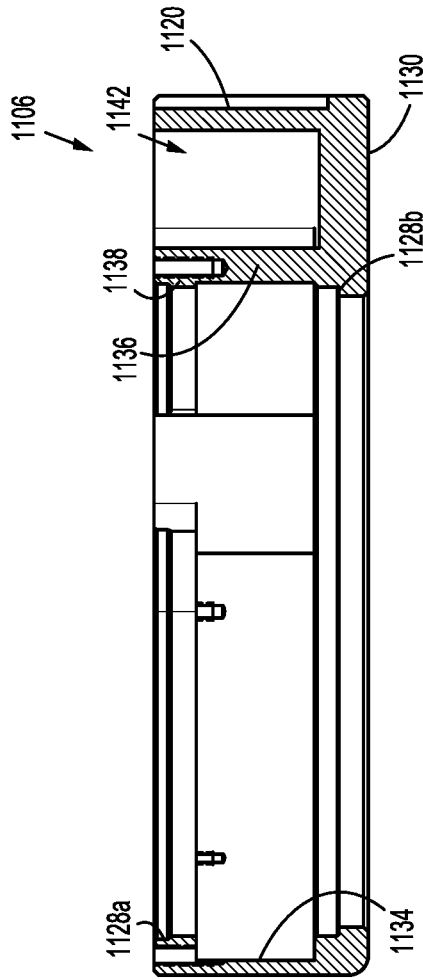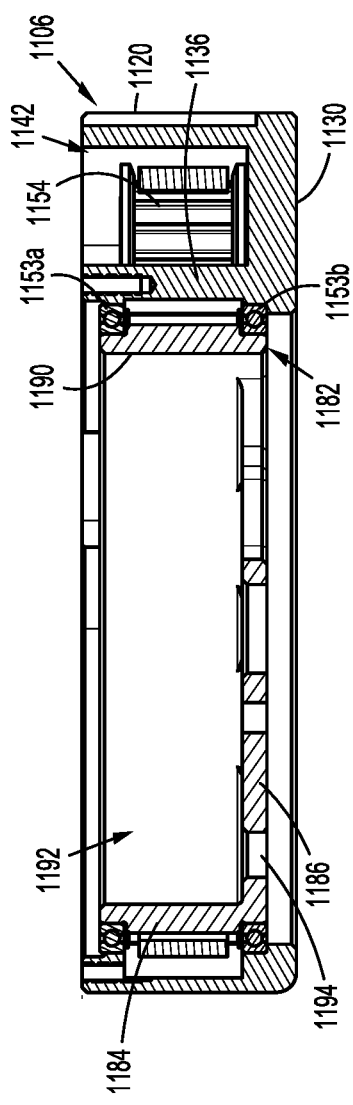
FIG. 64A
FIG. 64B

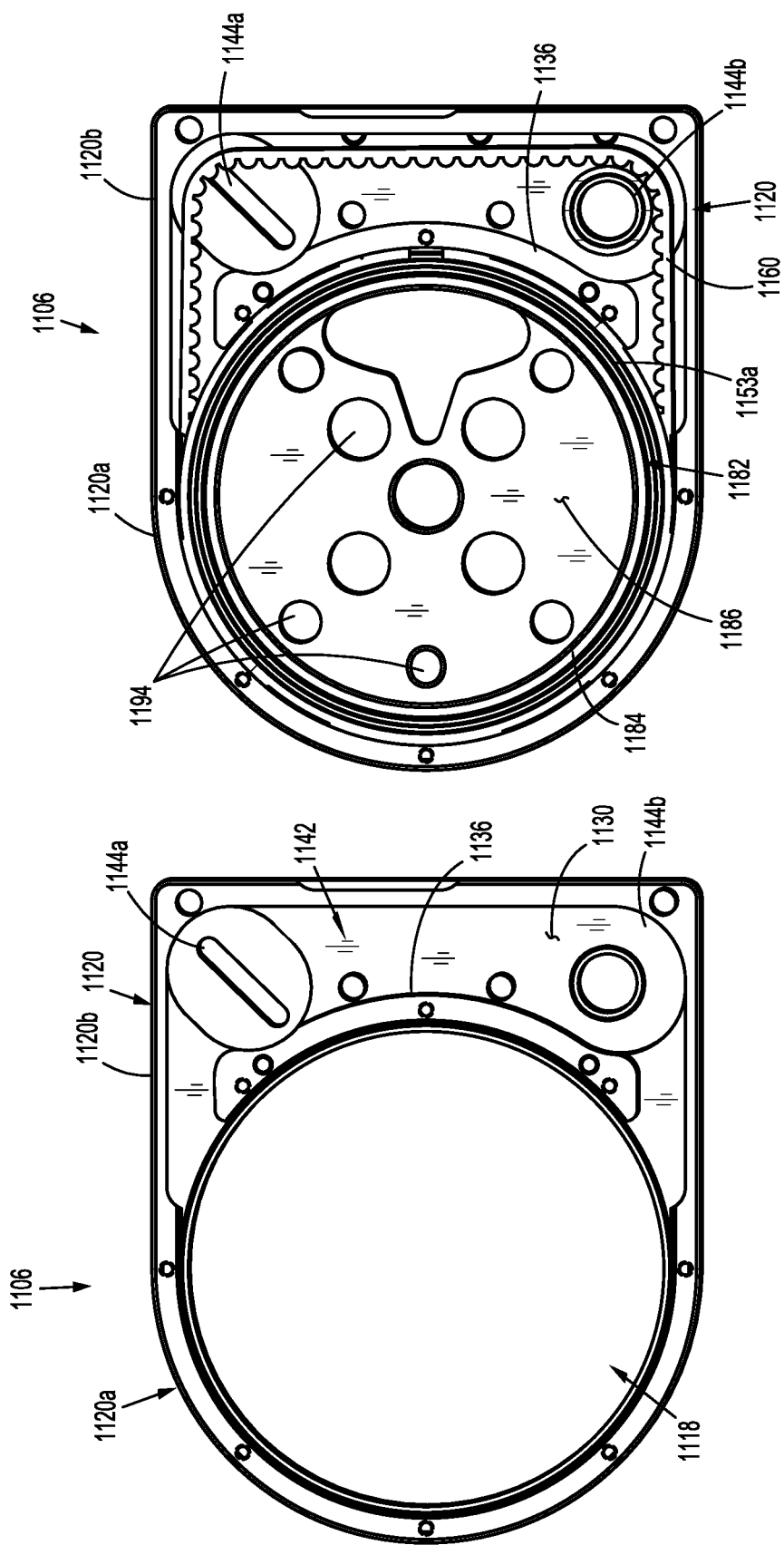

ROBOTIC SURGICAL ASSEMBLIES

CROSS REFERENCE TO RELATED APPLICATIONS

This application is a U.S. National Stage Application filed under 35 U.S.C. § 371(a) of International Patent Application Serial No. PCT/US2017/033935, filed May 23, 2017, which claims the benefit of and priority to each of U.S. Provisional Application No. 62/341,714, filed May 26, 2016; U.S. Provisional Application No. 62/341,701, filed May 26, 2016; U.S. Provisional Application No. 62/341,720, filed May 26, 2016, U.S. Provisional Application No. 62/341,748; filed May 26, 2016, U.S. Provisional Application No. 62/341,761, filed May 26, 2016; U.S. Provisional Application No. 62/341,774, filed May 26, 2016; and U.S. Provisional Application No. 62/341,804, filed May 26, 2016, the entire contents of each of which are incorporated by reference herein.

This application also claims the benefit of and priority to each of U.S. National Stage Application filed under 35 U.S.C. § 371(a) of International Patent Application Serial No. PCT/US2017/033899, filed May 23, 2017; U.S. National Stage Application filed under 35 U.S.C. § 371(a) of International Patent Application Serial No. PCT/US2017/033903, filed May 23, 2017; U.S. National Stage Application filed under 35 U.S.C. § 371(a) of International Patent Application Serial No. PCT/US2017/033905, filed May 23, 2017; U.S. National Stage Application filed under 35 U.S.C. § 371(a) of International Patent Application Serial No. PCT/US2017/033902, filed May 23, 2017; U.S. National Stage Application filed under 35 U.S.C. § 371(a) of International Patent Application Serial No. PCT/US2017/033931, filed May 23, 2017; U.S. National Stage Application filed under 35 U.S.C. § 371(a) of International Patent Application Serial No. PCT/US2017/033926, filed May 23, 2017, the entire disclosures of which are incorporated by reference herein.

BACKGROUND

Robotic surgical systems have been used in minimally invasive medical procedures. Some robotic surgical systems include a console supporting a surgical robotic arm and a surgical instrument, having at least one end effector (e.g., forceps or a grasping tool), mounted to the robotic arm. The robotic arm provides mechanical power to the surgical instrument for its operation and movement. Each robotic arm may include an instrument drive unit that is operatively connected to the surgical instrument.

Manually-operated surgical instruments often include a handle assembly for actuating the functions of the surgical instrument. However, when using a robotic surgical system, no handle assembly is typically present to actuate the functions of the end effector. Accordingly, to use each unique surgical instrument with a robotic surgical system, an instrument drive unit is used to interface with the selected surgical instrument to drive operations of the surgical instrument. In robotic surgical systems, a robot arm may be used to hold the surgical instrument. In some robotic surgical systems, the entire length of the elongate shaft of the surgical instrument must pass through a holder or other feature of the robot arm, thereby making the removal or exchange of the surgical instrument cumbersome.

Accordingly, a need exists for a robotic surgical system that enables more efficient and expeditious removal or exchange of a surgical instrument.

A need further exists for a robotic surgical system in which the axis of rotation of a surgical instrument takes place in a robotic arm of the robotic surgical assembly as compared to within the surgical instrument itself. In this manner, the construction and assembly of the surgical instrument is simplified and more cost efficient.

Further, a need exists for a robotic surgical system having improved and increased usability. For example, a need also exists for a robotic surgical system that is manually controllable in emergency situations.

SUMMARY

In accordance with an aspect of the present disclosure, a robotic surgical system is provided. The robotic surgical system includes a robotic arm, a carriage coupled to the robotic arm, a drive belt, and a motor supported by the carriage. The carriage rotatably supports an instrument rotation pulley and a motor axis pulley. The drive belt is coupled to the instrument rotation pulley and the motor axis pulley. The motor is supported by the carriage and includes a coupling that is driven by the motor upon an actuation of the motor. The coupling is engaged with the motor axis pulley such that rotation of the motor axis pulley rotates the drive belt to rotate the instrument rotation pulley.

In some embodiments, the robotic surgical system may include a surgical instrument configured to couple to the carriage. The surgical instrument may operably couple to the instrument rotation pulley such that rotation of the instrument rotation pulley rotates the surgical instrument.

The robotic surgical system may comprise a sterile barrier housing including a drive transfer assembly configured to couple to the surgical instrument. The sterile barrier housing may include a cap. The cap may be removable to expose an internal cavity defined within the sterile barrier housing. The cavity may be configured to selectively receive a motor pack therein.

In certain embodiments, the robotic surgical system may further comprise a sterile barrier collar assembly configured to couple to the drive transfer assembly. The sterile barrier collar assembly may be configured to support the surgical instrument while the surgical instrument is coupled to the drive transfer assembly. The drive transfer assembly and the sterile barrier collar assembly may rotate together in response to rotation of the instrument rotation pulley so that the surgical instrument rotates along a longitudinal axis thereof while coupled to the sterile barrier collar assembly.

The robotic surgical system may further comprise a motor pack supported in the sterile barrier housing. The motor pack may rotate with the drive transfer assembly relative to the sterile barrier housing.

In some embodiments, the robotic surgical system may further include a tension pulley operably coupled to the drive belt.

According to another aspect of the present disclosure, a robotic surgical system includes a surgical instrument, an instrument drive unit, and a carriage supporting the instrument drive unit and the surgical instrument while the surgical instrument is coupled to the instrument drive unit. The surgical instrument defines a longitudinal axis between proximal and distal ends thereof. The instrument drive unit may be configured to transmit rotational forces to the surgical instrument while the surgical instrument is coupled to the instrument drive unit.

The carriage includes an instrument rotation pulley, a motor axis pulley, a drive belt coupled to the instrument rotation pulley and the motor axis pulley, and a coupling.

The coupling may be engaged with the motor axis pulley such that rotation of the coupling rotates the drive belt around the instrument rotation pulley and the motor axis pulley to rotate the surgical instrument about the longitudinal axis of the surgical instrument.

In some embodiments, the robotic surgical system may include a robotic arm supporting a rail. The carriage may be movably mounted to the rail of the robotic arm. The carriage may include a rear panel coupled to the rail and a coupling flange extending from the rear panel. The coupling flange may rotatably support the instrument rotation pulley.

In certain embodiments, the instrument drive unit may include a sterile barrier housing having a drive transfer assembly extending therefrom. The drive transfer assembly may be configured to couple to the surgical instrument. The sterile barrier housing may include a cap. The cap may be removable to expose an internal cavity defined within the sterile barrier housing. The cavity may be configured to selectively receive a motor pack therein.

The robotic surgical system may include a sterile barrier collar assembly configured to couple to the drive transfer assembly. The sterile barrier collar assembly may be configured to support the surgical instrument while the surgical instrument is coupled to the drive transfer assembly. The drive transfer assembly and the sterile barrier collar assembly may rotate together in response to rotation of the instrument rotation pulley so that the surgical instrument rotates while coupled to the sterile barrier collar.

In some embodiments, the robotic surgical system may include a motor pack supported in the sterile barrier housing. The motor pack may be configured to engage the drive transfer assembly so that the drive transfer assembly provides a sterile interface between the motor pack and the surgical instrument. The motor pack may rotate with the drive transfer assembly relative to the sterile barrier housing.

In some embodiments, the carriage further includes a tension pulley operably coupled to the drive belt.

In accordance with yet another aspect of the present disclosure, the robotic surgical assembly includes a carriage, a shell mounted to the carriage, a sterile barrier housing removably connectable to the shell, and a motor pack. The sterile barrier housing may define a cavity therein and may have a drive transfer assembly extending distally therefrom. The motor pack may be selectively receivable within the cavity of the sterile barrier housing and may be configured to interface with the drive transfer assembly of the sterile barrier housing while received within the cavity of the sterile barrier housing to transmit rotational forces from the motor pack to the drive transfer assembly. The drive transfer assembly is configured to transmit rotational forces to a surgical instrument coupled to the drive transfer assembly.

The robotic surgical assembly may include a lock ring rotatably supported on the sterile barrier housing. The drive transfer assembly may be rotatable relative to sterile barrier housing, and the lock ring may support a tactile feedback ring that may be configured to couple to the drive transfer assembly to provide tactile feedback as to an angular orientation of the drive transfer assembly.

In some embodiments, the sterile barrier housing may include a cover pivotally coupled thereto to selectively close the motor pack within the cavity.

In certain embodiments, the robotic surgical assembly may further include a sterile drape coupled to the shell. The sterile drape may be positionable to establish a sterile barrier.

The robotic surgical assembly may further include a robotic arm having a rail supported on the robotic arm. The carriage may be axially movable along the rail. The carriage may include a coupling flange that rotatably supports an instrument rotation pulley. The instrument rotation pulley may define an opening therethrough. The opening may define a key-way for non-rotational receipt of the drive transfer assembly.

In some embodiments, a sterile barrier collar assembly may be configured to couple to the drive transfer assembly. The sterile barrier collar assembly may be configured to support the surgical instrument while the surgical instrument is coupled to the drive transfer assembly. The drive transfer assembly and the sterile barrier collar assembly may rotate together in response to rotation of the instrument rotation pulley so that the surgical instrument rotates along a longitudinal axis thereof while coupled to the sterile barrier collar assembly.

In certain embodiments, the motor pack may rotate with the drive transfer assembly relative to the sterile barrier housing.

According to one aspect of the present disclosure, a robotic surgical system includes a robotic arm, a surgical instrument, and a robotic surgical assembly coupled to the robotic arm and configured to support the surgical instrument.

The robotic surgical assembly includes a carriage, a shell mounted to the carriage, a sterile barrier housing connectable to the shell, and a motor pack supported by the sterile barrier housing. The sterile barrier housing may have a drive transfer assembly extending distally therefrom. The motor pack may be configured to interface with the drive transfer assembly of the sterile barrier housing to transmit rotational forces from the motor pack to the drive transfer assembly. The drive transfer assembly may be configured to transmit rotational forces to the surgical instrument.

In certain embodiments, a lock ring may be rotatably supported on the sterile barrier housing. The drive transfer assembly may be rotatable relative to sterile barrier housing, and the lock ring may supports a tactile feedback ring that is configured to couple to the drive transfer assembly to provide tactile feedback as to an angular orientation of the drive transfer assembly.

In some embodiments, the sterile barrier housing may include a cover pivotally coupled thereto to selectively close the motor pack within the cavity.

The robotic surgical system may include a sterile drape coupled to the shell. The sterile drape may be positionable to establish a sterile barrier.

In certain embodiments, the robotic arm may include a rail and the carriage may be axially movable along the rail. The carriage may include a coupling flange that rotatably supports an instrument rotation pulley that defines an opening therethrough. The opening may define a key-way for non-rotational receipt of the drive transfer assembly.

The robotic surgical system may include a sterile barrier collar assembly configured to couple to the drive transfer assembly. The sterile barrier collar assembly may be configured to support the surgical instrument while the surgical instrument is coupled to the drive transfer assembly. The drive transfer assembly and the sterile barrier collar assembly may rotate together in response to rotation of the instrument rotation pulley so that the surgical instrument rotates along a longitudinal axis thereof while coupled to the sterile barrier collar assembly. The motor pack may rotate with the drive transfer assembly relative to the sterile barrier housing.

In accordance with still another aspect of the present disclosure, a sterile interface module for coupling an electromechanical robotic surgical instrument to a robotic surgical assembly is provided. The surgical instruments including an end effector and may be configured to be actuated by the robotic surgical assembly.

The sterile interface module includes a body member configured to selectively couple the surgical instrument to the robotic surgical assembly. The body member may be formed of a dielectric material. The sterile interface module may include a drive assembly supported within the body member and may be configured to transmit rotational forces from the robotic surgical assembly to the surgical instrument to actuate the surgical instrument to enable the surgical instrument to perform a function.

In some embodiments, the body member may support an electrical connector that electrically communicates information between the robotic surgical assembly and the surgical instrument. The body member may support an electrosurgical connecting member that is configured to transmit electrosurgical energy from the robotic surgical assembly to the surgical instrument. The electrosurgical connecting member may be electrically isolated from the electrical connector.

In certain embodiments, the drive assembly may include a drive coupler and a transfer shaft extending from the drive coupler. The drive coupler may be engagable with the robotic surgical assembly and the transfer shaft may be engagable with the surgical instrument. The drive coupler and the transfer assembly may be robotically movable to operate the end effector of the surgical instrument.

The sterile interface module may include a rotatable collar supported on the body member. The sterile interface module may include a ring coupler secured to the rotatable collar, a drive coupler secured to the transfer shaft of the drive assembly, and an idler coupler supported between the drive coupler and the ring coupler. The ring coupler may be selectively engagable with the idler coupler as the rotatable collar rotates between a first position and a second position.

In some embodiments, the sterile interface module may further include a floating plate coupled to the body member. The floating plate may be movable relative to the body member to facilitate selective connection of the surgical instrument to the body member. The floating plate may be spring biased.

In one aspect of the present disclosure, a robotic surgical system includes an electromechanical robotic surgical instrument, a robotic surgical assembly, and a sterile interface module. The sterile interface module has a body member formed of a dielectric material. The body member may be configured to selectively couple the surgical instrument to the robotic surgical assembly to maintain sterility between the robotic surgical assembly and the surgical instrument. The body member may support a drive assembly configured to transmit rotational forces from the robotic surgical assembly to the surgical instrument to actuate the surgical instrument.

The body member of the sterile interface module may support an electrical connector that electrically communicates information between the robotic surgical assembly and the surgical instrument while the body member is coupled to the robotic surgical assembly and the surgical instrument. The body member of the sterile interface module may support an electrosurgical connecting member that is configured to transmit electrosurgical energy from the robotic surgical assembly to the surgical instrument. The electrosurgical connecting member may be electrically isolated from the electrical connector.

In certain embodiments, the surgical instrument may include an end effector. The drive assembly of the sterile interface module may include a drive coupler and a transfer shaft extending from the drive coupler. The drive coupler may be engagable with the robotic surgical assembly and the transfer shaft may be engagable with the surgical instrument. The drive coupler and the transfer assembly may be robotically movable to operate the end effector of the surgical instrument.

In some embodiments, the sterile interface module may include a rotatable collar supported on the body member of the sterile interface module. The sterile interface module may include a ring coupler secured to the rotatable collar, a drive coupler secured to the transfer shaft of the drive assembly, and an idler coupler supported between the drive coupler and the ring coupler. The ring coupler may be selectively engagable with the idler coupler as the rotatable collar rotates between a first position and a second position. The ring coupler may rotate between the first and second positions to selectively disengage the drive coupler from the robotic surgical assembly. Rotation of the rotatable collar may result axial movement of the rotatable collar and selective engagement between the idler coupler and the rotatable collar.

In certain embodiments, the sterile interface module may include a floating plate coupled to the body member of the sterile interface module. The floating plate may be movable relative to the body member of the sterile interface module to facilitate selective connection of the surgical instrument to the body member of the sterile interface module. The floating plate of the sterile interface module may be spring biased.

According to still another aspect of the present disclosure, a surgical instrument for coupling to a robotic surgical assembly configured to transfer rotational forces to the surgical instrument is provided. The surgical instrument includes an elongated shaft, an end effector coupled to a distal end of the elongated shaft, and a drive assembly operatively coupled to the end effector. The drive assembly includes one or more cables connected to the end effector, wherein movement of the one or more cables actuates a movement of the end effector. The one or more cables may be coated with parylene.

In some embodiments, the one or more cables may be movable in response to rotational forces transmitted from the robotic surgical assembly.

In certain embodiments, the drive assembly may include a drive screw supporting a drive nut. The drive nut may be axially movable along the drive screw as the drive screw rotates to move the one or more cables.

The surgical instrument may further include a second drive assembly operatively coupled to the end effector. The second drive assembly may include a second drive screw supporting a second drive nut that is axially movable along the second drive screw as the second drive screw rotates. The first and second drive nuts may be configured to move in axially opposite directions as the first and second drive screws rotate.

In some embodiments, the drive assembly includes a biasing member that maintains the one or more cables in tension.

In certain embodiments, the surgical instrument includes a housing supported on a proximal end of the elongated shaft. The housing may be configured to couple to the robotic surgical assembly. The housing may include a side surface supporting a ramped camming surface. The ramped camming surface may be configured to enable the housing to be transversely coupled to the robotic surgical assembly. The housing may support one or more electrical connectors configured to electrically couple to the robotic surgical assembly so that the surgical instrument can electrically communicate with the robotic surgical assembly.

In some embodiments, the one or more cables may be formed of tungsten.

According to one aspect of the present disclosure, a robotic surgical instrument includes a housing configured to couple to a robotic surgical assembly, an elongated shaft extending distally from the housing, an end effector extending distally from the elongated shaft, and a drive assembly supported in the housing. The drive assembly includes a cable connected to the end effector. The cable is movable to actuate the end effector. The cable may be coated with an autoclavable material.

The cable may be movable in response to rotational forces transmitted from the robotic surgical assembly while the housing is coupled to the robotic surgical assembly.

In some embodiments, the drive assembly includes a drive screw supporting a drive nut. The drive nut may be axially movable along the drive screw as the drive screw rotates to move the cable. The robotic surgical instrument may include a second drive assembly operatively coupled to the end effector. The second drive assembly may include a second drive screw supporting a second drive nut that is axially movable along the second drive screw as the second drive screw rotates. The first and second drive nuts may be configured to move in axially opposite directions as the first and second drive screws rotate.

In certain embodiments, the drive assembly includes a biasing member that maintains the cable in tension.

In some embodiments, the autoclavable material may include parylene. The cable may be formed of tungsten.

In certain embodiments, the housing includes a side surface supporting a ramped camming surface. The ramped camming surface may be configured to enable the housing to be transversely coupled to the robotic surgical assembly. The housing may support one or more electrical connectors configured to electrically couple to the robotic surgical assembly so that the surgical instrument can electrically communicate with the robotic surgical assembly.

According to another aspect of the present disclosure, the robotic surgical system includes a surgical instrument and a robotic surgical assembly. The robotic surgical assembly defines an instrument opening and includes a floating plate and a drive assembly. The floating plate may be movable between an extended position and a compressed position. The surgical instrument may be laterally receivable in the instrument opening of the robotic surgical assembly while the floating plate is disposed in the compressed position. The floating plate may be movable to the extended position to couple the surgical instrument to the robotic surgical assembly while the surgical instrument is received in the instrument opening of the robotic surgical assembly.

In some embodiments, the floating plate includes one or more tabs extending therefrom. The one or more tabs may be configured to engage the surgical instrument to move the floating plate from the extended position to the compressed position.

In certain embodiments, the drive assembly may include one or more couplers extending into the instrument opening while the floating plate is disposed in the extended position. The floating plate may move the one or more couplers out of the instrument opening as the floating plate moves from the extended position to the compressed position. The surgical instrument may include one or more couplers that complement the one or more couplers of the robotic surgical assembly. The one or more couplers of the robotic surgical assembly may be configured to engage the one or more couplers of the surgical instrument while the floating plate is in the extended position and the surgical instrument is coupled to the robotic surgical assembly.

In some embodiments, the floating plate may be spring biased toward the extended position.

In certain embodiments, the robotic surgical assembly may include a semi-annular coupling cuff that defines the instrument opening. The semi-annular coupling cuff may include a U-shaped body. The coupling cuff may include a ramped surface formed on an inner surface of the coupling cuff. The ramped surface may be configured to engage a complementary surface formed on an outer surface of the surgical instrument so that the ramped surface of the coupling cuff supports the surgical instrument in the instrument opening.

In some embodiments, the surgical instrument may include a housing and one or more paddles pivotally connected to the housing. The one or more paddles may be engagable with the floating plate to move the floating plate to the compressed position so that the surgical instrument can slide laterally through the instrument opening.

According to still another aspect of the present disclosure, a robotic surgical assembly for selective engagement to a surgical instrument is provided. The robotic surgical assembly includes a drive assembly configured to transmit rotational forces to the surgical instrument, a semi-annular coupling cuff defining an instrument opening, and floating plate. The floating plate may be movable between an extended position and a compressed position. The coupling cuff may be configured to receive the surgical instrument laterally through the instrument opening while the floating plate is in the compressed position. The floating plate may be movable from the compressed position to the extended position to couple the drive assembly to the surgical instrument.

The floating plate may include one or more tabs extending therefrom. The one or more tabs may be configured to engage the surgical instrument to move the floating plate from the extended position to the compressed position.

In some embodiments, the drive assembly may include one or more couplers extending into the instrument opening while the floating plate is disposed in the extended position. The floating plate may move the one or more couplers out of the instrument opening as the floating plate moves from the extended position to the compressed position. The one or more couplers may be configured to engage the surgical instrument while the floating plate is in the extended position. The floating plate may be spring biased toward the extended position.

In some embodiments, the coupling cuff may include a U-shaped body. The coupling cuff may include a ramped surface formed on an inner surface of the coupling cuff. The ramped surface may be configured to engage a complementary surface formed on an outer surface of the surgical instrument so that the ramped surface of the coupling cuff supports the surgical instrument in the instrument opening.

In certain embodiments, the drive assembly may be coupled to a robotically controlled motor assembly that actuates the drive assembly.

According to one aspect of the present disclosure, a sterile interface module for coupling a surgical instrument to a robotic surgical assembly is provided. The surgical instrument includes an end effector.

The sterile interface module includes a body member configured to selectively couple the surgical instrument to the robotic surgical assembly. The sterile interface module further includes a first drive transfer assembly supported by the body member. The first drive transfer assembly includes a drive coupler and a transfer shaft extending from the drive coupler. The drive coupler may be engagable with the robotic surgical assembly and the transfer shaft may be engagable with the surgical instrument. The drive coupler and the transfer assembly may be robotically movable to operate the end effector of the surgical instrument.

A rotatable collar is supported on the body member and is operably associated with the first drive transfer assembly. The rotatable collar may be manually movable relative to the body member to manually operate the end effector of the surgical instrument. The rotatable collar may move axially relative to the body member as the rotatable collar rotates around the body member.

The sterile interface module may further include a ring coupler secured to the rotatable collar. A drive coupler may be secured to the transfer shaft of the first drive transfer assembly, and an idler coupler may be supported between the drive coupler and the ring coupler. The ring coupler may be engaged with the idler coupler while the rotatable collar is in a first position and spaced from the idler coupler while the rotatable collar is in a second position. The ring coupler may rotate the idler coupler as the rotatable collar rotates around the body member. Rotation of the idler coupler may rotate the drive coupler to rotate the transfer shaft.

In some embodiments, a second drive transfer assembly is configured to operate the end effector of the surgical instrument in conjunction with the first drive transfer assembly. The first drive transfer assembly may be rotatable independent of the second drive transfer assembly as the rotatable collar moves relative to the body member. The second drive transfer assembly may be configured to remain stationary as the rotatable collar rotates relative to the body member.

In certain embodiments, a floating plate may be coupled to the body member and a spring may be positioned between the drive coupler and the transfer shaft. The floating plate may be movable with the transfer shaft relative to the body member in a proximal direction to facilitate selective removal of the surgical instrument from the body member. The spring may be configured to bias the floating plate in a distal direction.

According to another aspect of the present disclosure, a robotic surgical system includes a surgical instrument including an end effector, a robotic surgical assembly, and a sterile interface module positionable between the robotic surgical assembly and the surgical instrument to couple the surgical instrument to the robotic surgical assembly.

According to yet another aspect of the present disclosure, a method for manually operating an end effector of a surgical instrument coupled to a robotic surgical assembly is provided. The method includes rotating a rotatable collar of a sterile interface module to axially move a ring coupler relative to an idler coupler, selectively engaging the ring coupler with the idler coupler, rotating the idler coupler with the ring coupler to manually rotate a first drive transfer assembly while the ring coupler is engaged with the idler coupler; and manipulating the end effector of the surgical instrument in response to the manual rotation of the first drive transfer assembly.

The method may include axially spacing the ring coupler from the idler coupler to disengage the ring coupler from the idler coupler. The method may include manually rotating the first drive transfer assembly independent of a second drive transfer assembly.

In accordance with an aspect of the present disclosure, a surgical instrument holder is provided. The surgical instrument holder includes a carriage, a housing, and a drive assembly. The carriage is configured for engagement to a surgical robotic arm and for supporting an instrument drive unit. The carriage includes a motor. The housing extends from the carriage and defines a channel. The drive assembly includes a pulley, a belt, and an annular member. The pulley is rotatably disposed within the housing and in operable engagement with the motor such that actuation of the motor rotates the pulley. The belt is rotatably disposed within the housing and in operable engagement with the pulley such that rotation of the pulley effects rotation of the belt. The annular member is disposed within the channel of the housing and configured for non-rotatable receipt of an instrument drive unit. The annular member is in operable engagement with the belt such that rotation of the belt effects rotation of the annular member.

In some embodiments, the belt may be a closed loop and include teeth extending from an inner surface of the belt. The annular member may have teeth extending from an outer surface thereof and in operable engagement with the teeth of the belt. The annular member may include a ring and an annular base plate disposed within the ring. The ring may have the teeth of the annular member extending therefrom. The annular base plate may define one or more holes. The ring and the annular base plate may cooperatively define a cavity configured to receive an instrument drive unit.

It is contemplated that the carriage may further include a rotatable drive shaft extending from the motor, and a shaft coupling non-rotatably connected to the drive shaft. The drive assembly may further include a driven shaft having a proximal end non-rotatably connected to the shaft coupling, and a distal end non-rotatably connected to the pulley such that rotation of the drive shaft of the carriage effects rotation of the shaft coupling and in turn rotation of the pulley of the drive assembly. Each of the motor of the carriage, the drive shaft of the carriage, and the driven shaft of the drive assembly may define a longitudinal axis in line with one another.

It is envisioned that the carriage may further include a printed circuit board in electrical communication with the motor to control an operation of the motor.

In some aspects of the present disclosure, the belt may be pliable and configured to travel along an oblong semicircular shape defined by the housing.

In some embodiments, the housing may include a sidewall defining an enclosure therein, and a base disposed within the enclosure and connected to the sidewall. The base may define the channel of the housing and an arcuate bottom ledge. The housing may further include an arcuate wall extending upwardly from the base. The drive assembly may further include a first bearing and a second bearing. The first bearing may be disposed in the housing and in engagement with the annular member. The second bearing may be disposed on the arcuate bottom ledge of the housing and in engagement with the annular member. The first and second bearings facilitate rotation of the annular member relative to the housing.

It is contemplated that the drive assembly may further include a second pulley rotatably disposed within the housing. The second pulley is in operable engagement with the belt. The pulleys of the drive assembly are spaced from one another. The belt wraps around the pulleys of the drive assembly and around the annular member.

In another aspect of the present disclosure, a surgical assembly for use with a surgical robotic arm is provided. The surgical assembly includes an instrument drive unit, and a surgical instrument holder. The instrument drive unit includes a housing and a motor assembly rotatably disposed within the housing. The surgical instrument holder includes a carriage, a housing extending from the carriage, and a drive assembly. The carriage has a first side configured for movable engagement to a surgical robotic arm, and a second side configured for non-rotatably supporting the housing of the instrument drive unit. The carriage includes a motor. The housing of the instrument drive unit extends from the carriage and defines a channel. The drive assembly includes a pulley, a belt, and an annular member. The pulley is rotatably disposed within the housing of the surgical instrument holder and in operable engagement with the motor of the carriage such that actuation of the motor of the carriage rotates the pulley of the drive assembly. The belt is rotatably disposed within the housing and in operable engagement with the pulley such that rotation of the pulley effects rotation of the belt. The annular member is disposed within the channel of the housing and configured for non-rotatable receipt of the motor assembly of the instrument drive unit. The annular member is in operable engagement with the belt such that rotation of the belt causes the annular member to rotate resulting in rotation of the motor assembly of the instrument drive unit relative to the housing of the instrument drive unit.

In some embodiments, the annular member may include a ring and an annular base plate disposed within the ring. The ring may have the teeth of the annular member extending therefrom. The annular base plate may define one or more holes that receive drive shafts of the motor assembly therethrough. The ring and the annular base plate may cooperatively define a cavity configured to receive the motor assembly of the instrument drive unit.

It is contemplated that the surgical assembly may further include a surgical instrument configured for non-rotatable connection with the motor assembly of the instrument drive unit. Rotation of the motor assembly of the instrument drive unit via the drive assembly of the surgical instrument holder effects rotation of the surgical instrument.

Other aspects, features, and advantages will be apparent from the description, the drawings, and the claims that follow.

BRIEF DESCRIPTION OF THE DRAWINGS

Embodiments of the present disclosure are described herein with reference to the accompanying drawings, wherein:

FIG. 22 is a front, perspective view of a robotic surgical assembly, according to another embodiment of the present disclosure, shown supported on a slide rail of the robotic surgical system and coupled to an electromechanical surgical instrument;

FIG. 23 is a rear, perspective view of the robotic surgical assembly and electromechanical surgical instrument of FIG. 22;

FIG. 26 is a cross-sectional view as taken through 26-26 of FIG. 24;

FIG. 27 is a perspective view of a pulley of the robotic surgical assembly of FIG. 22;

FIG. 36 is a side, elevational view, with parts separated, of another embodiment of a robotic surgical assembly and embodiments of various electromechanical surgical instruments for use with the robotic surgical assembly of FIG. 2 or FIG. 36;

FIG. 37 is a top view of one embodiment of the various electromechanical surgical instruments shown in FIG. 36;

FIG. 64A is a cross-sectional view, taken along lines 64A-64A of FIG. 63, of the housing of the surgical instrument holder;

FIG. 64B is the cross-sectional view of the housing as shown in FIG. 64A with the addition of an annular member and a pulley of the drive assembly disposed therein;

FIG. 65A is a top view of the housing of FIG. 63;

FIG. 65B is a top view of the housing of FIG. 63 with the addition of a belt and a pulley of the drive assembly disposed therein;

DETAILED DESCRIPTION

Figure 1:
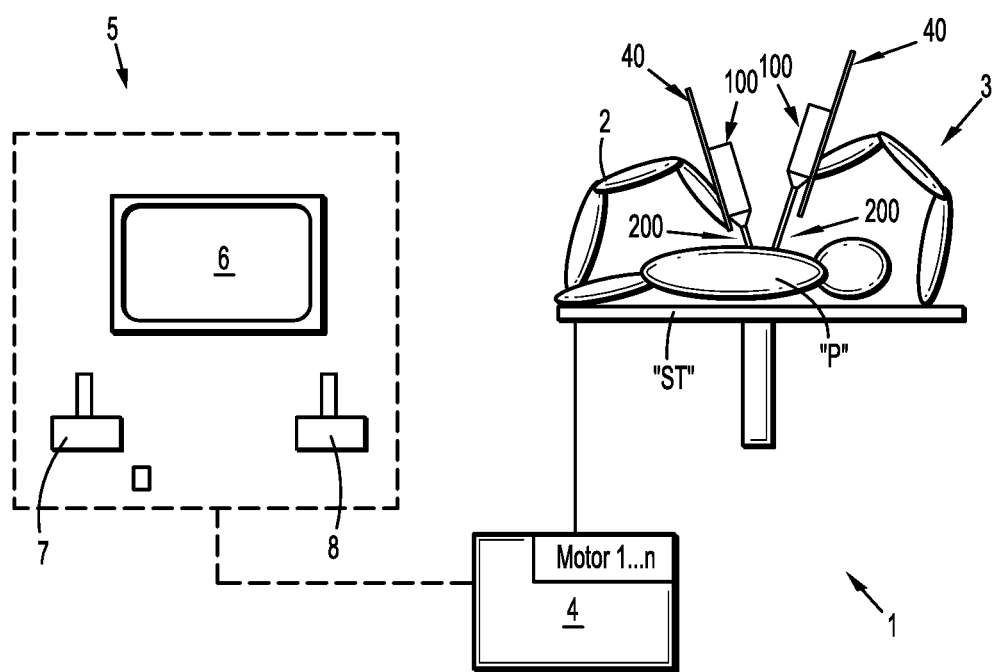
FIG. 1 is a schematic illustration of a robotic surgical system including a robotic surgical assembly in accordance with the present disclosure.

Embodiments of the presently disclosed surgical assembly including an instrument drive unit for driving the operation of an electromechanical surgical instrument and methods thereof are described in detail with reference to the drawings, in which like reference numerals designate identical or corresponding elements in each of the several views. As used herein, the term "distal" refers to that portion of the robotic surgical system, surgical assembly, or component thereof, that is closer to a patient, while the term "proximal" refers to that portion of the robotic surgical system, surgical assembly, or component thereof, that is further from the patient. As used herein, the terms parallel and perpendicular are understood to include relative configurations that are substantially parallel and substantially perpendicular up to about + or −10 degrees from true parallel and true perpendicular.

As used herein, the term "clinician" refers to a doctor, nurse, or other care provider and may include support personnel. In the following description, well-known functions or construction are not described in detail to avoid obscuring the present disclosure in unnecessary detail.

As will be described in detail below, provided is a surgical assembly configured to be attached to a surgical robotic arm. The surgical assembly includes an instrument drive unit having, for example, but not limited to, a motor configured to rotate an electromechanical instrument about a longitudinal axis thereof. In some embodiments, the motor may be a hollow core motor. Additionally, provided is a feedback assembly configured to determine and regulate the degree of rotation of the electromechanical instrument about its longitudinal axis. The rotation of the electromechanical instrument may be achieved with a hollow core motor, a canister motor (brushless or brushed), via a transmission (gear, belt and/or cable); via pneumatics, and/or via hydraulics. The axis of rotation of the electromechanical instrument may be integral to the instrument drive unit or to the robotic arm.

Referring initially to FIG. 1, a surgical system, such as, for example, a robotic surgical system 1, generally includes one or more surgical robotic arms 2, 3, a control device 4, and an operating console 5 coupled with control device 4. Any of the surgical robotic arms 2, 3 may have a robotic surgical assembly 100 and an electromechanical surgical instrument 200 coupled thereto. In some embodiments, the robotic surgical assembly 100 may be removably attached to a slide rail 40 of one of the surgical robotic arms 2, 3. In certain embodiments, the robotic surgical assembly 100 may be fixedly attached to the slide rail 40 of one of the surgical robotic arms 2, 3.

Operating console 5 includes a display device 6, which is set up to display three-dimensional images; and manual input devices 7, 8, by means of which a clinician (not shown), is able to telemanipulate the robotic arms 2, 3 in a first operating mode, as known in principle to a person skilled in the art. Each of the robotic arms 2, 3 may be composed of any number of members, which may be connected through joints. The robotic arms 2, 3 may be driven by electric drives (not shown) that are connected to control device 4. The control device 4 (e.g., a computer) is set up to activate the drives, for example, by means of a computer program, in such a way that the robotic arms 2, 3, the attached robotic surgical assembly 100, and thus the electromechanical surgical instrument 200 (including the electromechanical end effector, not shown) execute a desired movement according to a movement defined by means of the manual input devices 7, 8. The control device 4 may also be set up in such a way that it regulates the movement of the robotic arms 2, 3 and/or of the drives.

The robotic surgical system 1 is configured for use on a patient "P" positioned (e.g., lying) on a surgical table "ST" to be treated in a minimally invasive manner by means of a surgical instrument, e.g., the electromechanical surgical instrument 200. The robotic surgical system 1 may also include more than two robotic arms 2, 3, the additional robotic arms likewise connected to the control device 4 and telemanipulatable by means of the operating console 5. A surgical instrument, for example, the electromechanical surgical instrument 200 (including the electromechanical end effector thereof), may also be attached to any additional robotic arm(s).

The control device 4 may control one or more motors, e.g., motors (Motor 1 . . . n), each motor configured to drive movement of the robotic arms 2, 3 in any number of directions. Further, the control device 4 may control an instrument drive unit 110 including motors 52, 54, 56 and 58 of a motor pack 50 (FIGS. 2, 7 and 17-21A) disposed within a sterile barrier housing 130 of the robotic surgical assembly 100. The motors 52, 54, 56 and 58 of the motor pack 50 drive various operations of an end effector of the electromechanical surgical instrument 200. The motors 52, 54, 56 and 58 may include a rotation motor, such as, for example, a canister motor. One or more of the motors 52, 54, 56 and 58 may be configured to drive a relative rotation of the electromechanical surgical instrument 200, or components thereof, along a longitudinal axis "X" thereof. In some embodiments, each motor of motor pack 50 can be configured to actuate a drive screw 340 (or, for example, a linear drive, a capstan, etc.) which is operatively connected to a drive rod or a lever arm to effect operation and/or movement of the electromechanical end effector of the electromechanical surgical instrument 200.

In accordance with the present disclosure, the electromechanical surgical instrument 200 is rotated about a longitudinal axis of rotation thereof by a motor 44 (e.g., in one embodiment, a fifth axis motor, see FIG. 24) having a rotation axis that is offset a radial distance from the longitudinal axis of rotation of the electromechanical surgical instrument 200.

For a detailed discussion of the construction and operation of a robotic surgical system, reference may be made to U.S. Patent Application Publication No. 2012/0116416, filed on Nov. 3, 2011, entitled "Medical Workstation," the entire contents of which are incorporated by reference herein.

With continued reference to FIG. 1, the robotic surgical system 1 includes the robotic surgical assembly 100 that is coupled with or to the robotic arm 2 or 3, and the electromechanical surgical instrument 200 that is coupled to the robotic surgical assembly 100. The robotic surgical assembly 100 transfers power and actuation forces from its motors to driven members of the electromechanical surgical instrument 200 to ultimately drive movement of components of the end effector of electromechanical surgical instrument 200, for example, a movement of a knife blade (not shown) and/or a closing and opening of jaw members of the end effector, an articulation/rotation/pitch/yaw of the end effector, and/or the actuation or firing of a stapler. The robotic surgical assembly 100 may also be configured for the activation or firing of an electrosurgical energy-based instrument or the like (e.g., cable drives, pulleys, friction wheels, rack and pinion arrangements, etc.).

Figure 32:
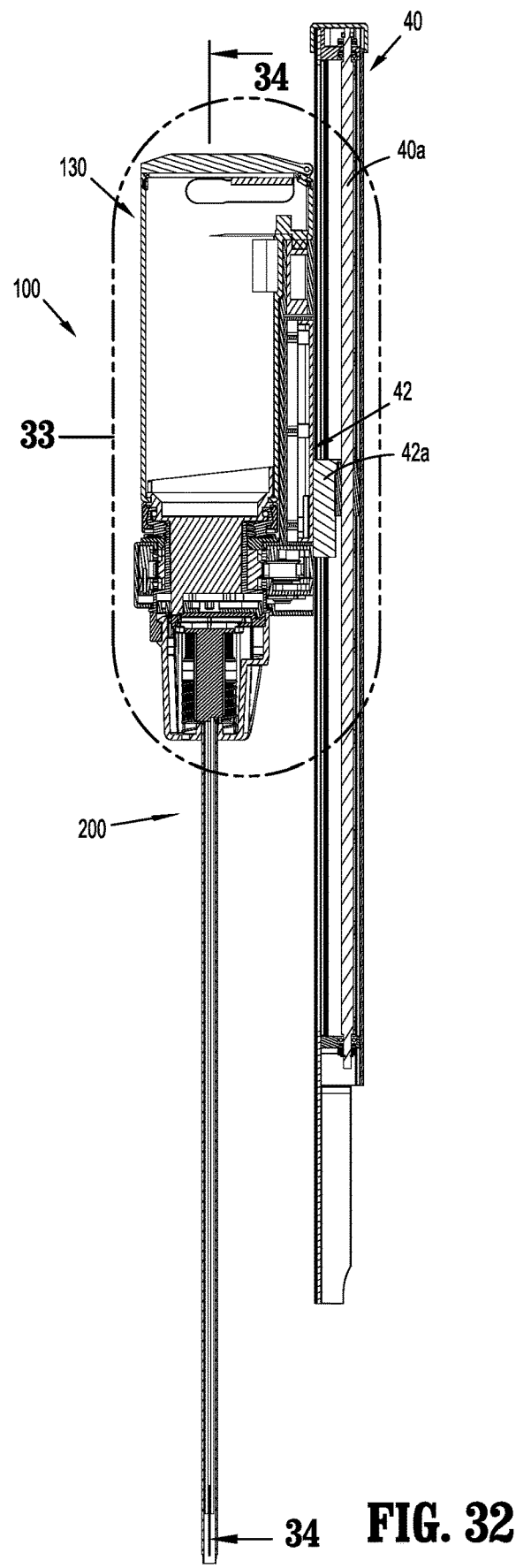
FIG. 32 is a longitudinal, cross-sectional view of the robotic surgical assembly and the electromechanical surgical instrument of FIG. 22, shown connected to the slide rail.
Figure 33:
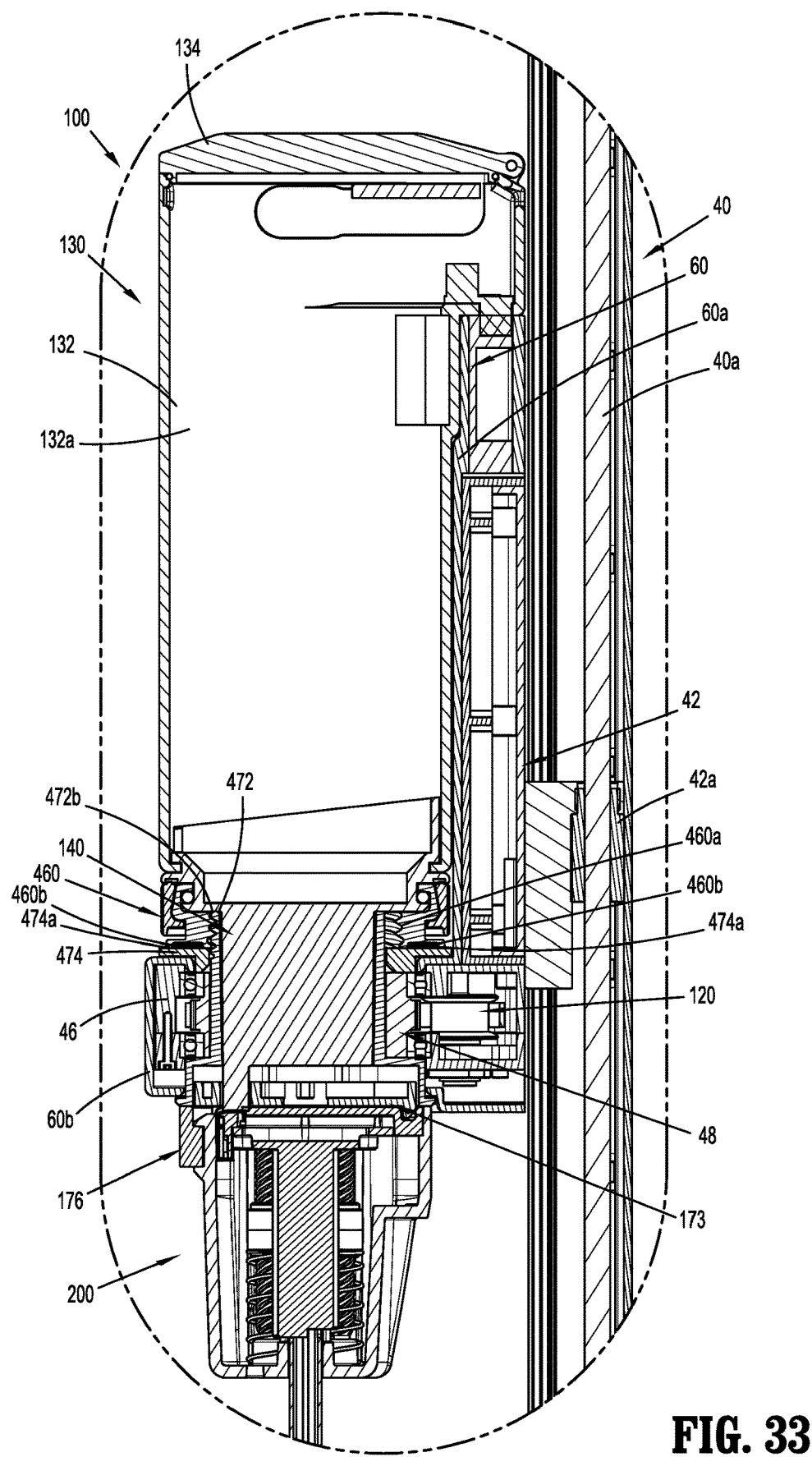
FIG. 33 is an enlarged view of the indicated area of detail of FIG. 32.
Figure 34:
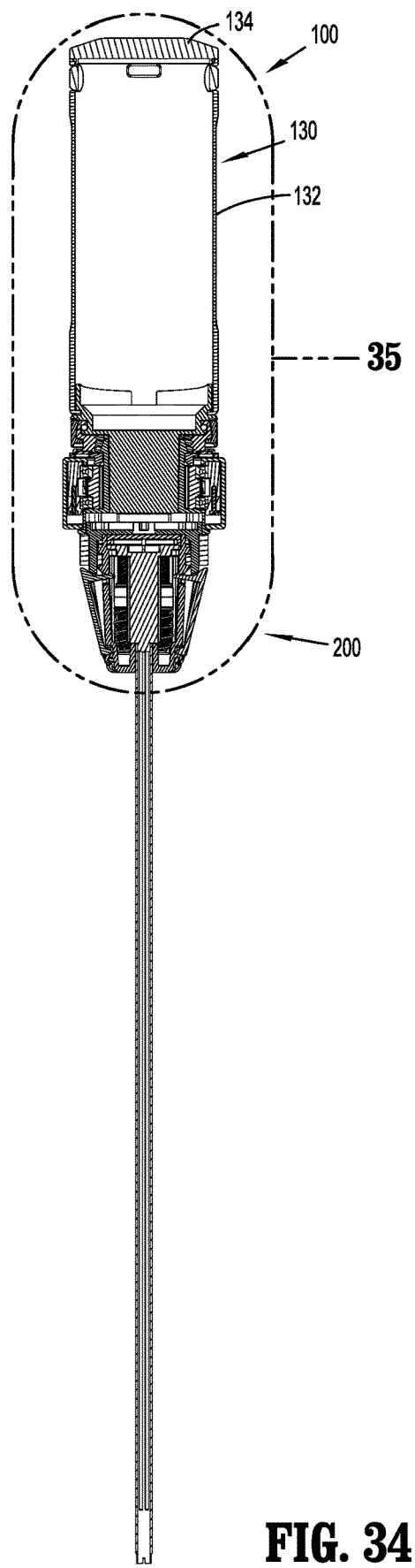
FIG. 34 is a cross-sectional view of the robotic surgical assembly and the electromechanical surgical instrument, as taken through 34-34 of FIG. 32.

Turning now to FIGS. 2-6, the robotic surgical assembly 100 is connectable to an interface panel or carriage 42 which is slidably mounted onto the rail 40. The carriage 42 supports or houses a motor 44 (see FIG. 24) that receives controls and power from the control device 4. The carriage 42 may be moved along the rail 40 via a motor driven chain or belt 41 (see FIG. 3) or the like. Alternatively, with reference to FIGS. 32 and 33, the carriage 42 may be moved along the rail 40 via a threaded rod/nut arrangement. For example, the carriage 42 may support a threaded nut or collar 42a which receives a threaded rod 40a therethrough. In use, as the threaded rod 40a is rotated, the threaded collar 42a (for example, see FIGS. 32 and 33), and in turn, the carriage 42 are caused to be translated along the rail 40. A coupling 46 (see FIG. 24), or the like, is connected to a drive shaft of motor 44, and may be rotated clockwise or counter clockwise upon an actuation of the motor 44. While a chain/belt 41 or threaded rod and collar arrangement 40a/42a are shown and described, it is contemplated that any other systems capable of achieving the intended function may be used (e.g., cable drives, pulleys, friction wheels, rack and pinion arrangements, etc.).

Figure 2:
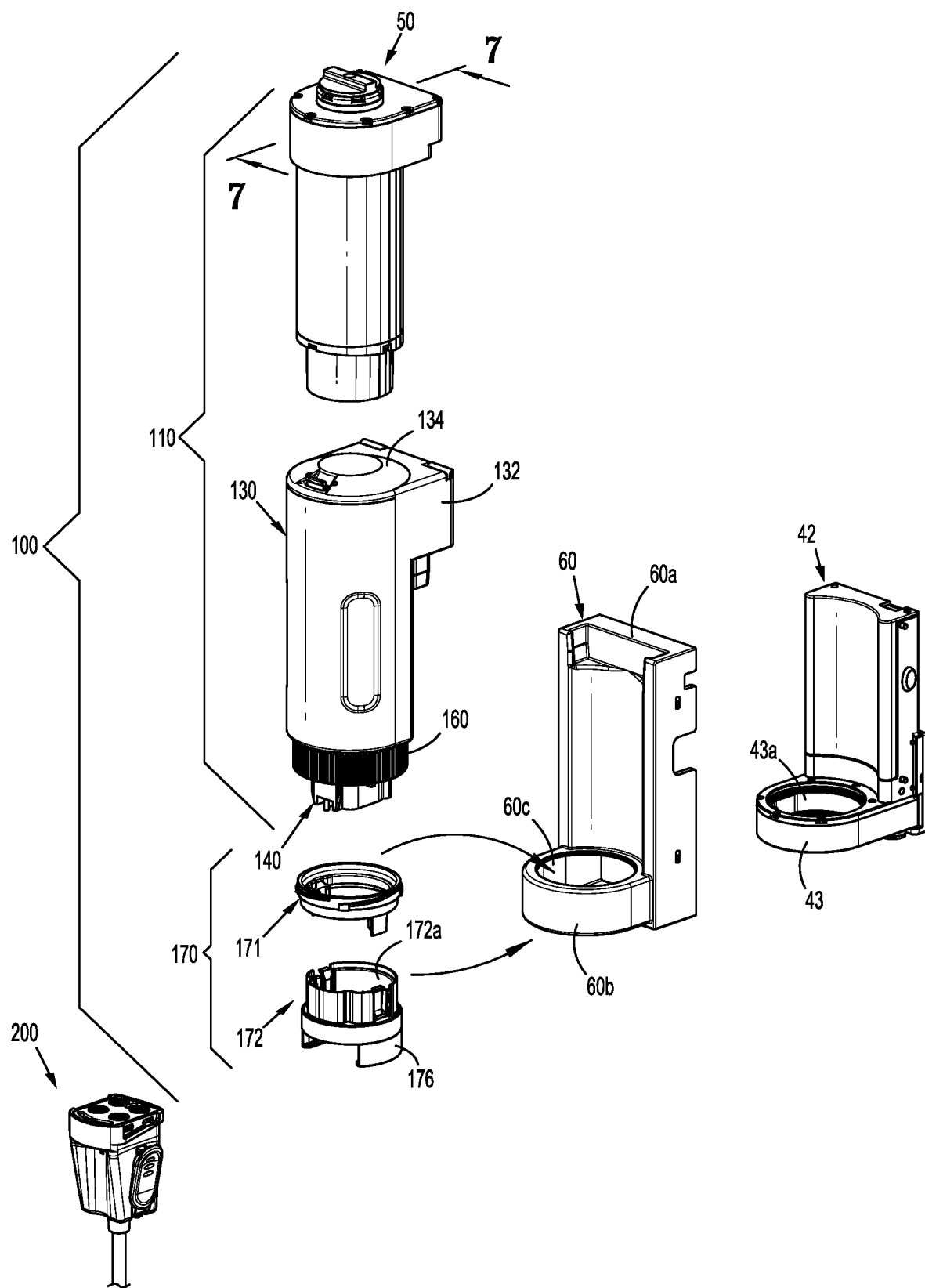
FIG. 2 is a perspective view, with parts separated, of the robotic surgical assembly and the electromechanical surgical instrument, in accordance with an embodiment of the present disclosure.
Figure 3:
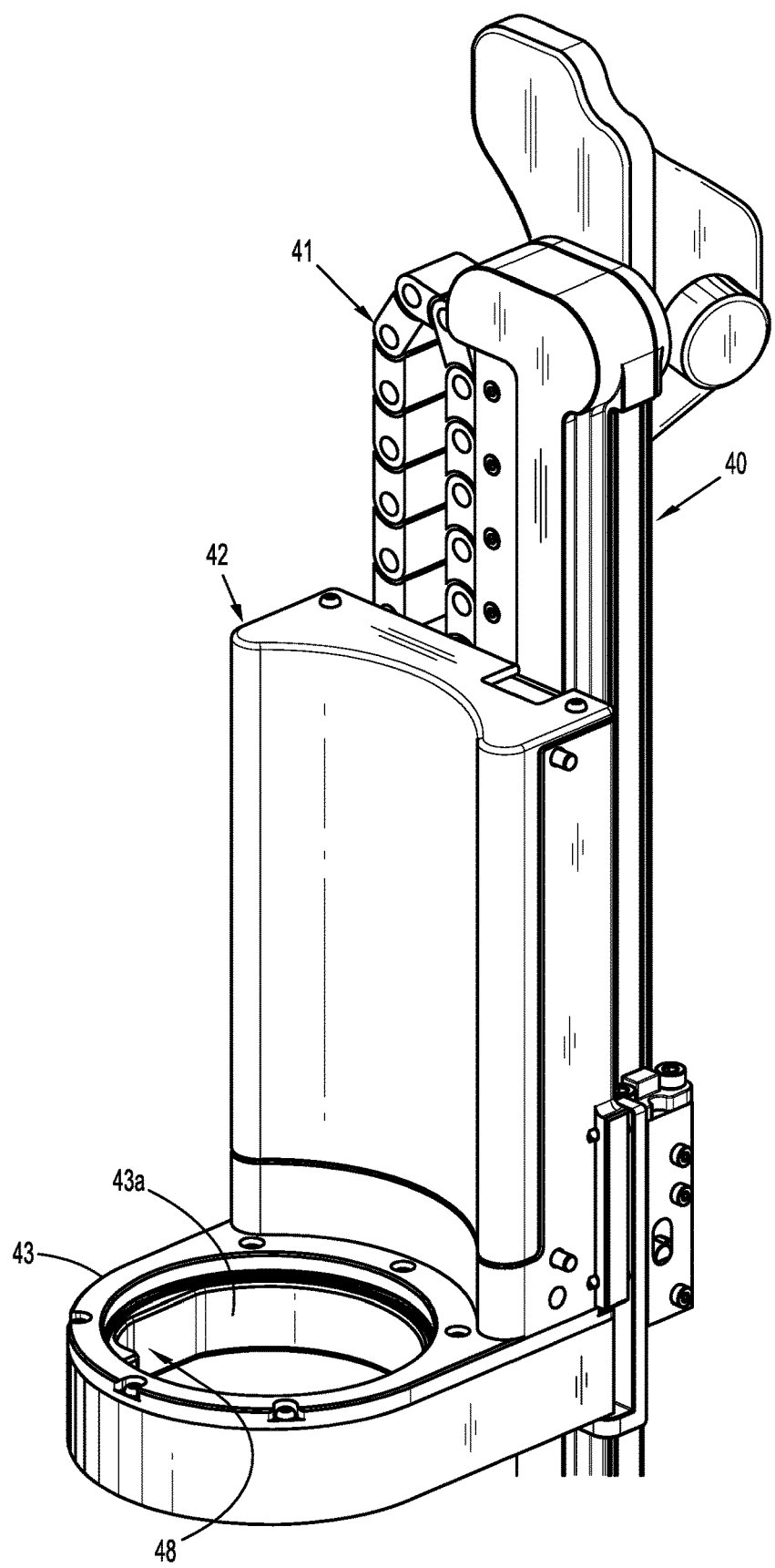
FIG. 3 is a perspective view of a carriage of the robotic surgical assembly, shown supported on a rail slide of the robotic surgical system.
Figure 4:
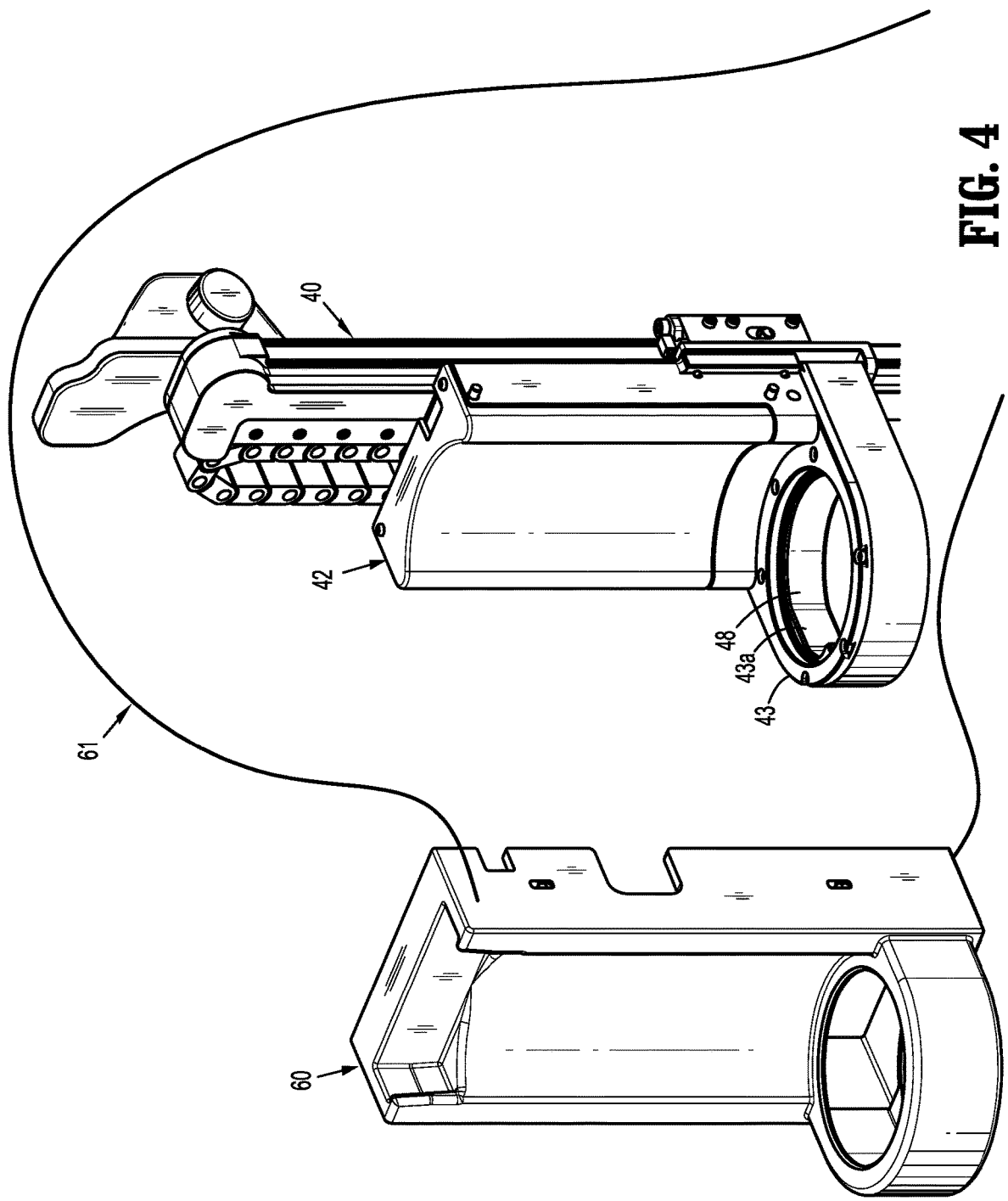
FIG. 4 is a perspective view of the carriage and rail of FIG. 3, illustrating a sterile shell and bag of the robotic surgical system being coupled and connected to the carriage and rail.
Figure 5:
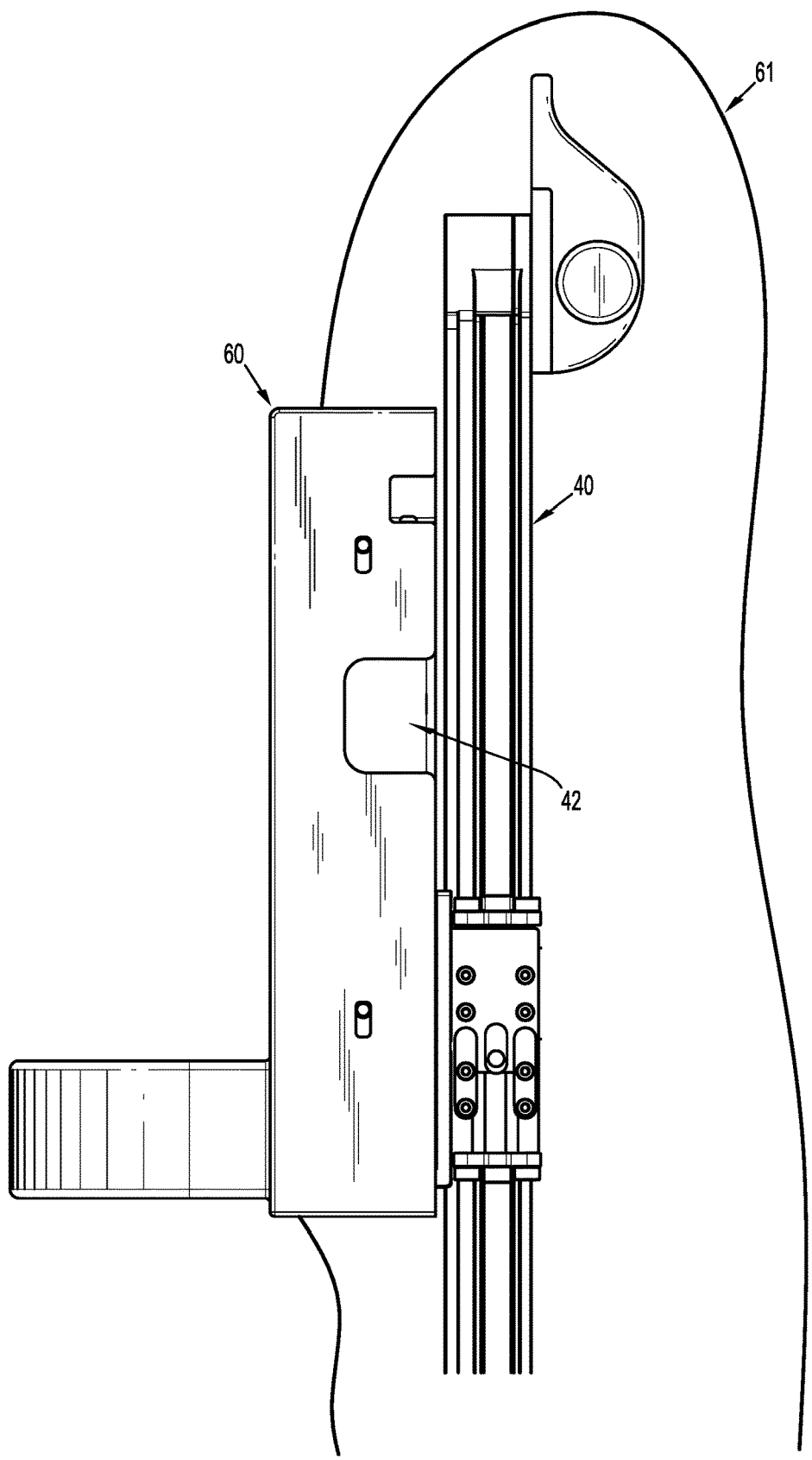
FIG. 5 is a side, elevational view of the carriage and rail of FIGS. 3 and 4, illustrating the sterile shell and bag of the robotic surgical system coupled and connected to the carriage and rail.
Figure 6:
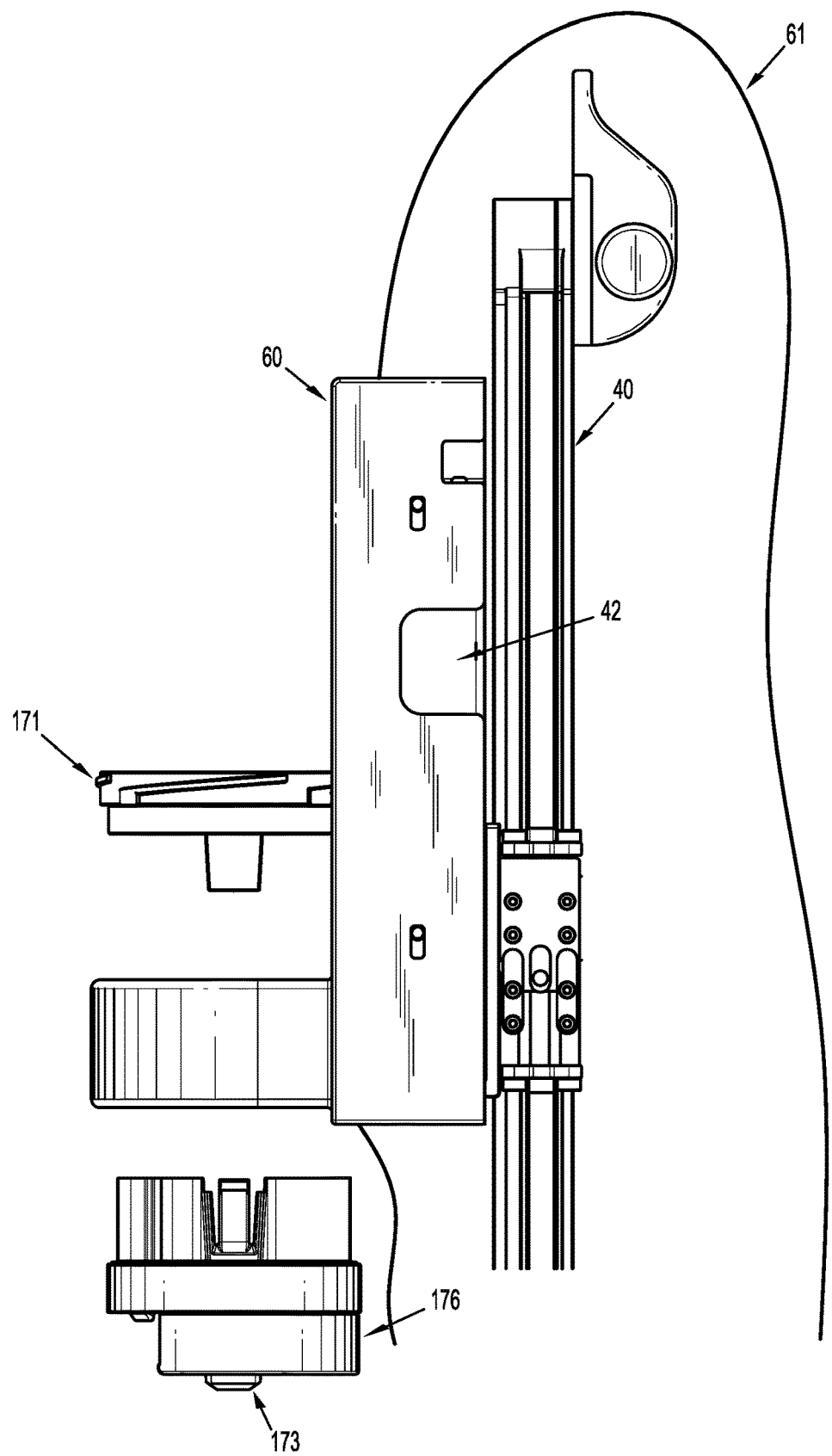
FIG. 6 is a side, elevational view of the carriage and rail of FIG. 5, illustrating a coupling or connection of a sterile barrier collar assembly according to an embodiment of the present disclosure, to the carriage and rail.
Figure 7:
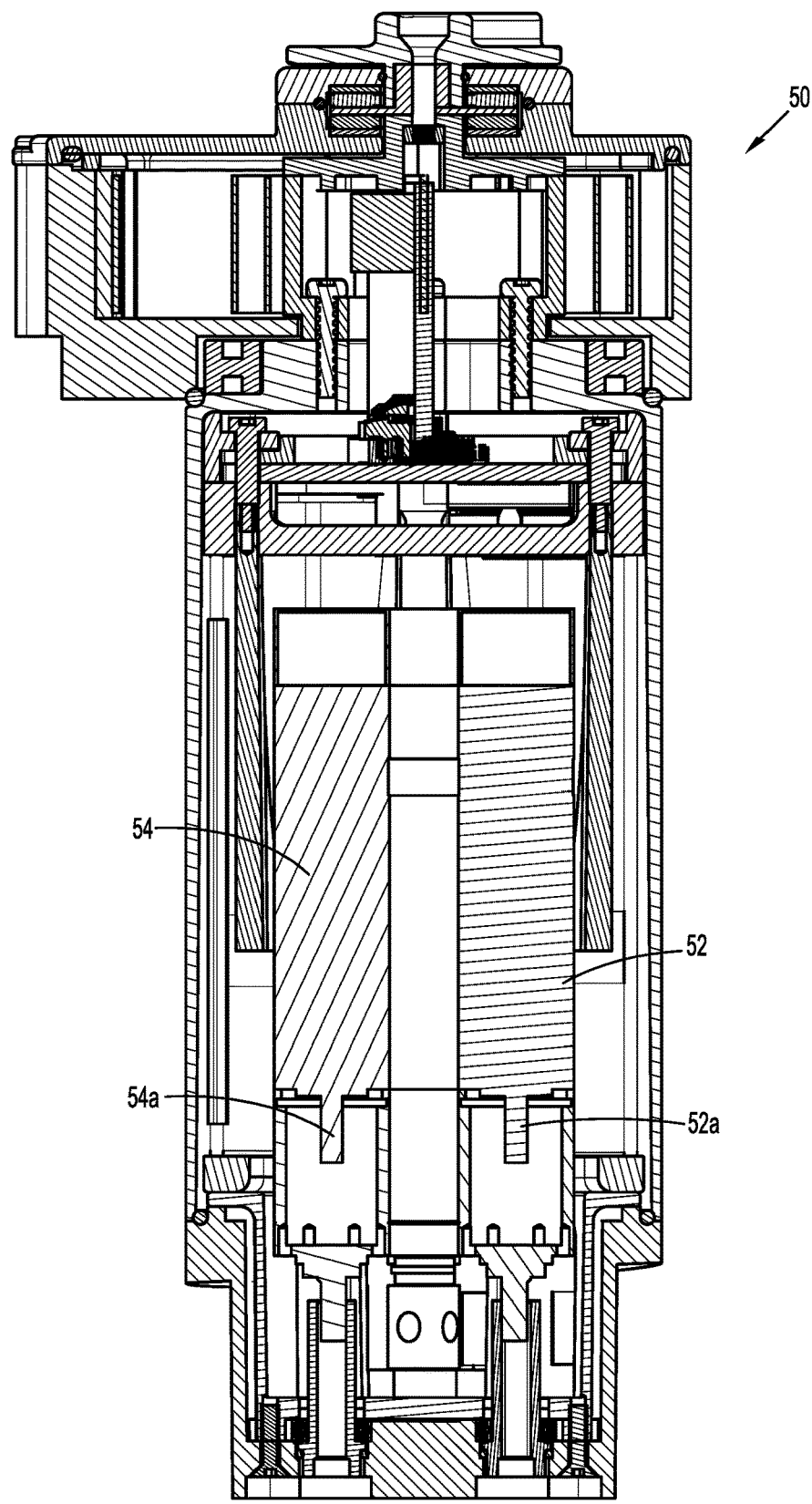
FIG. 7 is a longitudinal, cross-sectional view of a motor pack of the robotic surgical assembly illustrated in FIG. 2, as taken through 7-7 of FIG. 2.
Figure 8:
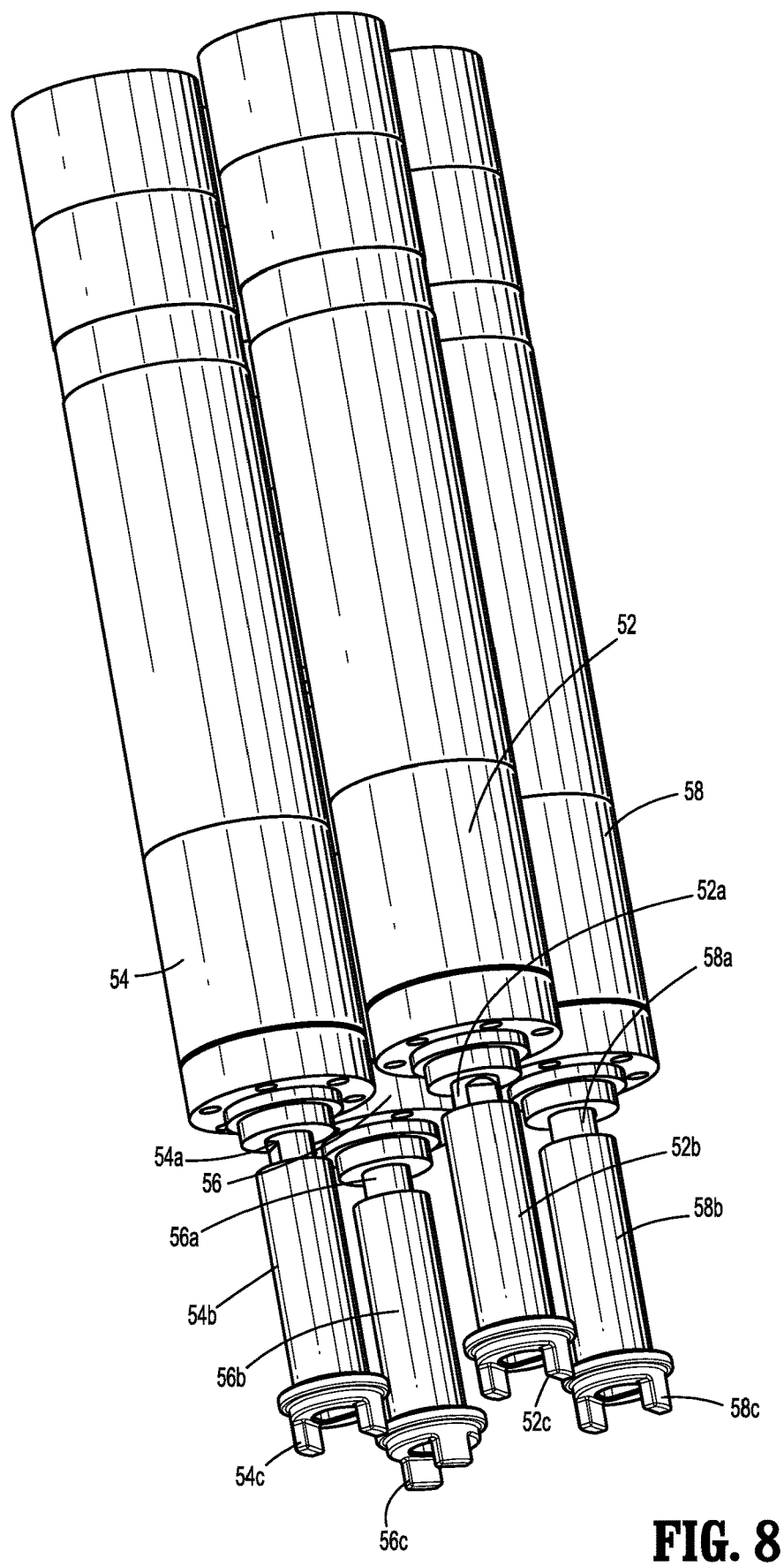
FIG. 8 is a perspective view of canister motors and respective motor couplers of the motor pack of FIG. 7.

With reference to FIGS. 2-6 and 17-21A, the carriage 42 includes a coupling flange 43 extending or projecting from a rear panel 42a thereof and from the rail 40. With reference to FIGS. 2-4, the coupling flange 43 of the carriage 42 defines an opening or bore 43a therethrough, and rotatably supports an instrument rotation gear or pulley 48. The pulley 48 has ring-shaped, non-circular, transverse, cross-sectional profile passage or opening therethrough (e.g., substantially D-shaped, or the like) which defines a key-way for non-rotational receipt of a drive transfer assembly 140 of the sterile barrier housing 130. The pulley 48 is rotatably supported in the coupling flange 43 by journal bearings or the like.

Figure 24:
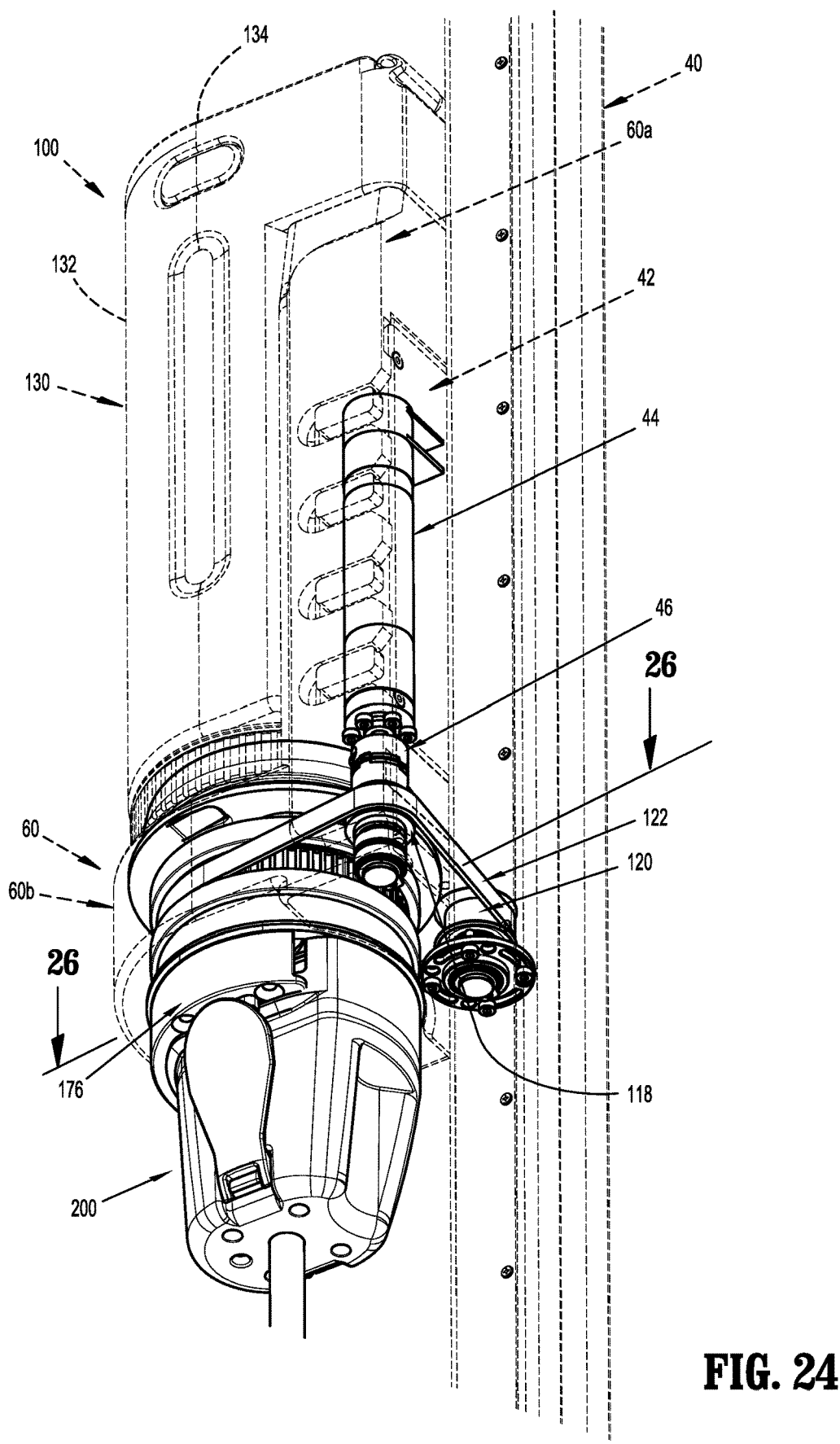
FIG. 24 is a bottom, perspective view of the electromechanical surgical instrument connected to the robotic surgical assembly of FIG. 22, with portions thereof shown in phantom.
Figure 25:
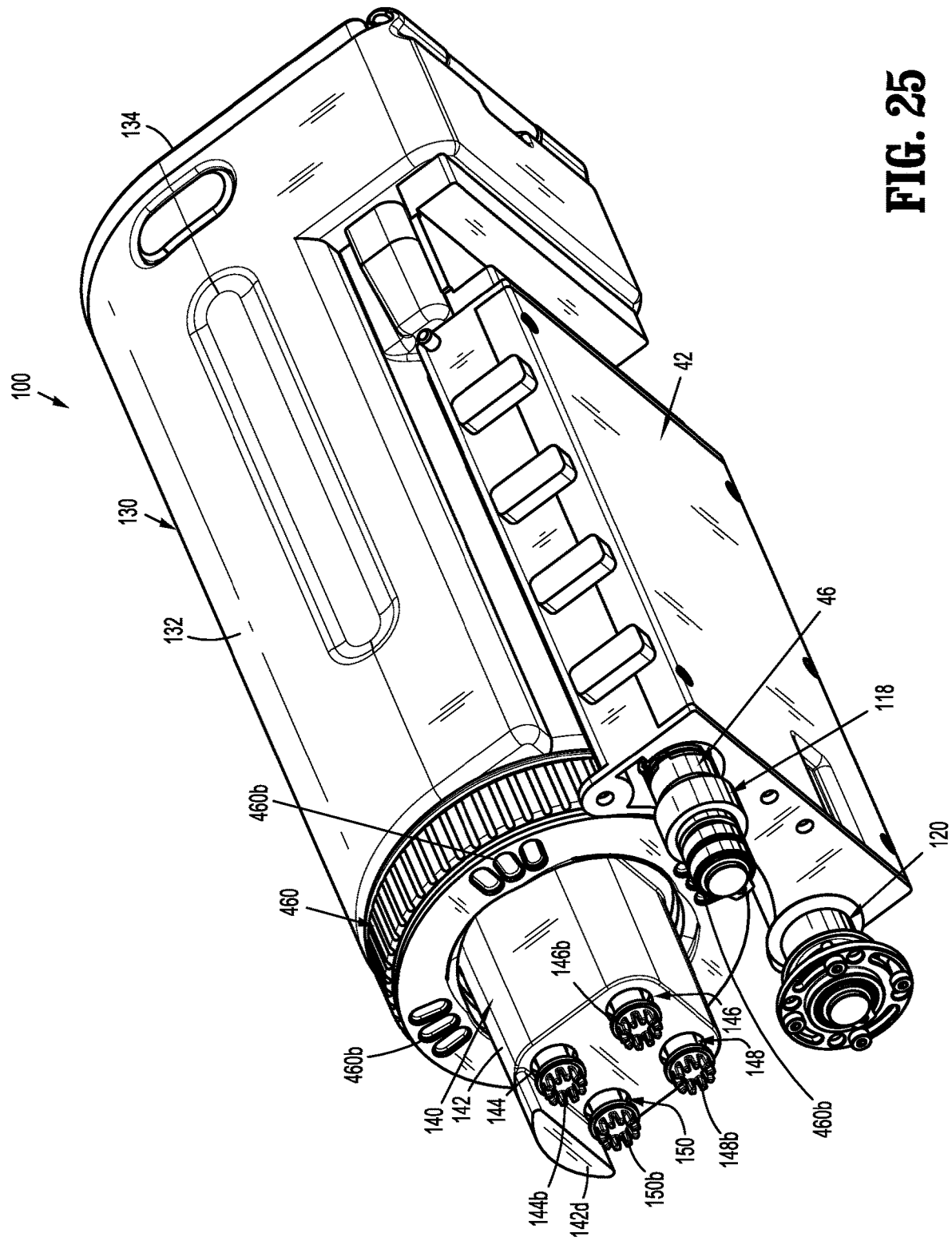
FIG. 25 is a bottom, perspective view of the robotic surgical assembly of FIG. 22.

With reference momentarily to FIGS. 24-26, the carriage 42 may rotatably support motor axis gear or pulley 118 (e.g., a spur gear) and a tension gear or pulley 120 within coupling flange 114. A drive belt 122 or the like extends around the pulley 48, the motor axis pulley 118 and the tension pulley 120. The motor axis pulley 118 is connectable to the coupling 46 of the motor 44, and is driven by the motor 44 upon an actuation thereof. Accordingly, in use, as the motor 44 is actuated, the motor 44 drives the coupling 46, which drives the motor axis pulley 118, to in turn drive the belt 122, and in turn, rotate the pulley 48.

With reference to FIGS. 2-6, a sterile shell or barrier 60 is provided which shrouds or covers the carriage 42. Shell 60 includes a rear shell portion 60a configured and adapted to cover the rear panel 42a of the carriage 42, and an annular shell portion 60b extending from rear shell portion 60a and configured to cover the coupling flange 43 of the carriage 42. The annular shell portion 60b of the shell 60 defines an opening 60c in registration with a passage or opening 48a of the pulley 48 having a non-circular, transverse cross-sectional profile (e.g., substantially D-shaped, or the like). A sterile drape 61 or the like may be secured or adhered to the shell 60 and may be pulled over the rail 40 and the robotic arm 2 or 3 to establish and maintain a sterile barrier between the patient "P," the surgical field, and/or the robotic surgical system 1.

With reference to FIGS. 2 and 17-21A, the robotic surgical assembly 100 includes a sterile barrier housing 130 configured to mate with or otherwise connect to the shell 60. The sterile barrier housing 130 includes a hollow shell or body 132 defining a cavity therein. The sterile barrier housing 130 pivotally or hingedly supports a proximal cap or cover 134 configured and adapted to selectively close a proximal end of the body 132. The sterile barrier housing 130 further includes a drive transfer assembly 140 supported on, or connected to, a distal end of the body 132.

The cavity of the body 132 of the sterile barrier housing 130 is configured to slidably receive a motor pack 50 or the like (see FIGS. 2, 7, 8 and 17-21A) therein. The motor pack 50 may include four motors 52, 54, 56, 58 arranged in a rectangular formation such that respective drive shafts 52a, 54a, 56a, and 58a thereof are all parallel to one another and all extend in a common direction. The drive shaft 52a, 54a, 56a, and 58a of each motor 52, 54, 56, and 58, respectively, may operatively interface with a respective drive coupler 144a, 146a, 148a and 150a of the drive transfer assembly 140 (see FIGS. 9-11). The motor pack 50 may include four canister motors or the like, each having a drive shaft having a non-circular transverse cross-sectional profile (e.g., substantially D-shaped, or the like).

For an exemplary motor pack 50 for use in the robotic surgical assembly 100, reference may be made to U.S. Provisional Patent Application Ser. No. 62/181,817, filed on Jun. 19, 2015, entitled "Robotic Surgical Assemblies," the entire contents of which are incorporated by reference herein.

With reference to FIGS. 8-11 and 17-20, a motor coupler 52b, 54b, 56b, and 58b may be non-rotatably connected to a respective drive shaft 52a, 54a, 56a, and 58a of each motor 52, 54, 56, and 58, respectively. Each motor coupler 52b, 54b, 56b, and 58b may have a substantially tubular configuration defining a lumen therethrough having a non-circular transverse cross-sectional profile. The lumen of each motor coupler 52b, 54b, 56b, and 58b is configured to non-rotatably engage and/or receive respective drive shaft 52a, 54a, 56a, and 58a of each motor 52, 54, 56, and 58, respectively, wherein the lumens may have a substantially D-shaped transverse, cross-sectional profile.

Each motor coupler 52b, 54b, 56b, and 58b includes one or more distally extending tab 52c, 54c, 56c, and 58c which is/are configured to engage a respective mating feature or slot 144c, 146c, 148c and 150c of the drive couplers 144a, 146a, 148a and 150a of the drive transfer shafts 144, 146, 148 and 150 to transmit rotational forces from the motors 52, 54, 56, and 58 to respective drive transfer shafts 144, 146, 148 and 150 of the drive transfer assembly 140 in the manner of an "oldham coupling." This oldham-type coupling limits backlash and enables autocorrecting when components thereof are slightly misaligned with one another. In some embodiments, one or more of these tabs and/or slots may have complementary v-shaped configurations. It is contemplated that any rotational force transmitting feature may be provided at the distal end of the motor couplers 52b, 54b, 56b, and 58b. In use, as any one of the motors 52, 54, 56, and 58 is activated to rotate a respective drive shaft 52a, 54a, 56a, and 58a, the particular drive shaft drive shaft 52a, 54a, 56a, and 58a transmits the rotation to the respective motor coupler 52b, 54b, 56b, and 58b, which in turn, transmits the rotation (via tabs 52c, 54c, 56c, and 58c) to the respective drive couplers 144a, 146a, 148a and 150a of the drive transfer shafts 144, 146, 148 and 150 of the drive transfer assembly 140. Such an arrangement and coupling permits a degree of flotation of the motor couplers 52b, 54b, 56b, and 58b and the drive couplers 144a, 146a, 148a and 150a in any radial direction relative to a longitudinal axis thereof.

With reference to FIGS. 9-12 and 17-21A, the drive transfer assembly 140 of the sterile barrier housing 130 includes a body portion 142 extending from the distal end of the body 132. The body portion 142 of the drive transfer assembly 140 has a non-circular form (e.g., substantially D-shaped, as illustrated) outer profile for keyed receipt within a complementary non-circular (e.g., D-shaped, as illustrated) passage or opening 48a of the pulley 48 of the carriage 42. While a D-shaped transverse cross-sectional profile is shown and described, any non-circular transverse cross-sectional profile may be used to provide a keyed connection, including and not limited to hex, Allen, star, cross, double "D", "T", torx, val, phillips, helix profiles.

Figure 9:
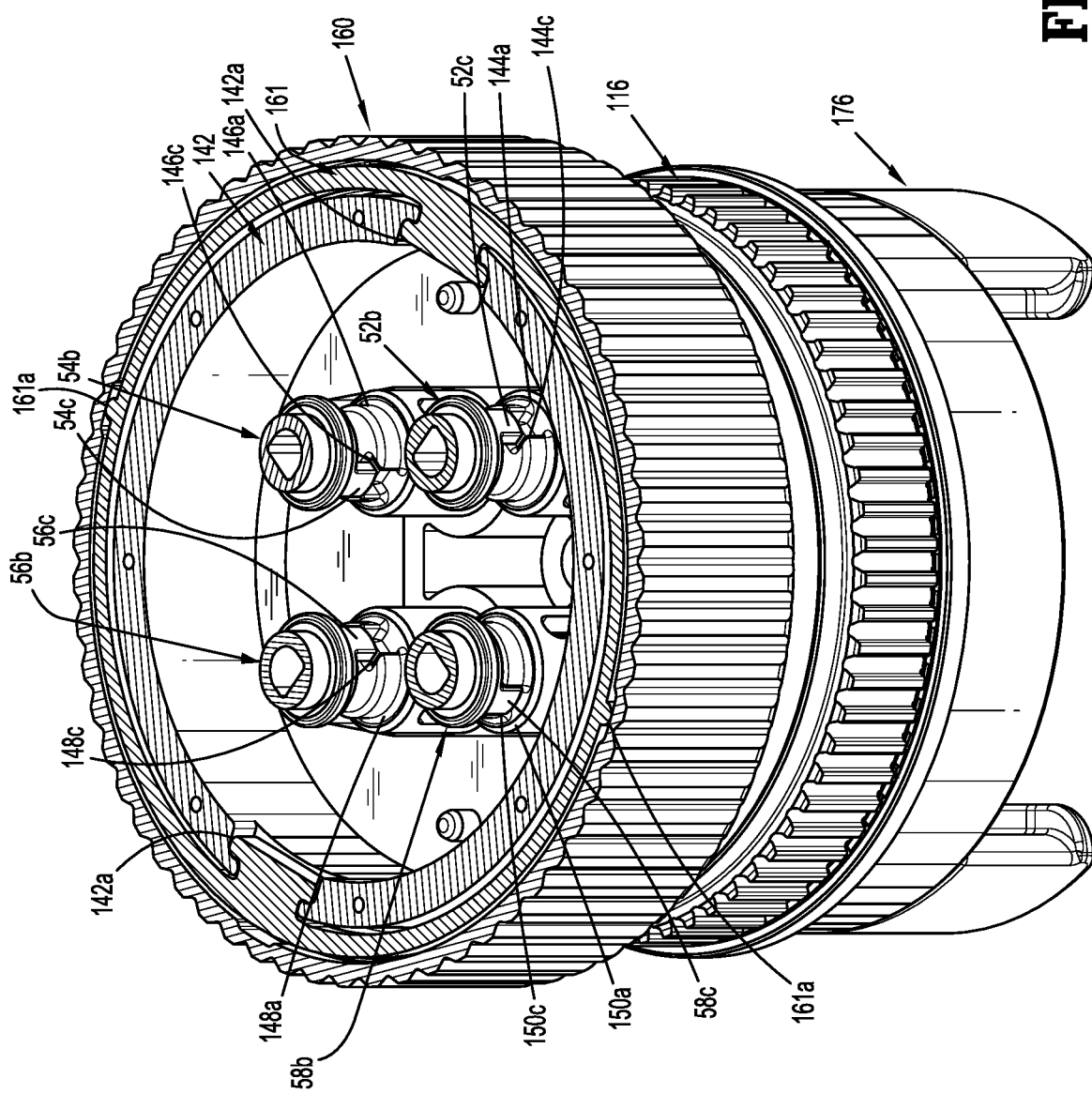
FIG. 9 is a transverse cross-sectional view of components of the motor pack, a drive transfer assembly, and a lock ring of the robotic surgical assembly of the present disclosure.

The drive transfer assembly 140 rotatably supports at least one, and as shown in FIGS. 11 and 18-20, four drive transfer shafts (only drive transfer shafts 144 and 148 being shown). As illustrated, a proximal end of each drive transfer shaft (e.g., 144 and 148) non-rotatably supports a respective drive coupler (e.g., 144a and 148a, respectively), via the motor couplers 52b, 54b, etc., which are configured and adapted for non-rotatable connection to a drive shaft 52a, 54a, 56a, and 58a of a respective motor 52, 54, 56 and 58 of motor pack 50. In particular, each drive coupler 144a, 146a, 148a and 150a is translatably supported on respective drive transfer shaft 144, 146, 148 and 150 via a pin-slot arrangement such that the couplers 144, 146, 148 and 150 may float on respective drive transfer shaft 144, 146, 148 and 150. With particular reference to FIG. 9, each drive coupler 144a, 146a, 148a and 150a defines a respective mating feature 144c, 146c, 148c and 150c configured to receive and transmit rotational forces from respective drive shafts 52a, 54a, 56a, and 58a of the motors 52, 54, 56 and 58 of the motor pack 50.

A distal end of each drive transfer shaft 144, 146, 148 and 150 supports a respective drive coupler 144b, 146b, 148b and 150b, which are configured and adapted for non-rotatable connection to proximal couplers 310 of drive assemblies 300 of the electromechanical surgical instrument 200. It is contemplated that each drive coupler 144b, 146b, 148b and 150b may resemble a crown gear or the like.

A respective biasing member 144d, 146d, 148d and 150d (e.g., compression spring) may be interposed between the drive couplers 144a, 146a, 148a and 150a and the drive couplers 144b, 146b, 148b and 150b, wherein the biasing members 144d, 146d, 148d and 150d maintain the drive couplers 144a, 146a, 148a and 150a in an extended condition, and maintain a distal floating plate 173 in an extended condition, as will be described in greater detail below.

Figure 11:
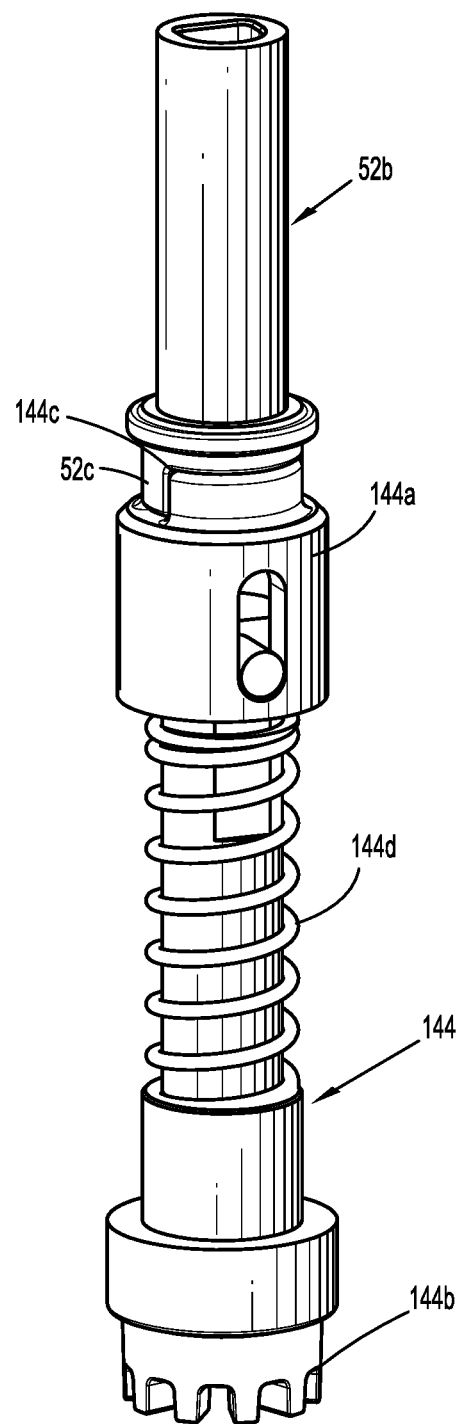
FIG. 11 is a perspective view illustrating a drive coupler of the sterile barrier collar assembly connected to a respective motor coupler.
Figure 12:
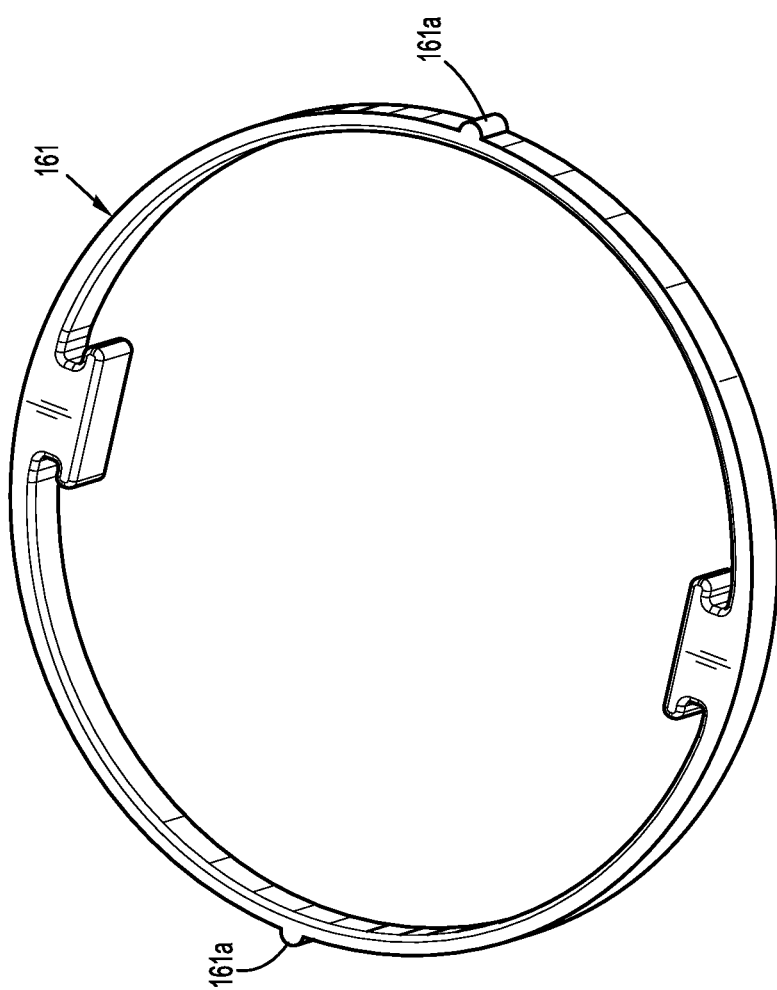
FIG. 12 is a perspective view of a tactile ring of the sterile barrier collar assembly.
Figure 21A:
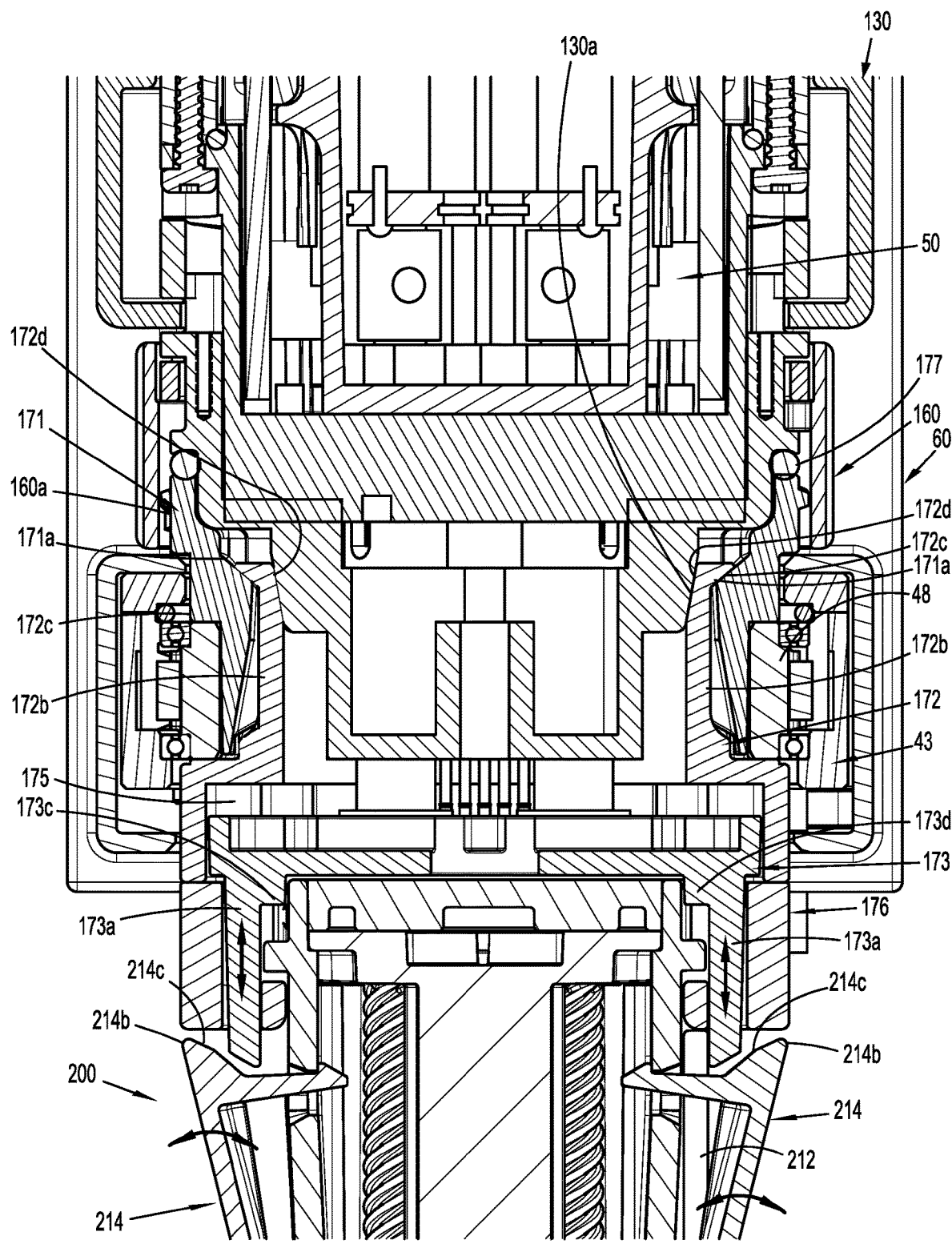
FIG. 21A is a longitudinal, cross-sectional view of the electromechanical surgical instrument coupled to the robotic surgical assembly, as taken through a plane extending across release levers or paddles of the electromechanical surgical instrument, and illustrating the electromechanical surgical instrument coupled to the carrier via the sterile barrier collar assembly.

While FIG. 11 only illustrates the drive transfer shaft 144 connected to the drive shaft 52b (of the motor 52), in the interest of brevity, each of the remaining drive transfer shafts 146, 148 and 150 are constructed in the same or similar manner as the drive transfer shaft 144 and will not be described in great detail herein. Additionally, as seen in FIG. 21A, a biasing member 175, in the form or a spring, may act on the distal floating plate 173 to help maintain the distal floating plate 173 in an extended condition.

In use, as the motors 52, 54, 56, and 58 of the motor pack 50 are actuated, rotation of the drive shafts 52a, 54a, 56a, and 58a of the motors 52, 54, 56, and 58, respectively, is transferred to the proximal couplers 310 of the drive assemblies 300 of the electromechanical surgical instrument 200 via respective drive transfer shafts 144, 146, 148 and 150.

Figure 10:
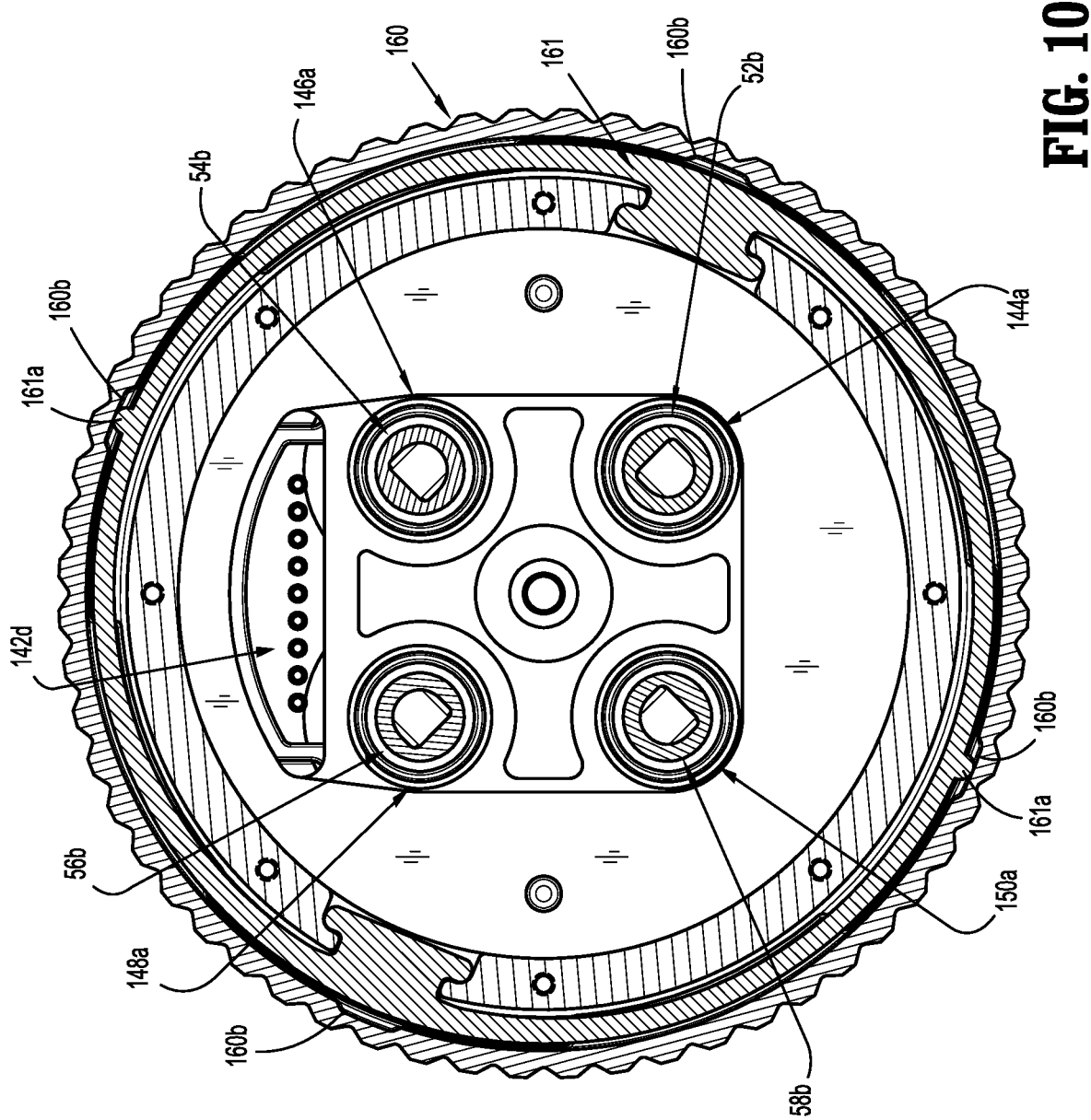
FIG. 10 is a top, plan view of the sterile barrier collar assembly of FIG. 9.
Figure 28:
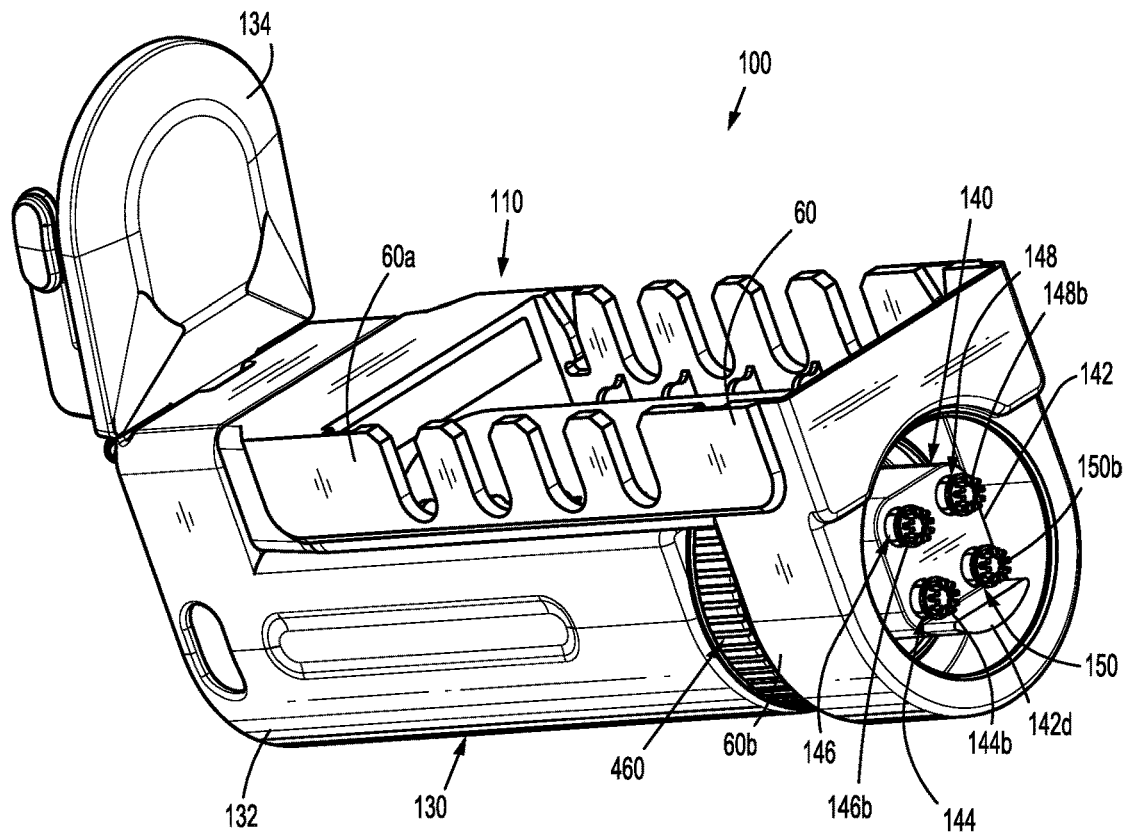
FIG. 28 is a rear, bottom perspective view of a sterile barrier of the robotic surgical assembly of FIG. 22.
Figure 29:
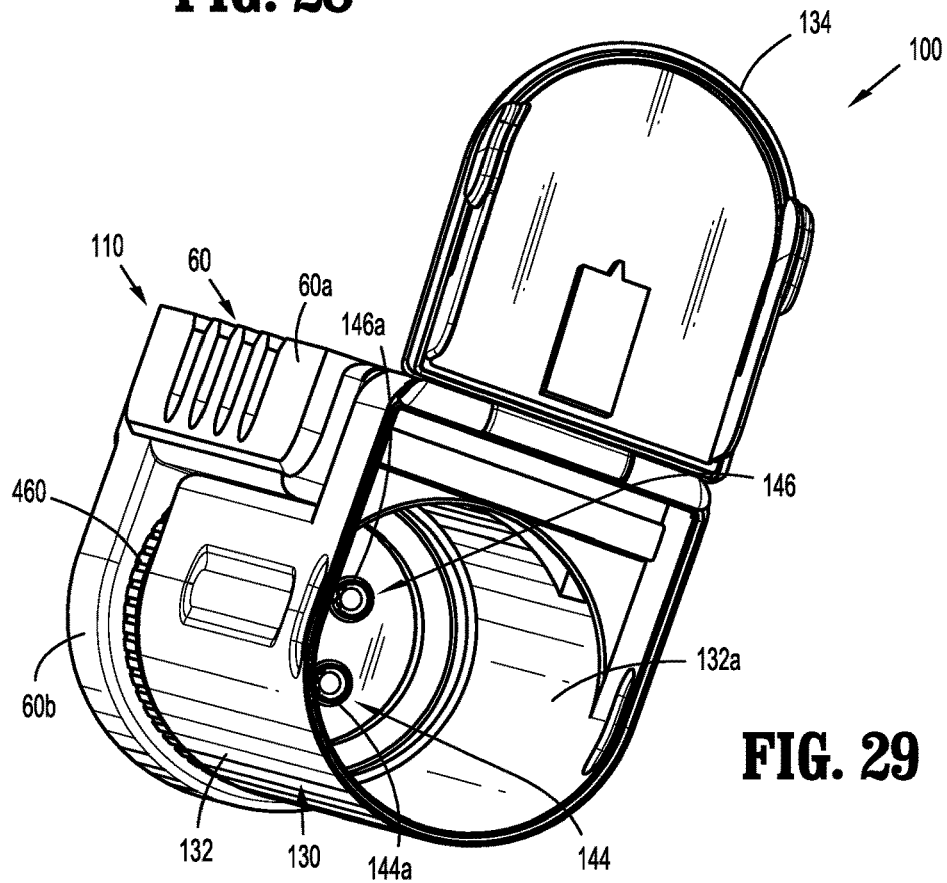
FIG. 29 is a front, top perspective view of the sterile barrier of the robotic surgical assembly of FIG. 22.
Figure 30:
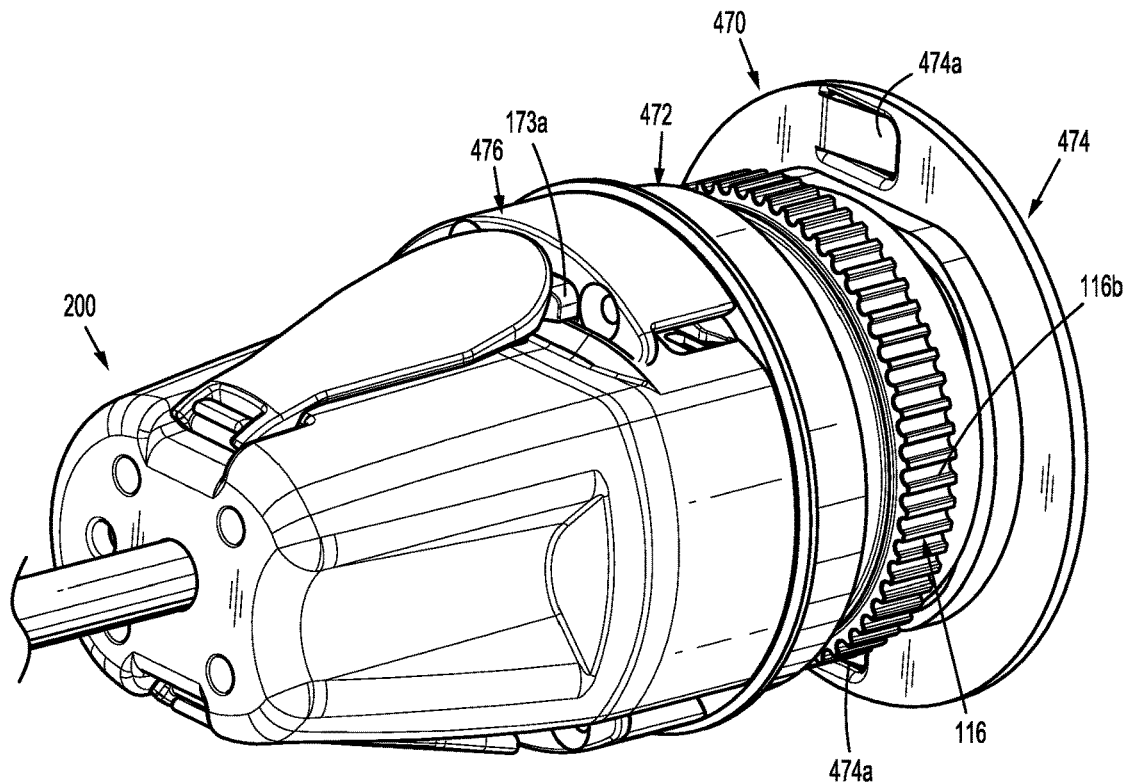
FIG. 30 is a front, perspective view of the electromechanical surgical instrument shown connected to a sterile barrier collar assembly of the robotic surgical assembly of FIG. 22.
Figure 31:
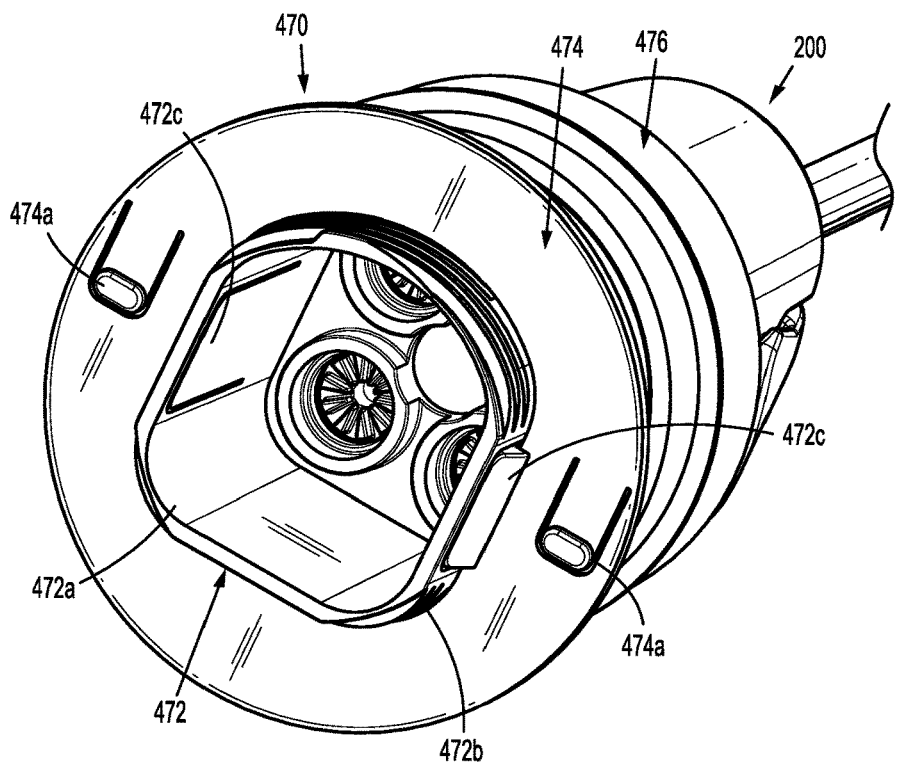
FIG. 31 is a rear, perspective view of the electromechanical surgical instrument shown connected to the sterile barrier collar assembly of the robotic surgical assembly of FIG. 22.

With reference to FIGS. 10, 25 and 28, the body portion 142 of the drive transfer assembly 140 includes a distally extending tab or tongue 142d, forming a plug. The plug 142d is configured to support electrical connectors therein for enabling electrical interconnection between the motor pack 50 contained in the sterile barrier housing 130 and an electrical connector 220 (FIG. 13) of the electromechanical surgical instrument 200.

As illustrated in FIGS. 2, 9, 10 and 17-21A, the robotic surgical assembly 100 includes a lock ring or collar 160 rotatably supported on the distal end of the body 132 of the sterile barrier housing 130. The lock collar 160 projects distally from the body 132 of the sterile barrier housing 130, and defines an internal thread 160a (see FIGS. 17-21A) configured for threadable connection to a proximal ring connector 171 (see FIGS. 2, 6 and 17-21A) of the sterile barrier collar assembly 170, as will be described in great detail below.

With reference to FIGS. 9 and 10, the lock ring or collar 160 non-rotatably supports a tactile feedback ring 161 therewithin. The tactile feedback ring 161 includes one or more radially outwardly projecting nubs or ribs 161a configured to be received in a corresponding recess 160b (FIG. 10) defined in an inner surface of the lock ring or collar 160. The tactile feedback ring 161 further includes one or more dovetail connectors 161b or the like projecting radially inwardly therefrom and configured for coupling or mating with a corresponding recess 142a formed in the body portion 142 of the drive transfer assembly 140.

In use, as a clinician rotates the drive transfer assembly 140, about a longitudinal axis thereof, to a desired angular orientation, the nub or rib 161a of the tactile feedback ring 161 selectively enters corresponding recesses 160b of the lock ring or collar 160 to provide tactile feedback to the clinician as to the angular orientation of the drive transfer assembly 140. It is contemplated that the recesses 160b of the lock ring or collar 160 and the nubs or ribs 161a of the tactile feedback ring 161 are provided whereby tactile feedback is provided for every 90° angular orientation of the drive transfer assembly 140, or any other desired or envisioned angular orientation.

Turning now to FIGS. 2, 13 and 17-21A, the robotic surgical assembly 100 includes a sterile barrier collar assembly 170 connectable to the annular shell 60b of the shell 60 and extendable through the D-shaped passage or opening 48a of the pulley 48. Specifically, the sterile barrier collar assembly 170 includes a tubular sleeve body 172 having a non-circular, transverse cross-sectional outer profile (e.g., substantially D-shaped, or the like), and an inner bore 172a having a complementary non-circular, transverse cross-sectional profile (e.g., substantially D-shaped, or the like).

The sterile barrier collar assembly 170 further includes a semi-annular coupling cuff 176 supported on or otherwise secured to a distal end of the tubular sleeve body 172. The coupling cuff 176 includes, as illustrated at least in FIG. 13, a U-shaped body portion 176a having an open side edge or instrument opening 176b that opens distally and laterally, and a pair of opposed side arms 176c. Each side arm 176c of the body portion 176a includes a ramp surface 176d formed in or projecting from an inner juxtaposed surface thereof. Each ramp 176d increases in height from a distal end (near the open side edge 176b) to a proximal end (near a backspan of the body portion 176a). It is contemplated that each ramp 176d may be angled at approximately 10° relative to a planar distal surface of the coupling cuff 176. Each side arm 176c of the body portion 176a further includes a recess or channel 176e formed in a surface thereof which is configured to slidably receive a respective arm or tab 173a of the distal floating plate 173 that is connected to or otherwise extending from a distal end of the tubular sleeve body 172.

The sterile barrier collar assembly 170 further includes the distal floating plate 173, as mentioned above. The distal floating plate 173 includes a pair of parallel arms or tabs 173a extending therefrom, and which are dimensioned to extend through, and project from, the recesses or channels 176e of the coupling cuff 176.

The distal floating plate 173 further defines a pattern of openings that may include and is not limited to a radial or a rectangular array of openings 173b therein through which the distal end of each drive transfer shaft 144, 146, 148 and 150 of the drive transfer assembly 140 extends. Specifically, the drive couplers 144b, 146b, 148b and 150b of respective drive transfer shafts 144, 146, 148 and 150 are rotatably seated in a respective opening 173b of the distal floating plate 173.

In operation, with the coupling cuff 176 connected to distal end of the tubular sleeve body 172, the biasing members 144d, 146d, 148d and 150d press the drive couplers 144a, 146a, 148a and 150a of respective drive transfer shafts 144, 146, 148 and 150 to an extended condition, which in turn, press against the distal floating plate 173 to maintain the distal floating plate 173 in the extended condition, whereby the pair of parallel arms or tabs 173a of the distal floating plate 173 extend through and project from the recesses or channels 176e of the coupling cuff 176.

The sterile barrier collar assembly 170 functions to maintain a sterile barrier between sterile components (e.g., the sterile barrier housing 130, the electromechanical surgical instrument 200, etc.) and non-sterile components (e.g., the robotic arms 2, 3, the motor pack 50, etc.). Specifically, the sterile barrier collar assembly 170 extends through the opening of the annular shell 60b of the shell 60, and, more specifically, through the D-shaped passage or opening 48a of the pulley 48 of the carriage 42. In operation, as the motor 44 of the interface panel 42 is actuated, the motor 44 drives the pulley 48 (as described above), which in turn, causes the sterile barrier collar assembly 170 to rotate. With the drive transfer assembly 140 extending through and keyed to the inner bore 172a of the tubular sleeve body 172 of the sterile barrier collar assembly 170, as the sterile barrier collar assembly 170 is rotated, the drive transfer assembly 140 is rotated, which in turn rotates the motor pack 50, which is rotatably retained or contained in sterile barrier housing 130.

Turning now to FIGS. 13-21A, the electromechanical surgical instrument 200 is shown and will be described. The electromechanical surgical instrument 200 may have a surgical instrument or end effector (not shown) secured to or securable to a distal end thereof. The electromechanical surgical instrument 200 is configured to transfer rotational forces/movement supplied by the robotic surgical assembly 100 (e.g., via the motors 52-58 of the motor pack 50) into longitudinal movement of the drive members 380 to effect various functions thereof.

The electromechanical surgical instrument 200 includes a housing assembly 210 including a housing 212 defining at least one cavity or bore 212a therein which is configured to receive a drive assembly 300 therein. In accordance with the present disclosure, the bore 212a of the housing 212 is configured to operatively support four separate drive assemblies 300 therein. It is contemplated that the bore 212a may be configured to define four separate discrete or interconnected bore portions with each portion operatively supporting a separate one of the four drive assemblies 300.

Figure 15:
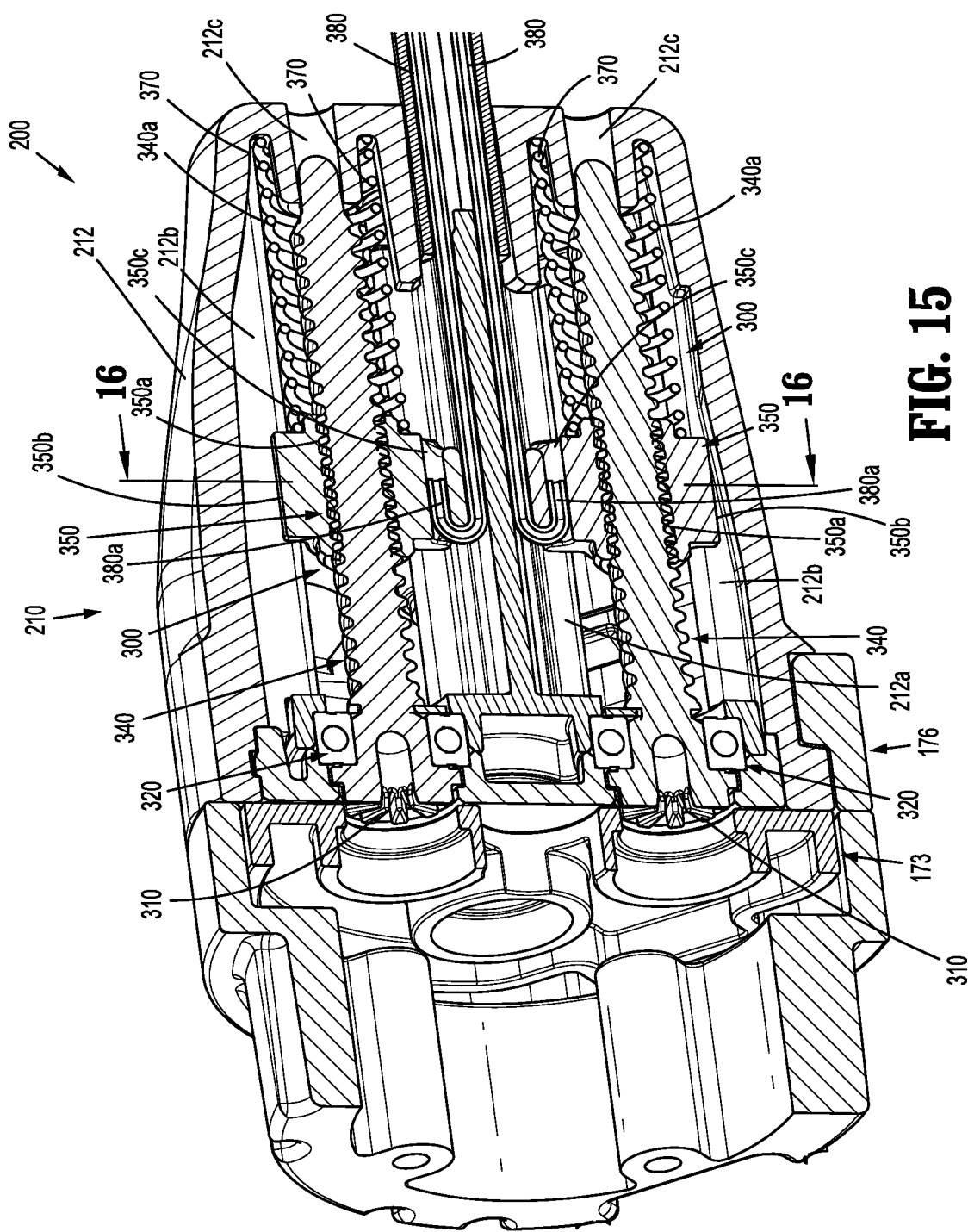
FIG. 15 is a cross-sectional view, as taken through 15-15 of FIG. 13.
Figure 16:
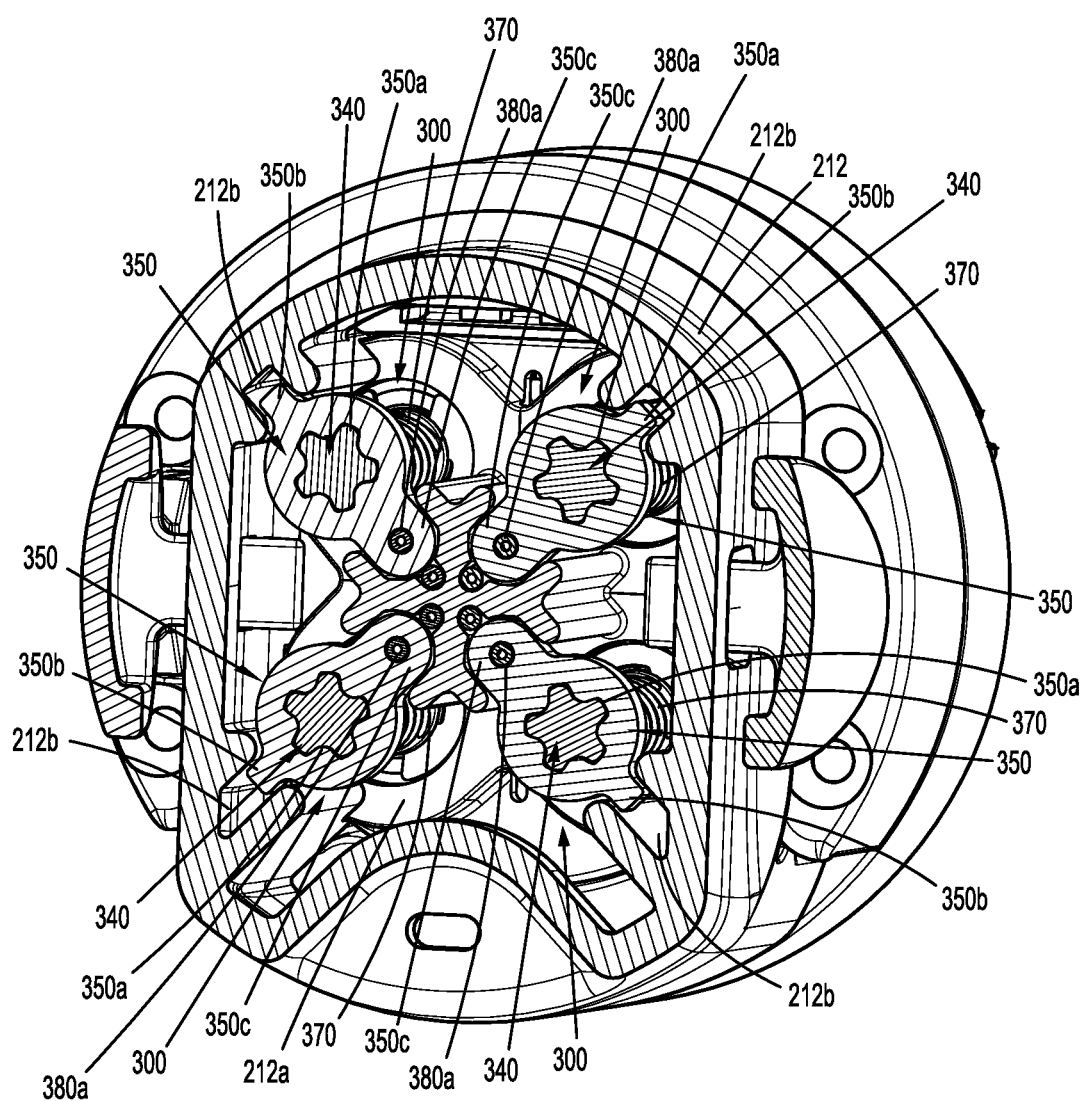
FIG. 16 is a cross-sectional view, as taken through 16-16 of FIG. 15.
Figure 17:
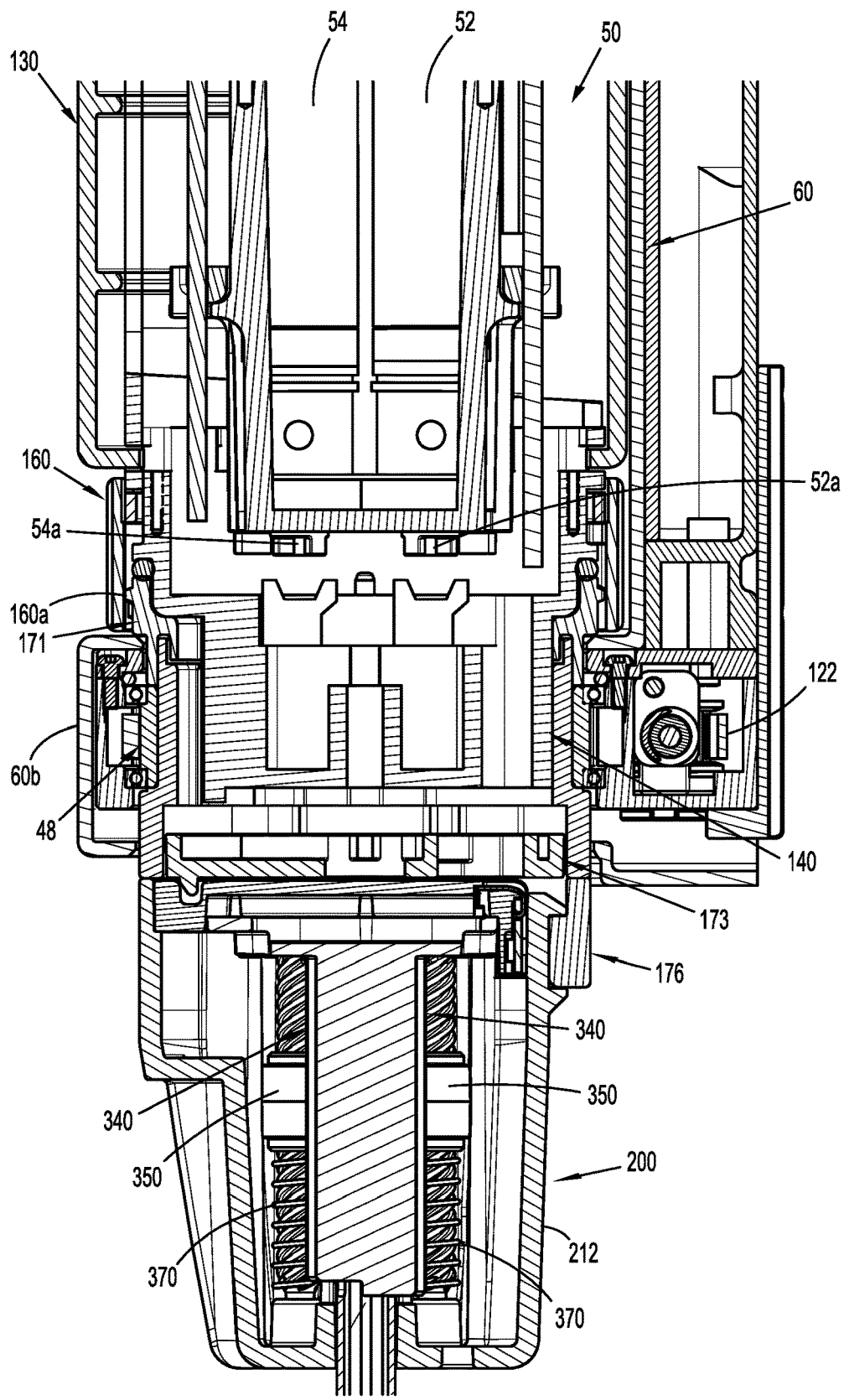
FIG. 17 is an enlarged, longitudinal, cross-sectional view of the electromechanical surgical instrument coupled to the carrier via the sterile barrier collar assembly.
Figure 18:
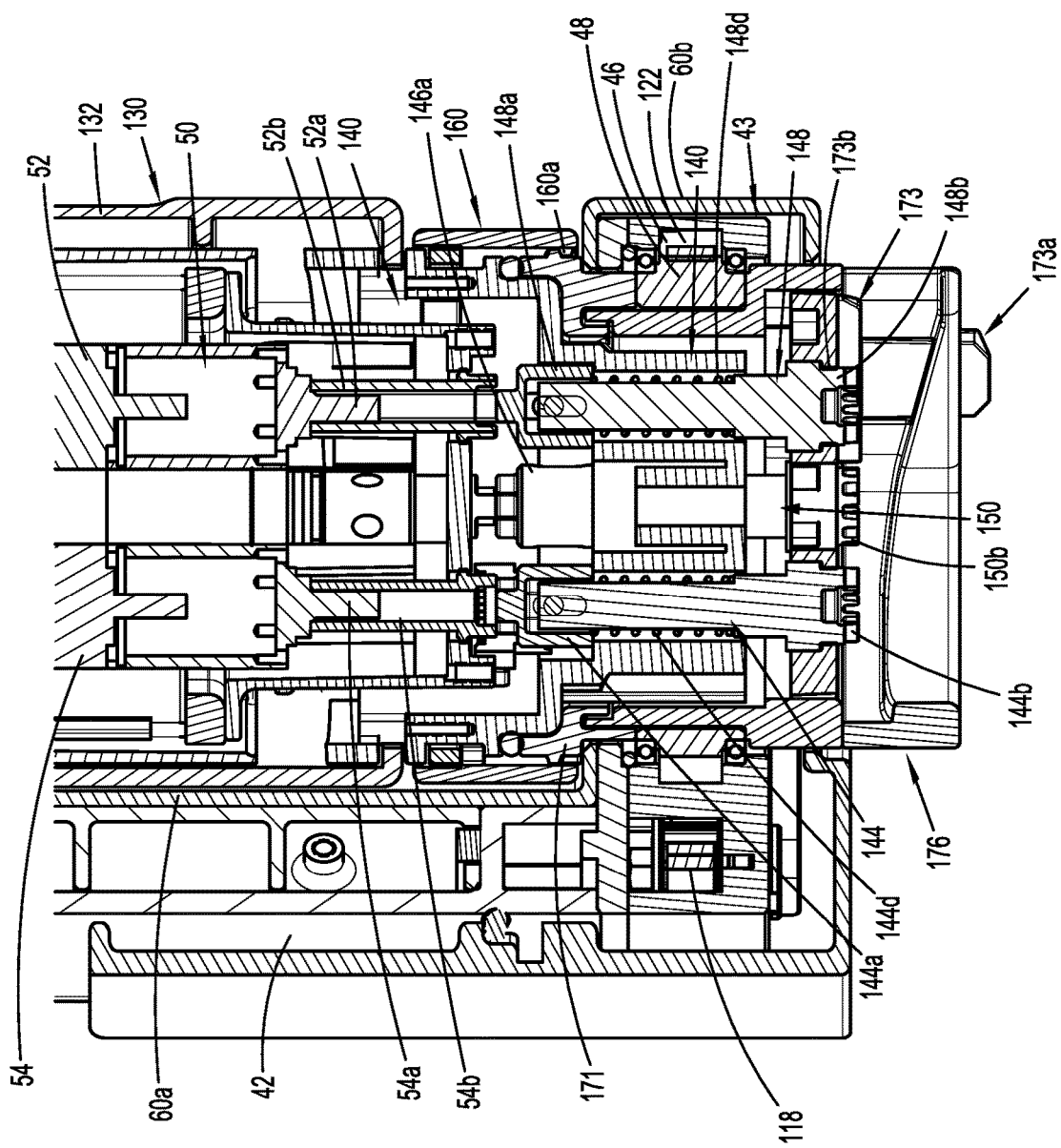
FIG. 18 is a further enlarged view of the illustration of FIG. 17, with the electromechanical surgical instrument removed therefrom.
Figure 19:
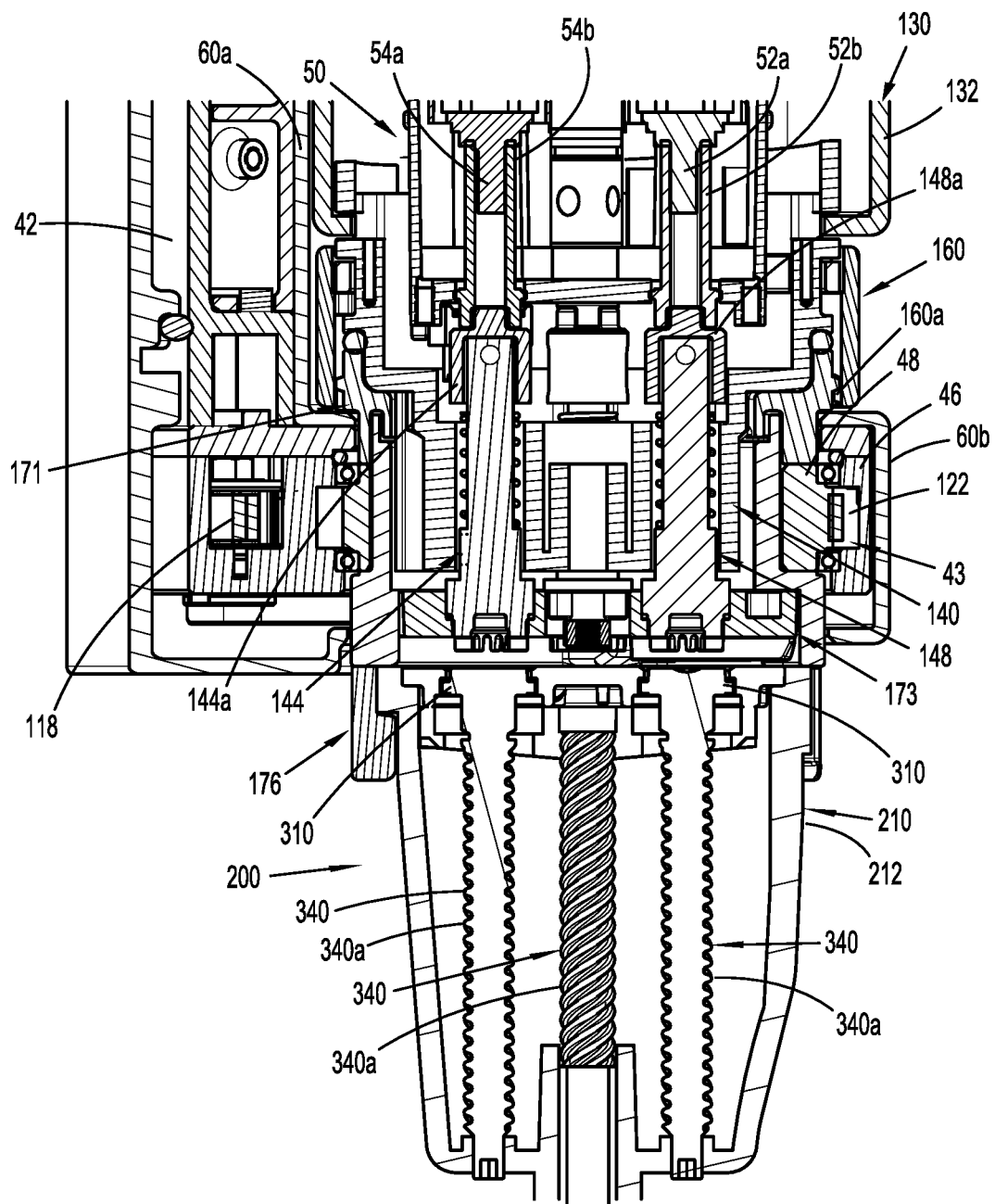
FIG. 19 is yet another enlarged view of the illustration of FIG. 17, with the electromechanical surgical instrument coupled to the robotic surgical assembly and with drive transfer shafts of the robotic surgical assembly separated from proximal couplers of the electromechanical surgical instrument.

As illustrated in FIGS. 15 and 16, each portion of the bore 212a of the housing 212 defines a respective longitudinally extending groove or channel 212b therein. Each channel 212b is configured to slidingly accept a rail or tab 350b extending radially from a drive nut 350 of a respective drive assembly 300, as will be described in greater detail below.

The housing 212 further includes ramped camming surfaces 218 disposed on opposed side surfaces thereof for transverse connection/disconnection with the ramp surfaces 176d of the U-shaped body portion 176a of the coupling cuff 176 of the sterile barrier collar assembly 170 (FIG. 13) (e.g., side-loading, described in greater detail below), to connect the electromechanical surgical instrument 200 to the robotic surgical assembly 100. When the electromechanical surgical instrument 200 is fully connected to the robotic surgical assembly 100, the proximal couplers 310 of the drive assemblies 300 of the electromechanical surgical instrument 200 come into registration with and are connected to respective drive transfer shafts 144, 146, 148 and 150 of the drive transfer assembly 140 of the robotic surgical assembly 100.

The housing 212 of the housing assembly 210 of the electromechanical surgical instrument 200 supports an electrical connector 220 (FIG. 13) configured for selective connection to the plug 146 of the drive assembly 140 of the robotic surgical assembly 100, as described above. The electromechanical surgical instrument 200 may include electronics, including, and not limited to, a memory (for storing identification information, usage information, and the like), wired or wireless communication circuitry (for receiving and transmitting data or information from/to the electromechanical surgical instrument 200, from/to control device 4, and/or from/to a remote central processing system). The robotic surgical assembly 100 may be configured to permit passage or routing of a dedicated electrocautery cable or the like for use and connection to an electrosurgical based electromechanical surgical instrument (e.g., for ablation, coagulation, sealing, etc.) The electrical connector 220 may include and is not limited to conductive connectors, magnetic connectors, resistive connectors, capacitive connectors, Hall sensors, reed switches or the like.

With continued reference to FIGS. 13-21A, the housing assembly 210 of the electromechanical surgical instrument 200 includes a plurality of drive assemblies 300. In the illustrated embodiment, the electromechanical surgical instrument 200 includes four drive assemblies 300; however the electromechanical surgical instrument 200 may include more (e.g., five or six) or fewer (e.g., three) drive assemblies 300 without departing from the scope of the present disclosure.

Each drive assembly 300 includes a proximal coupler 310, a proximal bearing 320, a drive screw 340, a drive nut 350, a biasing element 370, and a drive member (e.g., a drive rod or drive cable) 380. The proximal coupler 310 of each drive assembly 300 is configured to meshingly engage with a respective drive coupler 144b, 146b, 148b and 150b of the drive transfer shafts 144, 146, 148 and 150 of the drive transfer assembly 140. In operation, rotation of the drive transfer shafts 144, 146, 148 and 150 of the drive transfer assembly 140, as described above, results in rotation of respective proximal coupler 310 of respective drive assembly 300.

The proximal coupler 310 of each drive assembly 300 is keyed to or otherwise non-rotatably connected to a proximal end of a respective drive screw 340. Accordingly, rotation of the proximal coupler 310 results in a corresponding rotation of a respective drive screw 340.

Each proximal bearing 320 is disposed about a proximal portion of a respective drive screw 340 adjacent a proximal end of the housing 212 of the housing assembly 210. A distal end or tip of each drive screw 340 may be rotatably disposed or supported in a respective recess 212c defined in a distal end of the housing 212 (see FIG. 15).

Figure 14:
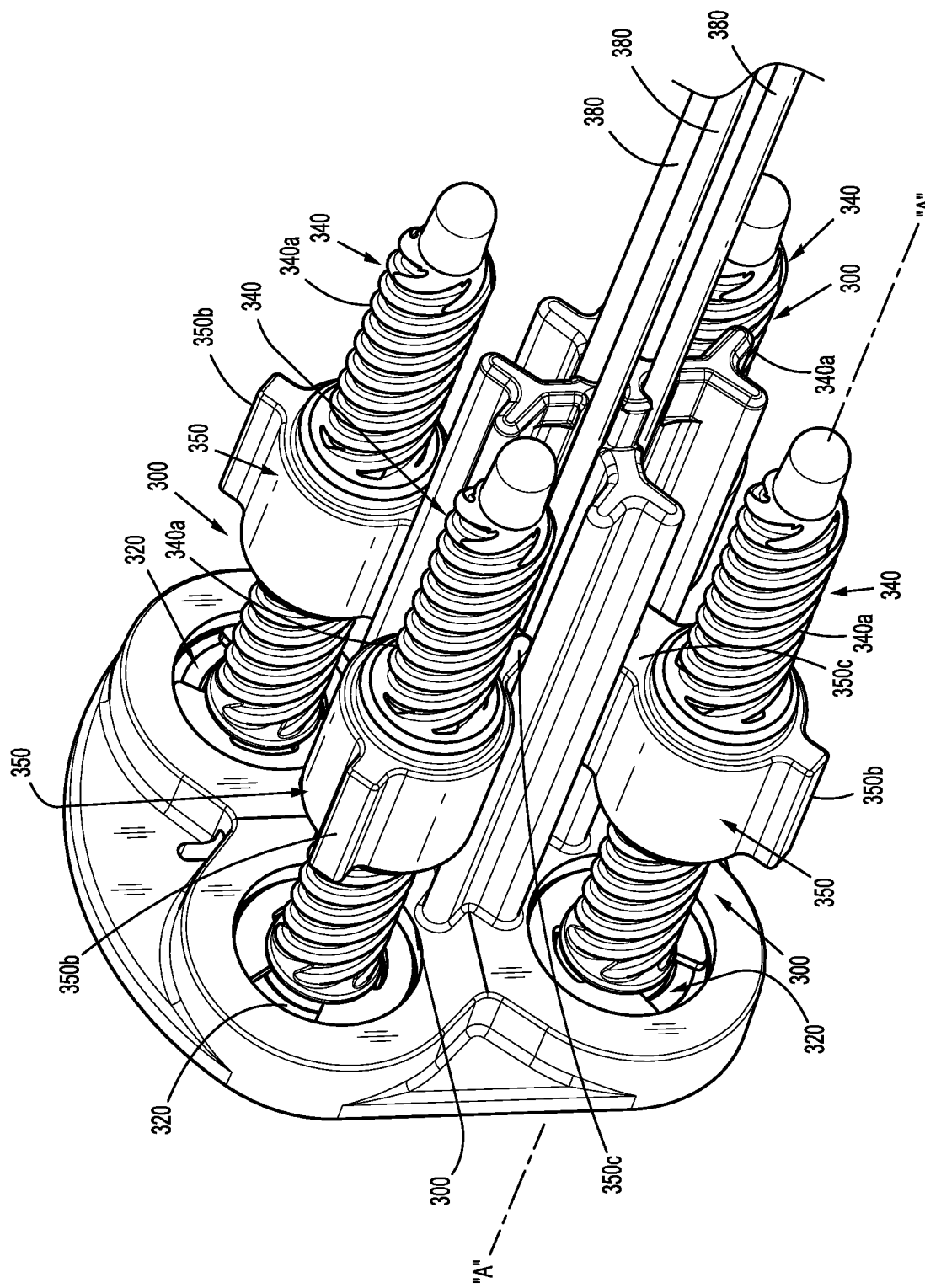
FIG. 14 is a perspective view of a drive assembly of the electromechanical surgical instrument.

The drive screw 340 includes a threaded body or shaft portion 340a, and defines a longitudinal axis "A-A" extending through a radial center thereof (see FIG. 14). In use, rotation of the proximal coupler 310, as described above, results in rotation of a respective drive screw 340 about longitudinal axis "A-A", in a corresponding direction and rate of rotation.

The drive nut 350 (or capstan) includes a threaded aperture 350a extending longitudinally therethrough, which is configured to mechanically engage the threaded shaft portion 340a of the drive screw 340. The drive nut 350 is configured to be positioned on the drive screw 340 in a manner such that rotation of the drive screw 340 causes longitudinal movement of the drive nut 350. That is, the drive nut 350 and the drive screw 340 are threadingly engaged with each other. Moreover, rotation of the proximal coupler 310 in a first direction (e.g., clockwise) causes the drive nut 350 to move in a first longitudinal direction (e.g., proximally) along the drive screw 340, and rotation of the proximal coupler 310 in a second direction (e.g., counterclockwise) causes the drive nut 350 to move in a second longitudinal direction (e.g., distally) with respect to the drive screw 340.

Each drive nut 350 includes a retention pocket formed in an engagement tab 350c formed therein that is disposed adjacent the threaded aperture 350a thereof. Each retention pocket is configured to retain a proximal end 380a of a respective drive member 380, as discussed in further detail below.

Each drive nut 350 includes a tab 350b extending radially from and longitudinally along an outer surface thereof. The tab 350b of each drive nut 350 is configured to be slidably disposed in a longitudinally extending channel 212b formed in the bore 212a of the housing 212. The tab 350b of each drive nut 350 cooperates with a respective channel 212b of the bore 212a of the housing 212 to inhibit or prevent the drive nut 350 from rotating about longitudinal axis "A-A" as the drive screw 340 is rotated.

Each drive nut 350 includes an engagement portion 350c disposed adjacent a radially inward surface thereof, which is configured to mechanically engage or retain a proximal portion 380a of a respective drive member 380. In operation, as the drive nuts 350 are axially displaced along the drive screw 340, the drive nuts 350 transmit concomitant axial translation of the drive member 380.

A biasing element 370, e.g., a compression spring, is configured to radially surround a distal portion of the threaded shaft portion 340a of each drive screw 340. Each biasing element 370 is interposed between a respective drive nut 350 and a distal surface of the housing 212 of the housing assembly 210.

Each drive member 380 extends distally from a respective drive nut 350, through a respective central bore or channel of the housing 212 of the housing assembly 210, and is configured to mechanically engage a portion of a surgical instrument, e.g., end effector, of the electromechanical surgical instrument 200.

In operation, longitudinal translation of at least one drive member 380 is configured to drive a function of the end effector of the electromechanical surgical instrument 200. For example, a distal translation of a particular drive member 380 may be configured to approximate a pair of jaw members of the end effector with respect to the other, and a proximal translation of the same drive member 380 may be configured to move at least one jaw member away from the other jaw member, for instance. Additionally, a distal translation of another drive member 380 of the electromechanical surgical instrument 200 may be configured to articulate the pair of jaw members of the end effector in a first direction, and a proximal translation of the another drive member 380 may be configured to articulate the pair of jaw members of the end effector in a second direction.

In accordance with the present disclosure, a distal portion of at least one of the drive members 380 may include a flexible portion, while a proximal portion of the drive members 380 are rigid, such that the flexible distal portion may follow a particular path through the electromechanical surgical instrument 200. Accordingly, the biasing members 370 function to maintain the drive member 380 in tension to prevent slack or to reduce the amount of slack in the flexible distal portion of the drive member 380.

During a use of the electromechanical surgical instrument 200 (i.e., when motor(s) 52, 54, 56 and 58 of the robotic surgical assembly 100, or other powered drives, are used to rotate proximal couplers(s) 310), rotation of the proximal coupler 310 results in a corresponding rotation of the drive screw 340. Rotation of the drive screw 340 causes longitudinal translation of the drive nut 350 due to the engagement between the threaded portion 340a of the drive screw 340 and the threaded aperture of the drive nut 350. As discussed above, the direction of longitudinal translation of the drive nut 350 is determined by the direction of rotation of the proximal coupler 310, and thus, the drive screw 340. For example, proximal translation of the drive screw 340 results in a corresponding proximal translation of a respective drive member 380 which is engaged with the drive screw 340.

Additionally, when one drive nut 350, from a first drive assembly 300, moves in a first longitudinal direction (e.g., proximally), it is envisioned that a drive nut 350, from a different drive assembly 300, is forced to correspondingly move in a second, opposite longitudinal direction (e.g., distally). Such configurations function to compensate for any slack in the drive members 380. It is contemplated and in accordance with the present disclosure that each drive nut 350 may be independently driven.

While end effectors have been described in here as including a jaw assembly, the use of other end effectors are additionally or alternatively possible. Reference may be made to commonly owned International Patent Application No. PCT/US14/61329, filed on Oct. 20, 2014 entitled "Wrist and Jaw Assemblies for Robotic Surgical Systems," the entire contents of which are incorporated herein by reference, for a detailed discussion of illustrative examples of the construction and operation of end effectors for use with or connection to electromechanical surgical instrument 200.

Figure 13:
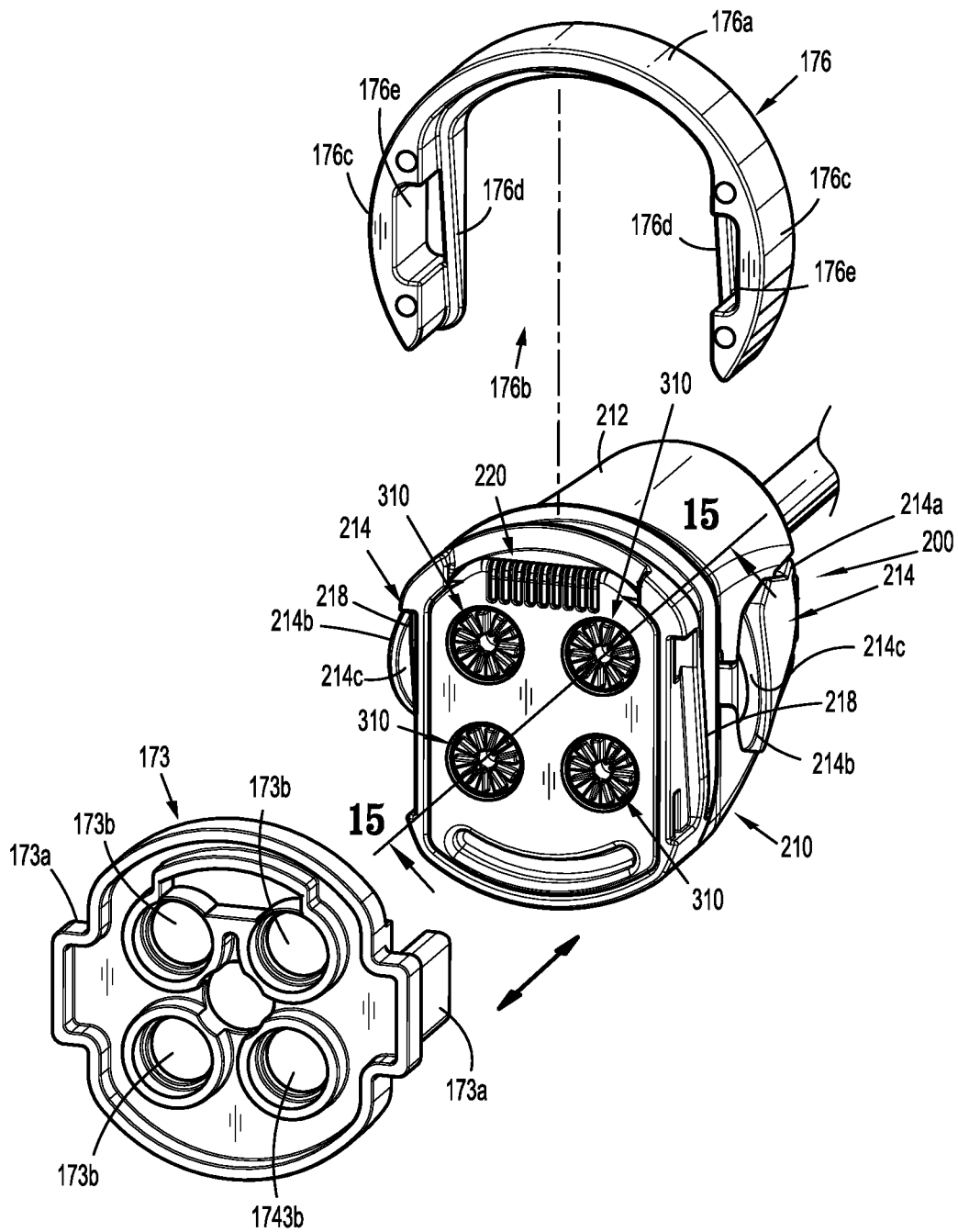
FIG. 13 is a perspective view, with parts separated, of the electromechanical surgical instrument, and a floating plate and a coupling cuff of the sterile barrier collar assembly of FIG. 9.
Figure 35:
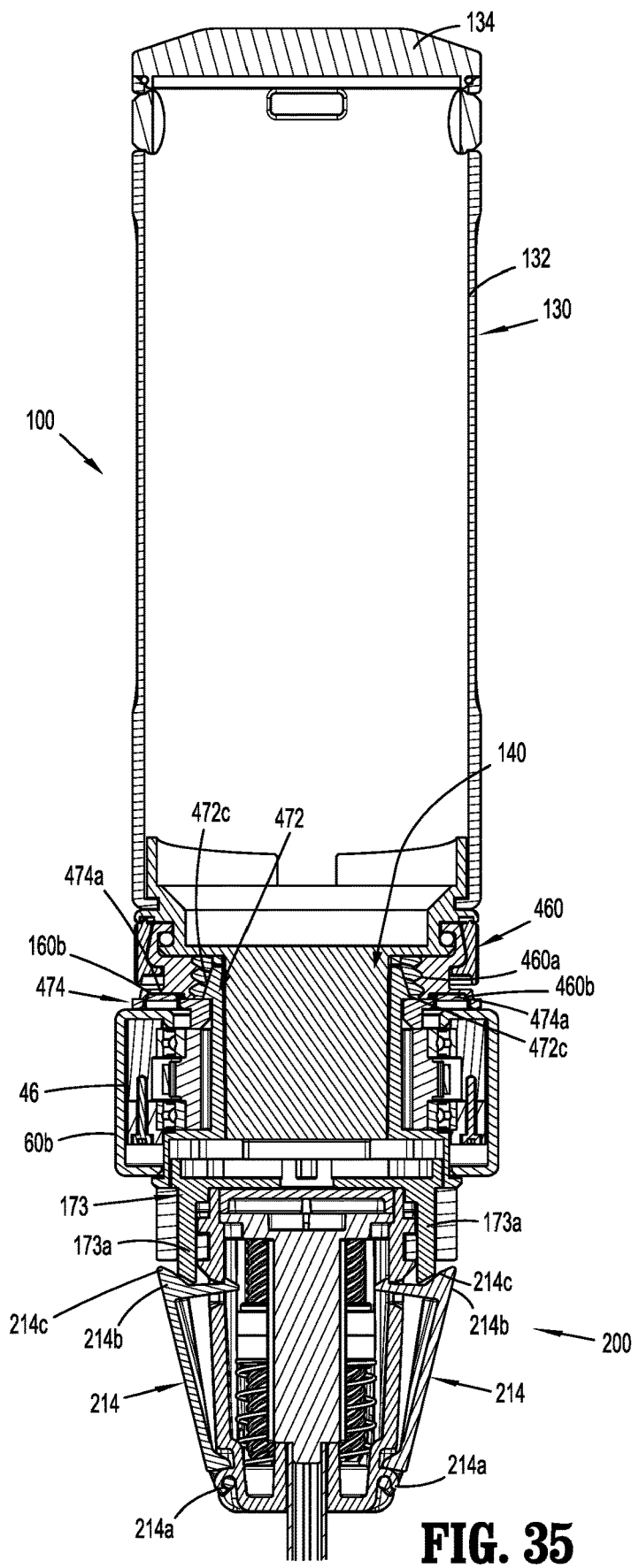
FIG. 35 is an enlarged view of the indicated area of detail of FIG. 34.
Figure 38:
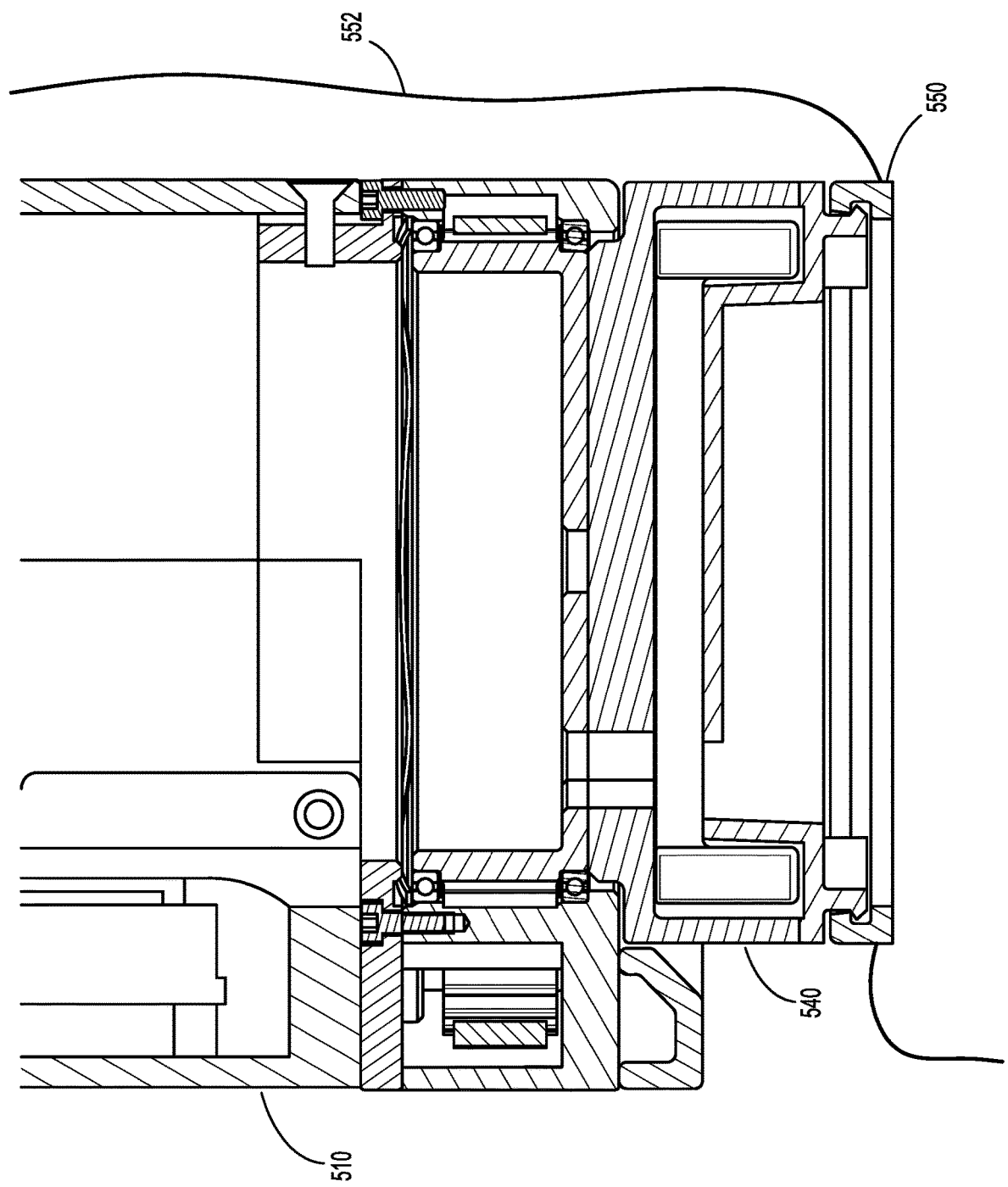
FIG. 38 is an enlarged, partial, cross-sectional view of a portion of the robotic surgical assembly of FIG. 1.
Figure 39:
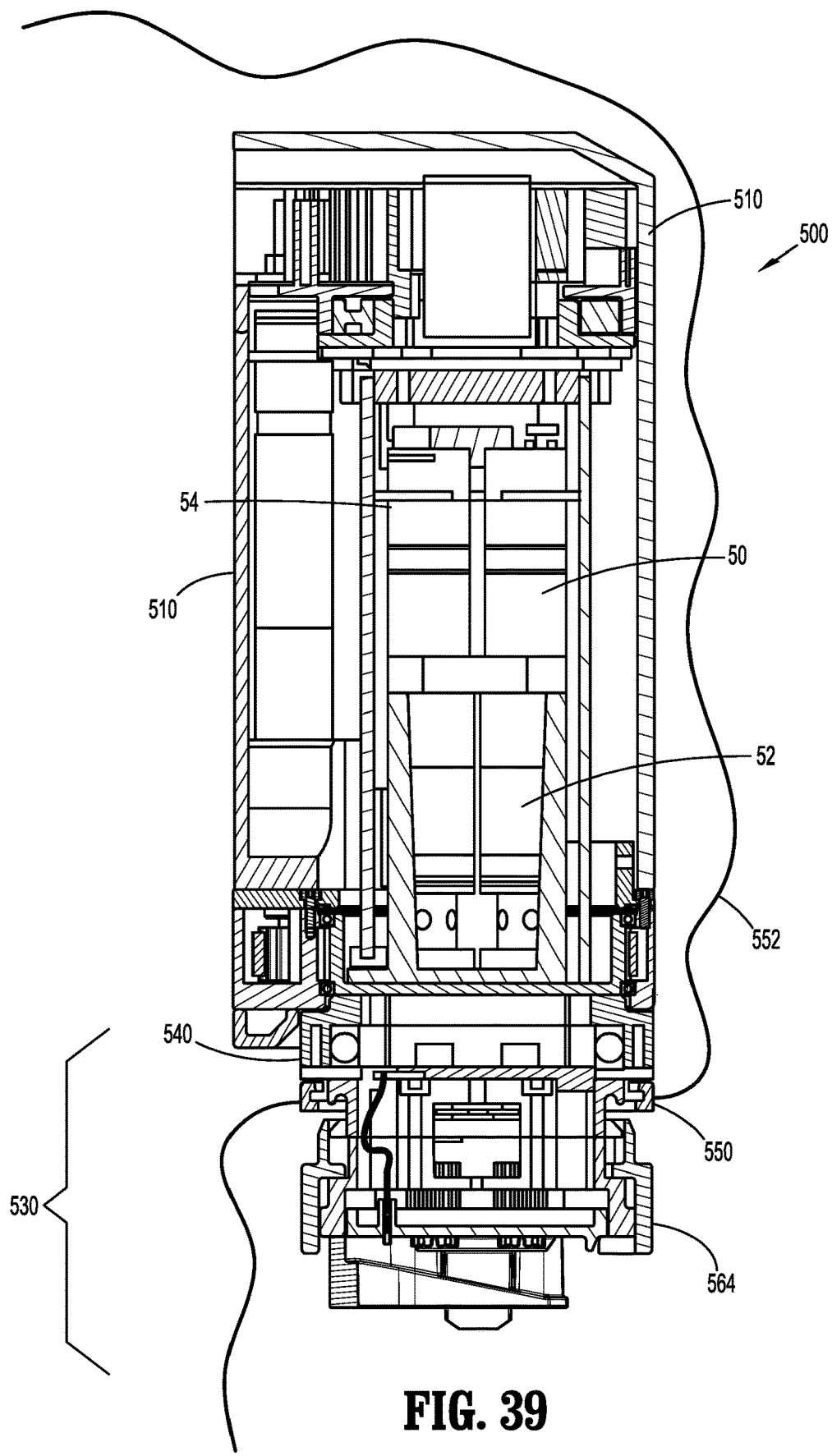
FIG. 39 is an enlarged, side, cross-sectional view of the robotic surgical assembly of FIG. 1 with a sterile interface module thereof shown in a first position.

With reference to FIGS. 13, 21 and 35, the housing 212 of the housing assembly 210 of the electromechanical surgical instrument 200 supports at least one, desirably a pair of release levers or paddles 214 on opposed sides thereof. Each release paddle 214 includes a first end 214a pivotally connected to the housing 212, and a second end 214b movable to/from an outer surface of the housing 212. The second end 214b of each release paddle 214 defines a tapered camming surface 214c configured to act on a respective arm or tab 173a of the distal floating plate 173 of the sterile barrier collar assembly 170, to disengage the electromechanical surgical instrument 200 from the robotic surgical assembly 100. Specifically, when the electromechanical surgical instrument 200 is connected to semiannular coupling cuff 176 of the sterile barrier collar assembly 170, arms or tabs 173a of the distal floating plate 173 are aligned and in registration with respective paddles 214 of the electromechanical surgical instrument 200. Further, the free ends of the arms or tabs 173a of the distal floating plate 173 act on respective tapered camming surfaces 214c of the paddles 214 to press or urge the paddles 214 outwardly.

With continued reference to FIGS. 13, 21A, and 35, a connection of the electromechanical surgical instrument 200 to the robotic surgical assembly 100 is shown and will be described. Initially, as described briefly above, the sterile barrier collar assembly 170 is connected to the annular shell 60b of the shell 60, the motor pack 50 is loaded in the cavity 132a of the body 132 of the sterile barrier housing 130, and the drive transfer assembly 140 of the sterile barrier housing 130 of the robotic surgical assembly 100 is connected to the shell 60.

Figure 21B:
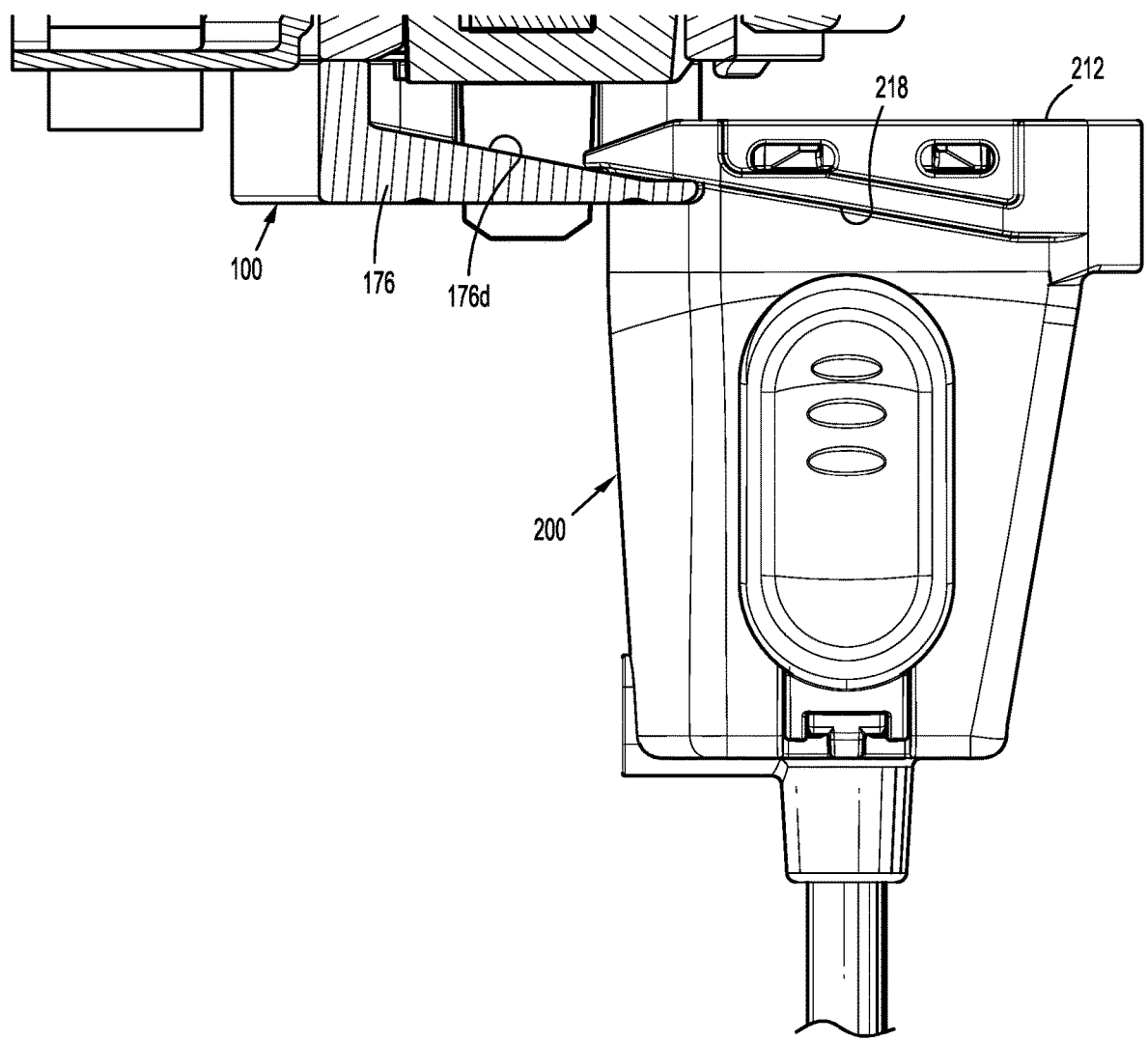
FIGS. 21B-21D are progressive views illustrating the electromechanical surgical instrument being coupled to the robotic surgical assembly.
Figure 21C:
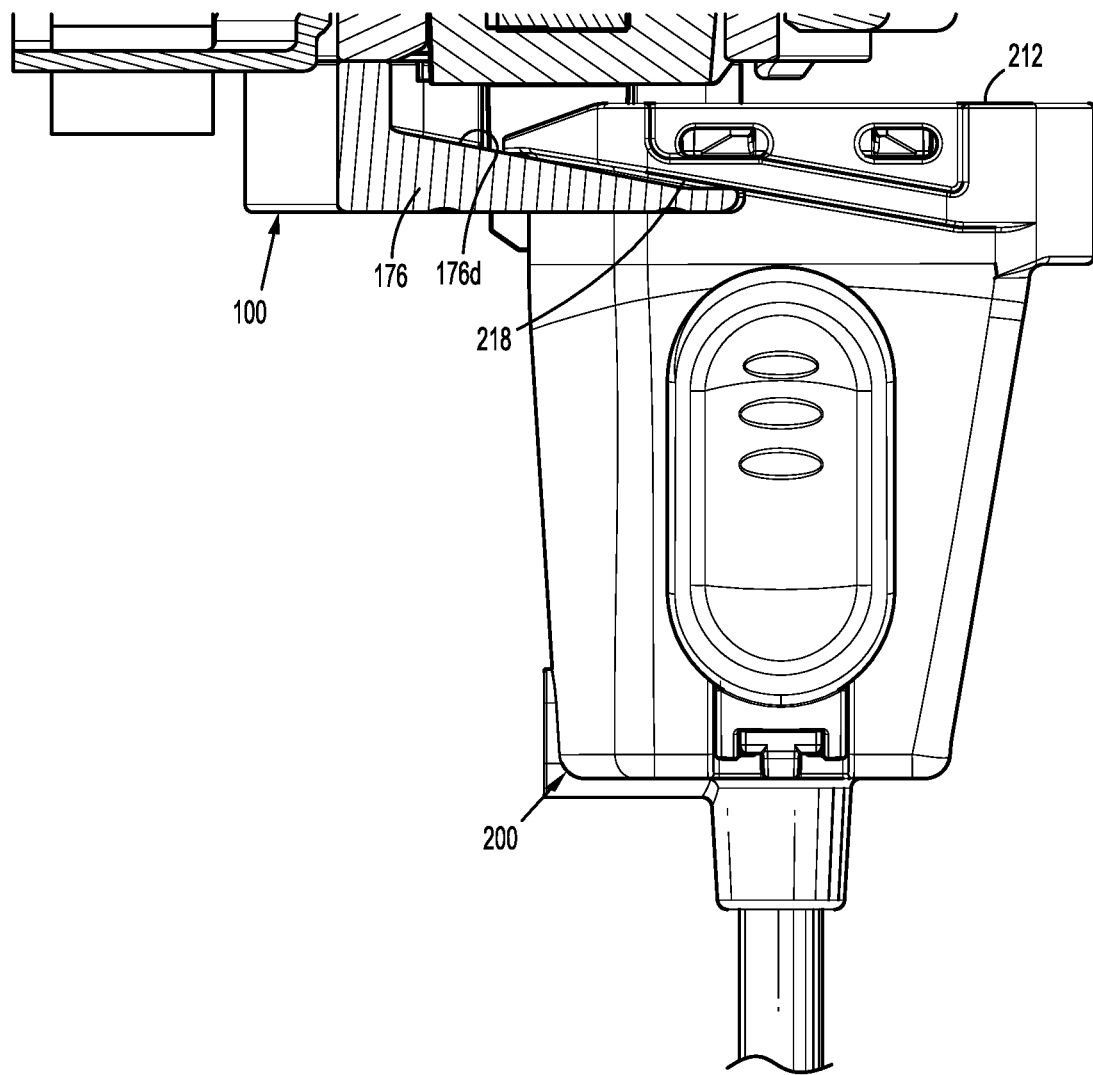
Figure 21D:
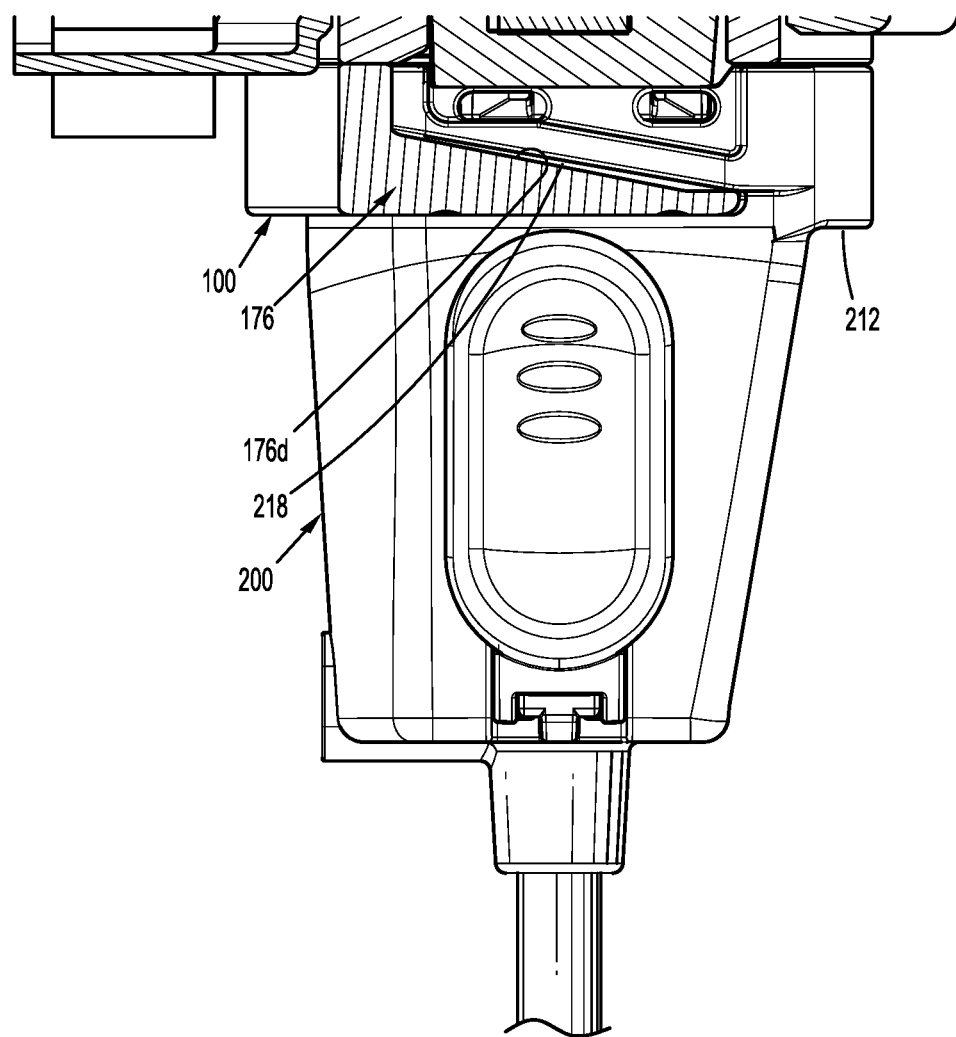

The electromechanical surgical instrument 200 is then connected to the coupling cuff 176 of the sterile barrier collar assembly 170 by first aligning the ramped camming surfaces 218 of the housing 212 of the electromechanical surgical instrument 200 with the corresponding ramp surface 176d of the coupling cuff 176. As seen in FIGS. 21B-21D, the electromechanical surgical instrument 200 is then transversely moved (e.g., side loaded) relative to the robotic surgical assembly 100 such that the ramped camming surfaces 218 of the electromechanical surgical instrument 200 cams the electromechanical surgical instrument 200 upwardly (proximally) along the ramp surface 176d of the coupling cuff 176 until the housing 212 of the electromechanical surgical instrument 200 is fully received or seated in the coupling cuff 176.

As the electromechanical surgical instrument 200 is transversely moved into the coupling cuff 176, as described above, the housing 212 is urged upwardly (proximally) into contact with inner shoulders 173c, 173d (FIG. 21A) of the distal floating plate 173 to urge the distal floating plate 173 proximally against the distal spring bias of the distal floating plate 173. Also, when the electromechanical surgical instrument 200 is properly connected to the robotic surgical assembly 100, the proximal couplers 310 of the electromechanical surgical instrument 200 come into registration with (e.g., spring biased) and are connected to respective drive transfer shafts 144, 146, 148 and 150 of the drive transfer assembly 140 of the robotic surgical assembly 100.

Figure 20:
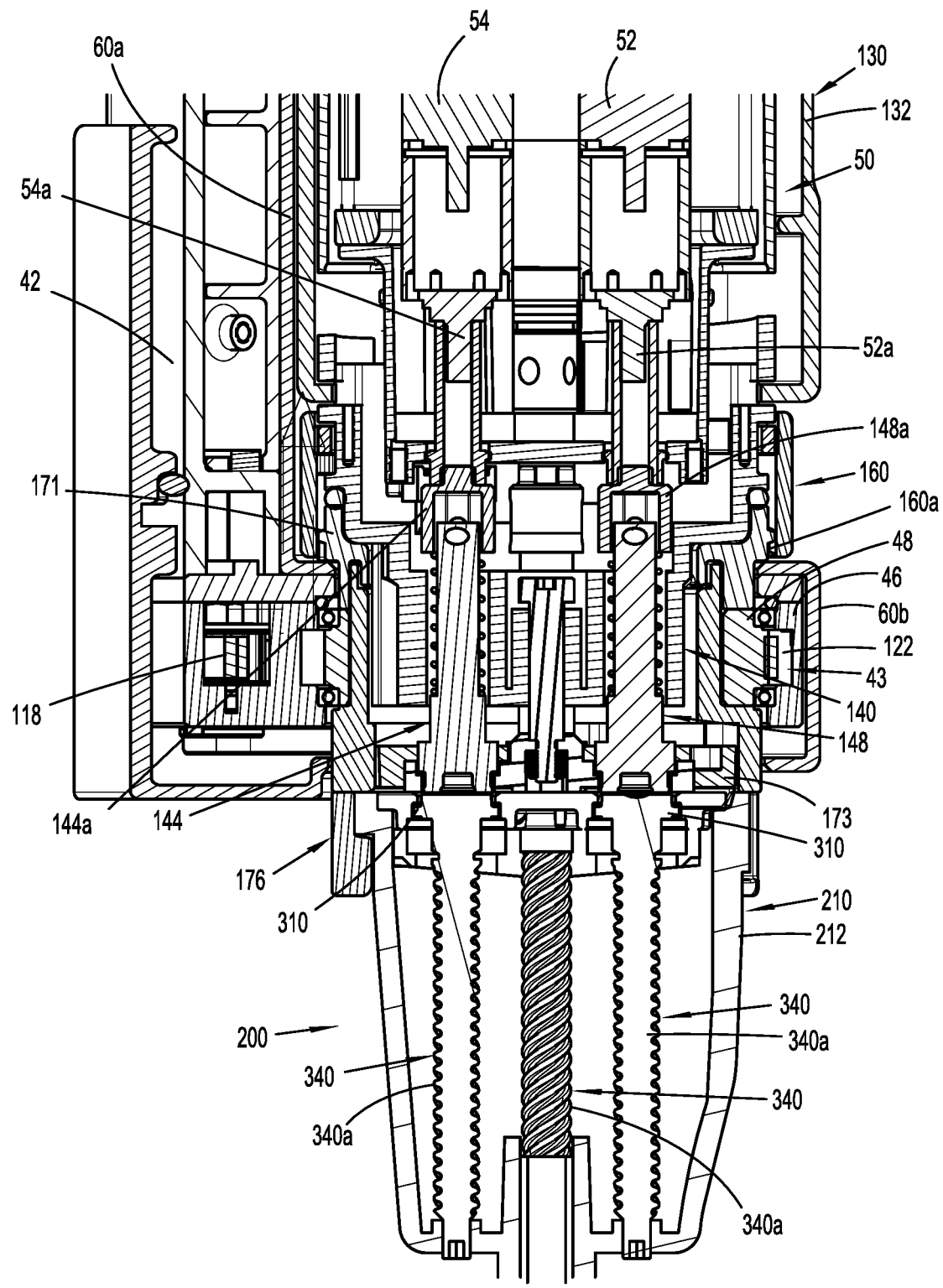
FIG. 20 is still another enlarged view of the illustration of FIG. 17, with the electromechanical surgical instrument coupled to the robotic surgical assembly and with the drive transfer shafts of the robotic surgical assembly coupled to the proximal couplers of the electromechanical surgical instrument.

Disconnection of the electromechanical surgical instrument 200 from the robotic surgical assembly 100 includes pressing the paddles 214 of the electromechanical surgical instrument 200 toward the housing 212 whereby the tapered camming surfaces 214c of the paddles 214 act on the free ends of the arms or tabs 173a of the distal floating plate 173. As the paddles 214 act on the free ends of the arms or tabs 173a, the paddles 214 urge the distal floating plate 173 proximally, whereby the drive couplers 144b, 146b, 148b and 150b of the drive transfer shaft 144, 146, 148 and 150 are urged proximally, against the bias of respective biasing members 144d, 146d, 148d and 150d, to separate or disengage the drive couplers 144b, 146b, 148b and 150b from respective proximal gears or couplers 310 of the electromechanical surgical instrument 200 (FIG. 20). Thereafter, the electromechanical surgical instrument 200 may be transversely removed or disconnected from the robotic surgical assembly 100.

As illustrated in FIG. 21A, the tubular sleeve body 172 of the sterile barrier collar assembly 170 includes a pair of opposed deflectable fingers 172b extending in an axial direction. Each finger 172b terminates in a free end having an outer angled surface 172c extending radially outward, and an inner angled surface 172d extending radially outward. Further, the proximal ring connector 171 defines an inner annular, angled surface 171a oriented at an angle complementary to the outer angled surface 172c of the tubular sleeve body 172. Also, a distal nose of the sterile barrier housing 130 defines an outer annular, angled surface 130a oriented at an angle complementary to the inner angled surface 172d of the tubular sleeve body 172.

In use, with the tubular sleeve body 172 snapped into the proximal ring collar 171, the proximal ring collar 171 is connected to the lock ring collar 160 by inserting a proximal end of the proximal ring collar 171 into the lock ring collar 160 and rotating the lock ring collar 160 to draw-in and threadably connect with the proximal ring collar 171. As the lock ring collar 160 is rotated to draw-in the proximal ring collar 171, the inner annular, angled surface 171a of the proximal ring collar 171 acts on the outer angled surface 172c of the deflectable fingers 172b of the tubular sleeve body 172 to pinch or trap the deflectable fingers 172b of the tubular sleeve body 172 against the outer annular, angled surface 130a of the distal nose of the sterile barrier housing 130. In this manner, tightening rotation of lock ring collar 160 approximates drive transfer assembly 140 and proximal ring collar 171 and mates drive transfer assembly 140 to tubular sleeve body 172

With continued reference to FIG. 21A, a sealing member 177, in the form of an O-ring, gasket or the like, may be interposed between an outer annular flange of outer housing portion 130 and a proximal ledge or surface of the proximal ring collar 171.

Turning now to FIGS. 22-35, a lock ring or collar according to another embodiment of the present disclosure is shown and described, and is generally designated as the lock ring or collar 460. Additionally, as shown in FIGS. 22-35, a sterile barrier collar assembly according to another embodiment of the present disclosure is shown and described, and is generally designated as sterile barrier collar assembly 470. In FIGS. 22-35, like reference numerals have been used to identify like parts as in FIGS. 1-21A. Also, in the interest of brevity, only the differences between the robotic surgical assembly 100 having the lock ring or collar 160 and the sterile barrier collar assembly 170 (FIGS. 1-21A) and the robotic surgical assembly 100 having the lock ring or collar 460 and the sterile barrier collar assembly 470 (FIGS. 22-35), will be described in detail herein below.

As illustrated in FIGS. 21A-35, the robotic surgical assembly 100 may include the lock ring or collar 460 rotatably supported on the distal end of the body 132 of the sterile barrier housing 130. The lock collar 460 projects distally from the body 132 of the sterile barrier housing 130, and defines an internal thread 460a (see FIGS. 33 and 35, 27) configured for threadable connection to a sterile barrier collar assembly 470. A distal-most surface of the lock collar 460 defines a series of notches or recesses 460b therein. The recesses 460b may extend radially around the distal-most surface of the lock collar 460. The recesses 460b may include four sets of three recesses, with one set of recesses located 90° apart (or substantially 90° apart) from one another.

The robotic surgical assembly 100 may further include a sterile barrier collar assembly 470 connectable to the annular shell 60b of the shell 60 and extendable through the D-shaped passage or opening 48a of the pulley 48 (see FIGS. 26 and 27). Specifically, the sterile barrier collar assembly 470 includes a tubular sleeve body 172 having a non-circular, transverse cross-sectional outer profile (e.g., substantially D-shaped, or the like), and an inner bore 472a having a complementary, non-circular, transverse cross-sectional profile (e.g., substantially D-shaped, or the like). An outer surface of a proximal portion of tubular sleeve body 472 defines a thread 472b therein, wherein the thread 472b is formed in at least one radial portion of the tubular sleeve body 472. The proximal portion of the tubular sleeve body 472 includes a pair of opposed, deflectable tabs 472c projecting radially outward, and increasing in height from a proximal end to a distal end thereof.

The sterile barrier collar assembly 470 further includes a ring flange 474 supported on the tubular sleeve body 472. The ring flange 474 extends radially outward from the tubular sleeve body 472. The ring flange 474 includes a pair of opposed, deflectable tabs 474a projecting from a proximal surface of the ring flange 474. The deflectable tabs 474a of the ring flange 474 are configured for selective receipt in the recesses 460b formed in the lock collar 460. As collar 460 is rotated to secure the electromechanical surgical instrument 200 to the robotic surgical assembly 100, a tactile and/or audible feedback is provided between the deflectable tabs 474a of the ring flange 474 and the recesses 460b of the lock collar 460 to provide an indication that the electromechanical surgical instrument 200 is secured to the robotic surgical assembly 100.

It is contemplated that a sheet of polymeric material, constituting a drape or the like (not shown), may be sandwiched or captured (or bonded, elastically mated, or snap latched) between the distal-most surface of the lock collar 460 of the sterile barrier housing 130 and the proximal surface of the ring flange 474 of the sterile barrier collar assembly 470. The drape may be extended over the sterile barrier housing 130, over the rail 40 and over the robotic arms 2, 3.

With reference to FIG. 36, one embodiment of a robotic surgical system includes a robotic surgical assembly 500 having four independently-controlled motors 52, 54, 56 and 58, and an electromechanical surgical instrument 250 including a drive system 256 having four drive assemblies 256a-256d, with each drive assembly selectively connectable to the respective motor 52, 54, 56 and 58 of the robotic surgical assembly 500, for example, as described above with respect to robotic surgical assembly 100. The electromechanical surgical instrument 250 is similar to electrosurgical instrument 200 and is described herein only to the extent necessary to describe the differences in construction and operation thereof.

The electromechanical surgical instrument 250 includes an end effector 252 (shown in FIG. 36 in an open position) selectively supported on a distal end thereof and an instrument housing 253 supported on a proximal end thereof. While the end effector 252 may include a jaw assembly or the like, the use of other end effectors are additionally or alternatively possible. Reference may be made to commonly owned International Patent Application No. PCT/US14/61329, filed on Oct. 20, 2014 entitled "Wrist and Jaw Assemblies for Robotic Surgical Systems," U.S. Pat. No. 8,636,192, or U.S. Pat. No. 8,925,786, the entire contents of each of which are incorporated by reference herein, for a detailed discussion of illustrative examples of the construction and operation of end effectors for use with or connection to the electromechanical surgical instrument 250.

Figure 47:
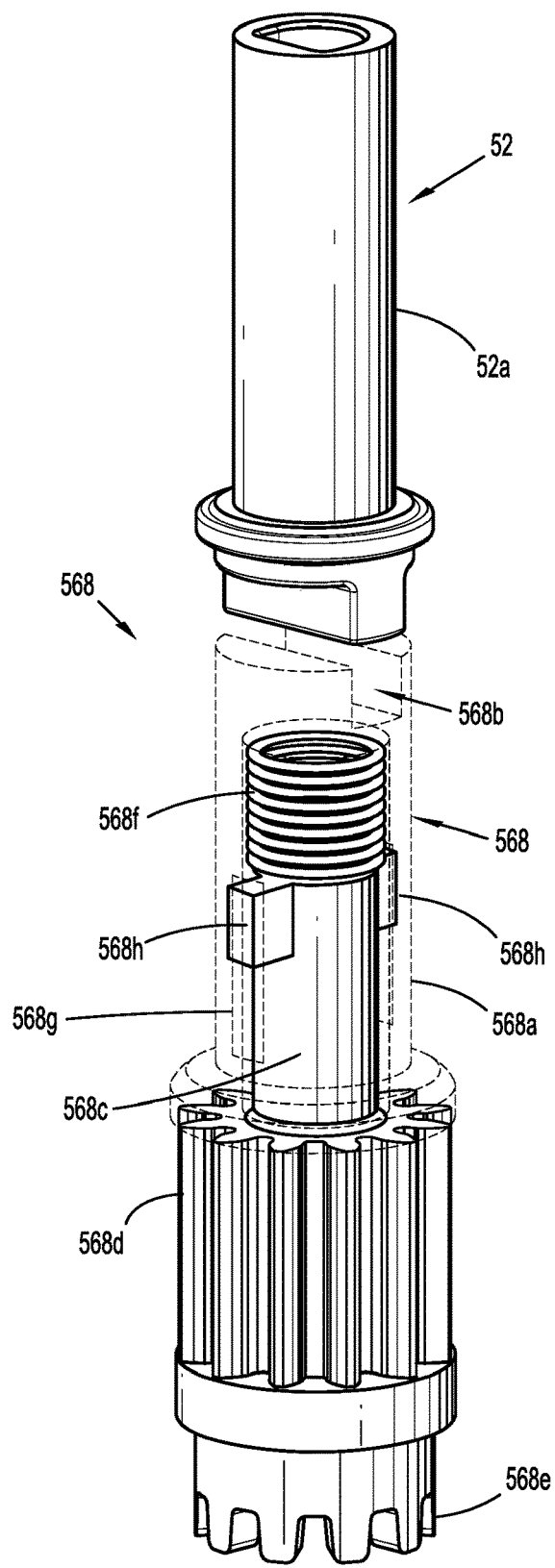
FIG. 47 is a perspective view of the drive transfer assembly and the motor coupler of FIG. 46 with the drive transfer assembly shown in a second state.
Figure 48:
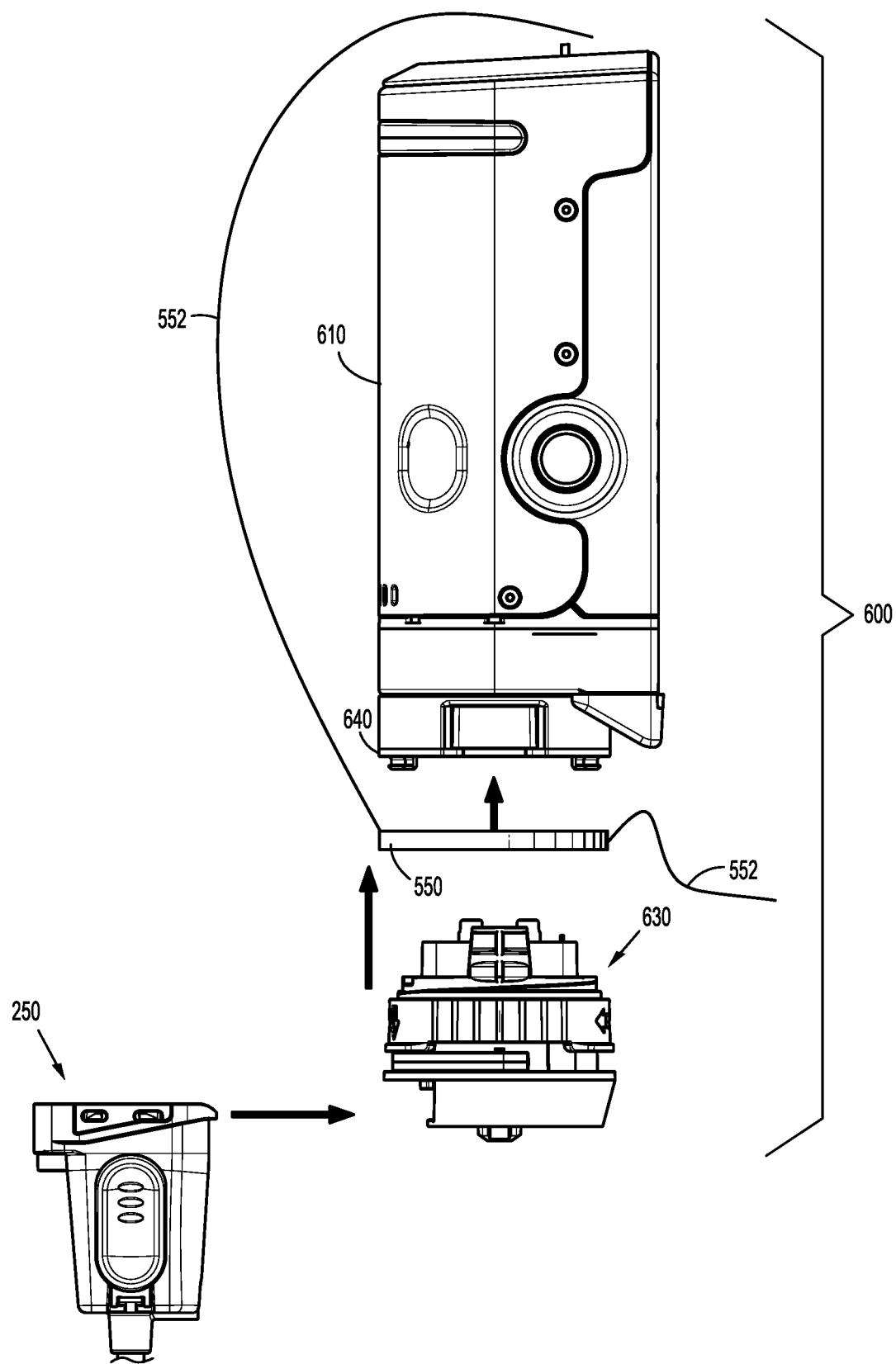
FIG. 48 is a side, elevational view, with parts separated, of yet another embodiment of a robotic surgical assembly according to the present disclosure.

The instrument housing 253 supports a detachment assembly 254 and a drive assembly 256. The detachment assembly 254 includes release levers or paddles 254a, 254b on opposed sides of the instrument housing 253 and which are operable to selectively separate the electromechanical surgical instrument 250 from the robotic surgical assembly 500. Each paddle 254a, 254b may include tapered camming surfaces (not shown) configured to act on tabs 566b, 566c of a floating plate 566 of a sterile interface module 530 to disengage the electromechanical surgical instrument 250 from the robotic surgical assembly 500 as described in greater detail below (see FIG. 43). The drive system 256 includes a first drive assembly 256a and second drive assemblies 256b, 256c, 256d that cooperate with one or more drive or connector members "CM," such as drive cables or drive rods, coupled to the end effector 252 of the electromechanical surgical instrument 250 to manipulate and/or operate the end effector 252. Each of the first and second drive assemblies 256a-256d includes an engagement coupler 258 (e.g., a gear or the like) engagable with complementary instrument engagement ends or couplers (such as engagement couplers 568e shown in FIG. 47) of the robotic surgical assembly 500 described in greater detail below.

As mentioned above, the robotic surgical system 1 is configured for use on a patient "P" positioned (e.g., lying) on a surgical table "ST" to be treated in a minimally invasive manner by means of a surgical instrument, e.g., any one of the electromechanical surgical instruments such as straight/articulatable instruments 200 and 250 (e.g., stapling instrument, suturing instrument, electrocautery instrument, etc.), endoscope 250' or grasper 250" (FIG. 36). The robotic surgical system 1 may include more than two robotic arms 2, 3, the additional robotic arms likewise being connected to the control device 4 and telemanipulatable by means of the operating console 5. A surgical instrument, for example, any one or more of electromechanical surgical instruments 200 (FIG. 2), 250, 250', and/or 250" may also be attached to the additional robotic arm.

As mentioned above, the motor pack 50 may include four motors (e.g., canister motors or the like with non-circular drive shafts) arranged in a formation so that each of the four motors extends in a common direction and are in parallel with one another so as to interface with any one of the electromechanical surgical instruments 200 (FIG. 2), 250, 250', and/or 250".

In general, the robotic surgical assembly 500 transfers power and actuation forces from one or more of its motors 52, 54 to one or more of respective driven members/drive assemblies 256a-256d of the electromechanical surgical instrument 250 (e.g., keyed together via an "oldham coupling" arrangement or the like for transmitting rotational and/or axial forces between the robotic surgical assembly 500 and the electromechanical surgical instrument 250) to ultimately drive movement of one or more components of the end effector 252 of electromechanical surgical instrument 250. For example, the transfer of power/forces from the robotic surgical assembly 500 to the electromechanical surgical instrument 250 effectuates a movement of a knife blade (not shown), a closing and opening of jaw members of the end effector 252, an actuation or firing of a stapler, an activation or firing of an electrosurgical energy-based instrument, and/or other functions thereof.

For a detailed discussion of the construction and operation of a similar robotic surgical system having one or more of the same or similar components for use with one or more components of the presently described robotic surgical system, reference may also be made to U.S. Patent Application Publication No. 2012/0116416, filed on Nov. 3, 2011, entitled "Medical Workstation," the entire contents of which are incorporated by reference herein.

Turning now to FIGS. 36-47, the robotic surgical assembly 500 of the robotic surgical system 1 includes an instrument drive unit or housing 510 supporting a motor assembly or motor pack 50. The housing 510 of the robotic surgical assembly 500 includes a connector assembly 540.

A ring member 550 having a sterile drape 552 secured thereto is provided, wherein the ring member 550 permits passage of rotational forces from the motor pack 50, and wherein the sterile drape 552 is configured to overlie the robotic surgical assembly 500 and the robotic arms 2, 3. The ring member 550 is configured for rotatable attachment to a distal end of the connector assembly 540 (e.g., via snap fit). The sterile drape 552 can be arranged as desired above about the housing 510, the robotic surgical assembly 500 and the robotic arms 2, 3 to provide a sterile barrier between the various aforementioned components and/or the surgical site/fluids and the electromechanical surgical instruments 200 (FIG. 2), 250, 250', and/or 250".

A collar assembly or sterile interface module 530 is provided for selectively interconnecting the robotic surgical assembly 500 and any one of the electromechanical surgical instruments 200 (FIG. 2), 250, 250', and/or 250" similar to that described above with respect to the coupling of the electromechanical surgical instrument 200 to robotic surgical assembly 100 (e.g., side-loading). In general, sterile interface module 530 functions to provide an interface between the instrument drive unit or housing 510 and an electromechanical surgical instrument such as electromechanical surgical instrument 250. This interface advantageously maintains sterility, provides a means to transmit electrical communication between the robotic surgical assembly 500 and the electromechanical surgical instruments, provides a means for transferring rotational force from the robotic surgical assembly 500 to the electromechanical surgical instruments for performing a function with the electromechanical surgical instruments, and/or provides a means to selectively attach/remove electromechanical surgical instruments to the robotic surgical assembly 500 (e.g., for rapid instrument exchange).

The motor assembly 50 of the robotic surgical assembly 500 includes any number of motors 52, 54 (e.g., 2, 3, 4, 5, etc.) that couple to the sterile interface module 530 via a corresponding number of motor couplers 52*b*, 54*b* (see FIG. 41) extending from the motors 52, 54.

Figure 40:
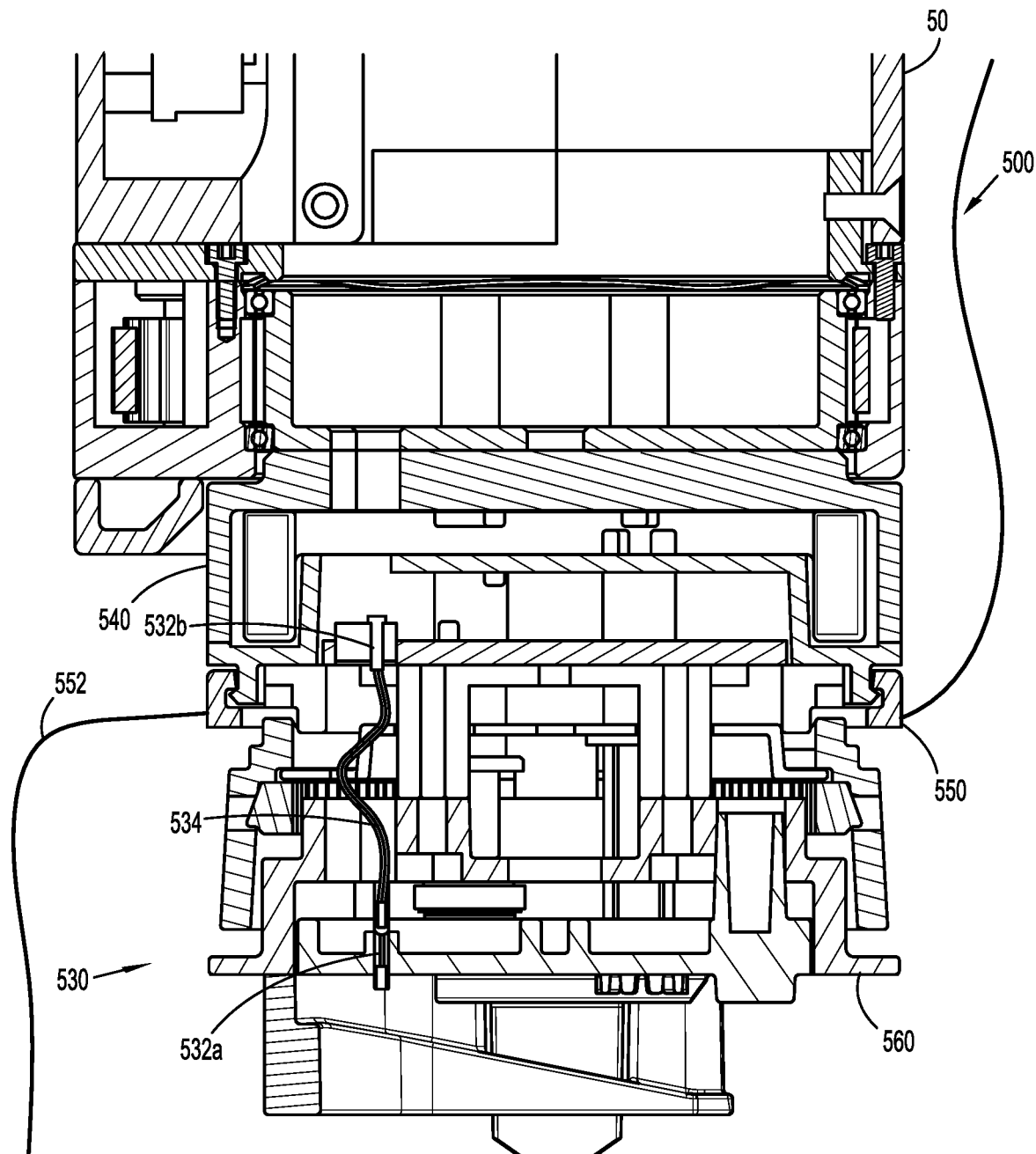
FIG. 40 is an enlarged, side, cross-sectional view of a portion of the robotic surgical assembly of FIG. 1 with the sterile interface module thereof shown in a second position.

As seen in FIG. 40, the collar assembly or sterile interface module 530 includes electrical connectors 532*a*, 532*b* and an electrical ribbon 534 coupled between the electrical connectors 532*a*, 532*b* to provide electrical communication between the robotic surgical assembly 500 and any electromechanical surgical instrument, such as electromechanical surgical instrument 250, coupled thereto.

With reference to FIGS. 41-45, the sterile interface module 530 includes a body member 562 having an upper portion 562*a*, an intermediate portion 562*b*, and a lower portion 562*c*. The upper portion 562*a* of the body member 562 defines a helical channel 562*d* that extends around the upper portion 562*a* from a shoulder 562*e* of the upper portion 562*a*. The upper portion 562*a* further includes a pair of attachment arms 562*f*, 562*g* that extend proximally from the upper portion 562*a* to secure the sterile interface module 530 to the connector assembly 540 of the housing 510 of the robotic surgical assembly 500. The pair of attachment arms 562*f*, 562*g* may be disposed in mirrored relation on opposed sides of the upper portion 562*a*.

The intermediate portion 562*b* of the body member 562 includes a flange 562*h* and rotatably supports a rotatable collar 564 thereon. The rotatable collar 564 of the sterile interface module 530 defines a helical channel 564*a* that extends from a shoulder 564*b* of the rotatable collar 564. The helical channel 564*a* of the rotatable collar 564 and the shoulder 564*b* of the rotatable collar 564 complement the helical channel 562*d* of the upper portion 562*a* of the body member 562 and the shoulder 562*e* of the upper portion 562*a* of the body member 562. The rotatable collar 564 further includes gripping grooves 564*c* to facilitate user gripping and/or rotation of the rotatable collar 564 relative to the body member 562 of the sterile interface module 530, as indicated by arrow "A" (described in greater detail below).

The lower portion 562*c* of the body member 562 of the sterile interface module 530 is in the form of a semi-annular coupling cuff that is supported on or otherwise secured to a distal end of the intermediate portion 562*b* of the body member 562. The lower portion 562*c* of the body member 562 includes a U-shaped body having an instrument opening 562*i* defined between side arms 562*j*, 562*k* and opening distally and laterally. The lower portion 562*c* further includes a ramped surface 562*x* (FIG. 41) formed on an inner surface thereof that complements the ramped camming surfaces 218 of the housing 212 of the electromechanical surgical instrument 250. The instrument opening 562*i* is configured to receive an electromechanical surgical instrument, such as electromechanical surgical instrument 250, therein to removably secure the electromechanical surgical instrument 250 to the robotic surgical assembly 500. The side arms 562*j*, 562*k* of the lower portion 562*c* extend distally from the intermediate portion 562*b* of the body member 562 and are positioned to support the electromechanical surgical instrument 250 within the instrument opening 562*i* of the lower portion 562*c*.

Similar to distal floating plate 173 described above with respect to the robotic surgical assembly 100, the sterile interface module 530 further includes a floating plate 566 supported between the intermediate portion 562*b* of the body member 562 and the lower portion 562*c* of the body member 562. The floating plate 566 of the sterile interface module is movable between an uncompressed position or extended position and a compressed or retracted position. The floating plate 566 is spring biased distally toward the uncompressed position by a round spring (e.g., a wave spring, not shown) and by biasing members of drive transfer assemblies (e.g., 568, 570) of the sterile interface module 530. In the uncompressed position of the floating plate 566 of the sterile interface module 530, the floating plate 566 is spaced a distance "D" (see FIG. 43) from a bottom surface 562*e* of the intermediate portion 562*b*. The floating plate 566 includes a base portion 566 and tabs 566*b*, 566*c* extending distally from the base portion 566. The tabs 566*b*, 566*c* extend through the lower portion 562*c* of the body member 562. The floating plate 566 defines apertures 566*d*, 566*e* therein that receive first and second drive transfer assemblies 568, 570 of the sterile interface module 530. While a pair of drive transfer assemblies 568, 570 are shown and described in detail herein, any number of drive transfer assemblies may be provided, such as, for example, one, three, five, etc.

With reference to FIGS. 43-47, the first and second drive transfer assemblies 568, 570 of the sterile interface module 530 include respective drive couplers 568*a*, 570*a* defining coupling ends 568*b*, 570*b* engagable with coupling ends 56 of respective motor couplers 52*b*, 54*b* of the motor assembly 50. The first drive transfer assembly 568 includes a transfer shaft 568*c* and the second drive transfer assembly 570 includes a transfer shaft 570*c*. The transfer shafts 568*c*, 570*c* of the respective first and second drive transfer assemblies 568, 570 extend to a respective instrument engagement end or coupler 568*e*, 570*e* (e.g., a gear or the like with distally extending teeth) at a distal end thereof.

It is contemplated that the transfer shaft 568*c* of the first drive transfer assembly 568 may further support a drive coupler 568*d* thereon that is disposed proximal of the instrument engagement coupler 568*e* of the transfer shaft 568*c*.

A respective biasing member or spring 568f (the biasing member of the second drive transfer assembly 570 not being shown) is supported between the drive couplers 568a, 570a and the transfer shafts 568c, 570c of each of the respective first and second drive transfer assemblies 568, 570 such that each spring 568f is configured to apply spring force to its respective first or second drive transfer assembly 568, 570 upon compression thereof. The biasing members of the drive transfer assemblies 568, 570 may be compression springs. The drive couplers 568a, 570a of the first and second drive transfer assemblies 568, 570 define side slots 568g, 570g therein that slidably receive wings 568h (the wings of the second drive transfer assembly 570 not being shown) extending from the transfer shafts 568c, 570c of the first and second drive transfer assemblies 568, 570. The wings 568h of the transfer shafts 568c, 570c are configured to slide through the side slots 568g, 570g of the first and second drive transfer assemblies 568, 570 in response to relative movement between one of the transfer shafts 568c, 570c and its respective drive coupler 568a, 570a. In this regard, the drive couplers 568a, 570a of the drive transfer assemblies 568, 570 provide coupling in the manner of an "oldham" coupling. For example, the side slot 568g of drive coupler 568a is transverse and/or perpendicular to a slot defined by coupling end 568b of drive coupler 568a, whereby the drive coupler 568a couples transfer shaft 568c of drive transfer assembly 568 and drive shaft 52a of motor 52 via an "Oldham" coupling. In some embodiments, one or more mating surfaces of any of the presently disclosed couplers, such as defined by coupling end 568b, for example, may include a slight draft angle to minimize backlash (e.g., the spring 568f pushes drive coupler 568a toward drive shaft 52a and the draft angle ensures that drive coupler 568a and drive shaft 52a are bottomed out or in close approximation).

The sterile interface module 530 further includes a ring coupler or gear 572 supported on an inner surface of the rotatable collar 564 of the sterile interface module 530. The sterile interface module 530 includes an idler coupler or gear 574 supported on the intermediate portion 562b of the body member 562 of the sterile interface module 530. The idler gear 574 is enmeshed with a drive coupler or gear 568d of the first drive transfer assembly 568 and selectively engagable with the ring gear 572 (see FIGS. 43 and 44) in response to rotational movement of the rotatable collar 564. The sterile interface module 530 further includes support plates 576, 578 that are configured to laterally support the first and second drive transfer assemblies 568, 570. The support plate 576 of the sterile interface module 530 is secured within a support channel 564c (see FIG. 44) defined between the ring gear 572 and inner surfaces of the rotatable collar 564 such that the rotatable collar 564 can rotate about the support plate 576 while axially moving the support plate 576 relative to the transfer shafts 568c, 570a of first and second drive transfer assemblies 568, 570.

Figure 41:
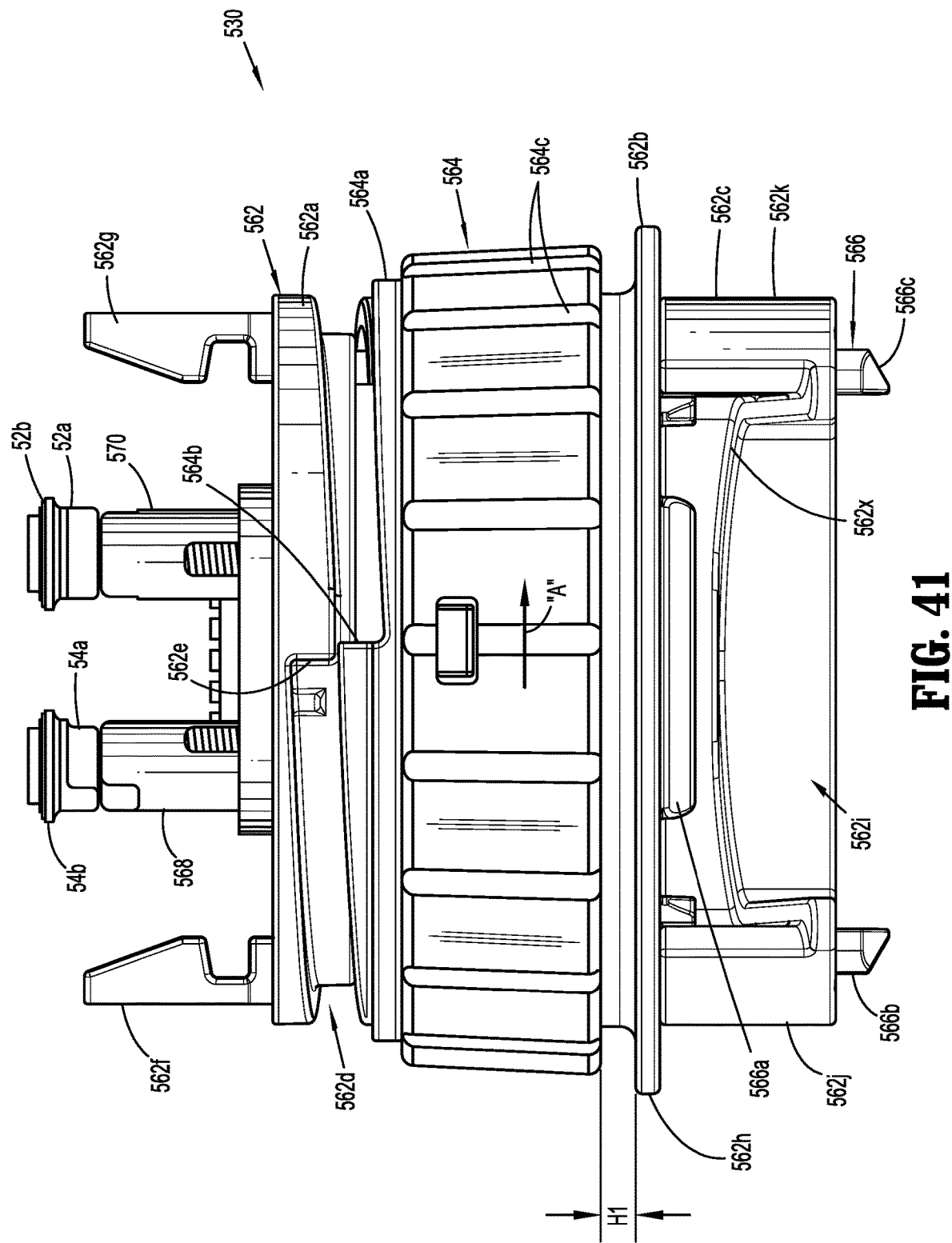
FIG. 41 is an enlarged, front view of a portion of the robotic surgical assembly of FIG. 1 with the sterile interface module thereof shown in a first position.

The support plate 576 can be secured to the drive couplers 568a, 570a of the first and second drive transfer assemblies 568, 570 to move the drive couplers 568a, 570a axially relative to the transfer shafts 568c, 570c of first and second drive transfer assemblies 568, 570 as the support plate 576 moves axially with the rotatable collar 564 of the sterile interface module 530. Axial movement of the drive couplers 568a, 570a enables the driver couplers 568a, 570a to selectively engage and disengage the driver couplers 568a, 570a to/from the motor couplers 54b, 52b of the motor assembly 50 of the housing 510 as the rotatable collar 564 of the sterile interface module 530 moves between first and second positions (and any number of intermediate positions between the first and second positions). The motor couplers 52b, 54b of the motor assembly 50 are engaged with the respective drive couplers 568a, 570a of the sterile interface module 530 while the rotatable collar 564 of the sterile interface module 530 is in the second position (FIGS. 42 and 44), and disengaged while the rotatable collar 564 of the sterile interface module 530 is in the first position (FIGS. 41 and 43). Advantageously, if the motor assembly 50 seizes, disengagement between the motor couplers 52b, 54b of the motor assembly 50 and the drive couplers 568a, 570a of the sterile interface module 530 provides a simplified separation of the sterile interface module 530 from the motor assembly 50 for an emergency release.

To couple an electromechanical surgical instrument such as electromechanical surgical instruments 200, 250 etc. to the sterile interface module 530, the ramped camming surfaces of the electrosurgical instrument (e.g., the ramped camming surfaces 218 of the housing 212 of the electromechanical surgical instrument 200) are aligned with the corresponding ramp surfaces 562x of the lower portion 562c of the sterile interface module 530. The electromechanical surgical instrument 200 is then transversely moved (e.g., side loaded) relative to the robotic surgical assembly 500 until the ramped camming surfaces of the electromechanical surgical instrument are fully received or seated on ramp surfaces 562x of the lower portion 562c of the sterile interface module 530 similar to that described above with respect to coupling cuff 176.

As the electromechanical surgical instrument is transversely moved into the lower portion 562c, the electromechanical surgical instrument cams upwardly (proximally, similar to that described above with respect to coupling cuff 176) to proximally move or compress the floating plate 566. Movement of the floating plate 566 into the compressed position draws the transfer shafts 568c, 570c (and their corresponding instrument engagement ends 568e, 570e) proximally away from the instrument opening 562i of lower portion 562c of the sterile interface module 530 to facilitate insertion of the electromechanical surgical instrument 250 into the instrument opening 562i of the sterile interface module 530. Moving the floating plate 566 to the compressed position helps prevent insertion contact/interference between the instrument engagement ends 568e, 570e of the first and second drive transfer assemblies 568, 570 of the sterile interface module 530 and corresponding couplers of the electromechanical surgical instrument (e.g., the first and second drive assemblies 256a-256d of electromechanical surgical instrument 250 or the proximal couplers 310 of electromechanical surgical instrument 200).

Once the electromechanical surgical instrument, such as electrosurgical instrument 250, is fully seated within the lower portion 562c of the sterile interface module 530, the floating plate 566 is urged back to the extended position thereof so that the instrument engagement ends 568e, 570e of the first and second drive transfer assemblies 568, 570 of the sterile interface module 530 and corresponding couplers of the first and second drive assemblies 256a-256d of the electromechanical surgical instrument 250 come into registration with one another to couple the electromechanical surgical instrument 250 to the robotic surgical assembly 500 via the sterile interface module 530.

In use, with the robotic surgical assembly 500 secured to one of the surgical robotic arms 2, 3 and any electromechanical surgical instrument 200, 200', 200" secured to the robotic surgical assembly 500, a clinician can perform a surgical procedure by robotically controlling, e.g., the electromechanical surgical instrument 250, with the robotic surgical assembly 500 as desired. In particular, with rotatable collar 564 of the sterile interface module 530 positioned in the second position to engage the motor and drive couplers 52b, 54b, 568a, 570a of the housing 510 and the sterile interface module 530, respectively, one or more of the motors 52, 54 of the motor assembly 50 are actuated to rotate one or more of the motor couplers 52b, 54b of the motors 52, 54 so that one or more of the first and second drive transfer assemblies 568, 570 of the sterile interface module 530 cooperate with one or more of the first and second drive assemblies 256a-256d of the electromechanical surgical instrument 250 to operate and/or manipulate the end effector 252 thereof as described herein.

Figure 42:
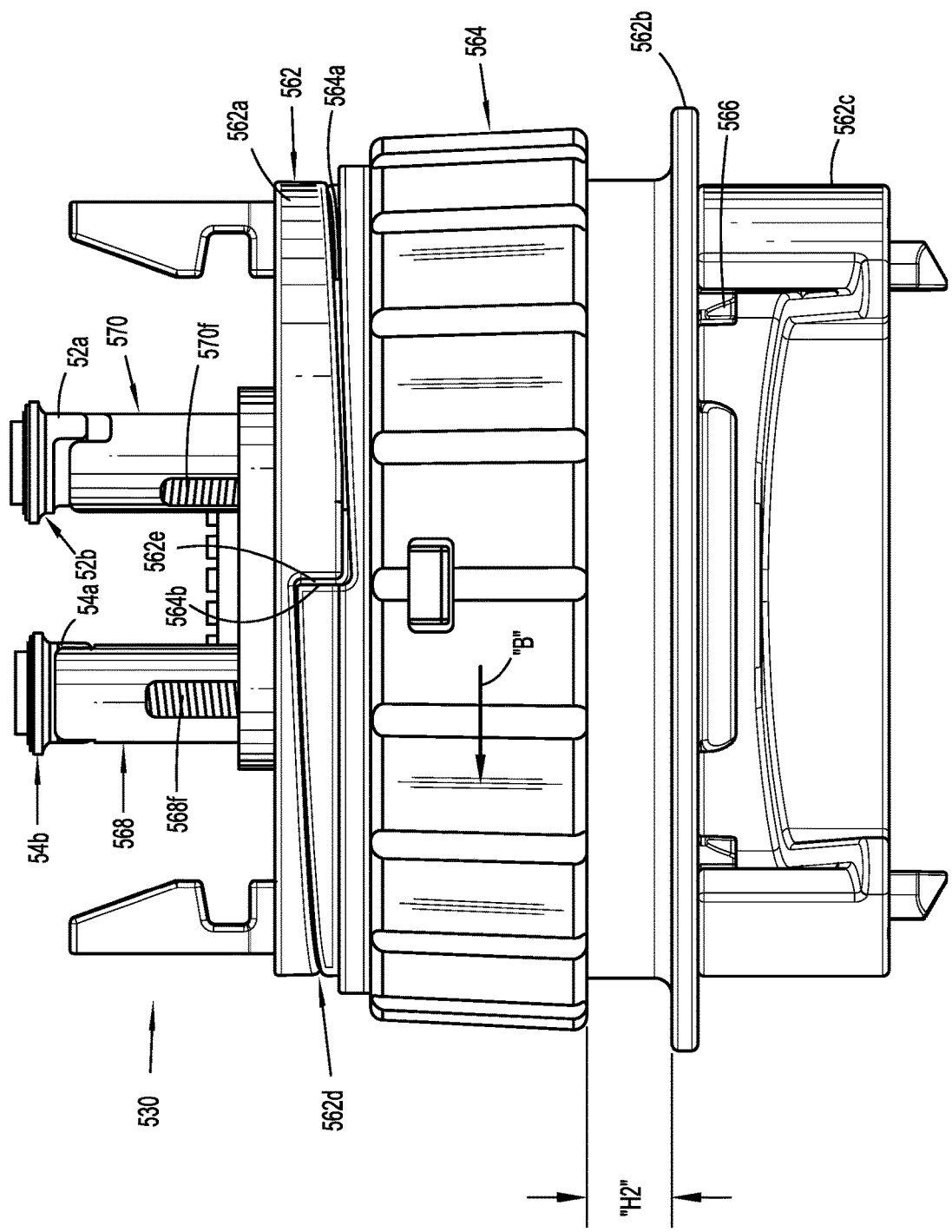
FIG. 42 is an enlarged, front view of the portion of the robotic surgical assembly shown in FIG. 41 with the sterile interface module thereof shown in a second position.
Figure 43:
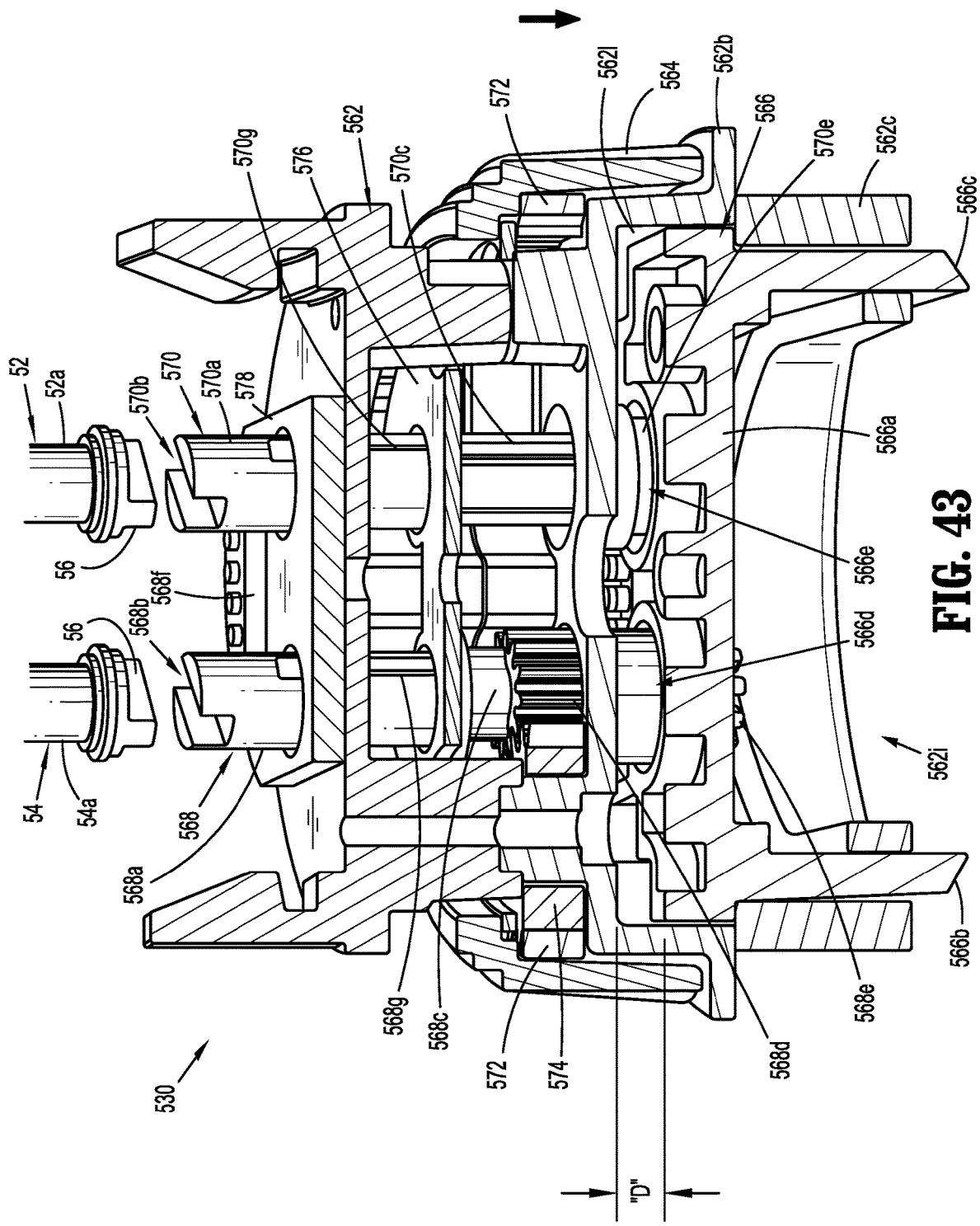
FIG. 43 is a perspective, cross-sectional view of the portion of the robotic surgical assembly shown in FIG. 41 with the sterile interface module thereof shown in the first position.
Figure 44:
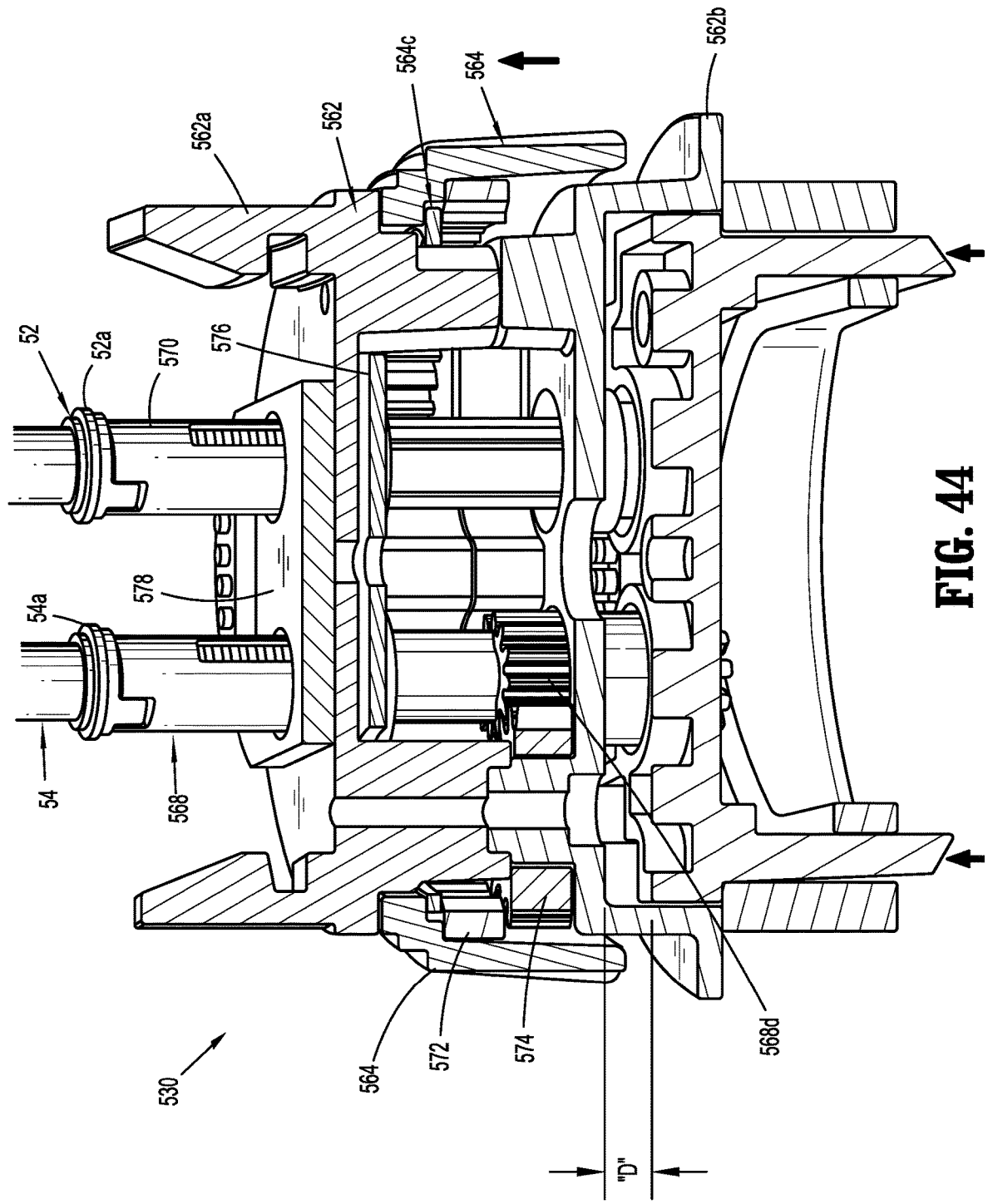
FIG. 44 is a perspective, cross-sectional view of the portion of the robotic surgical assembly shown in FIG. 41 with the sterile interface module thereof shown in the second position.
Figure 45:
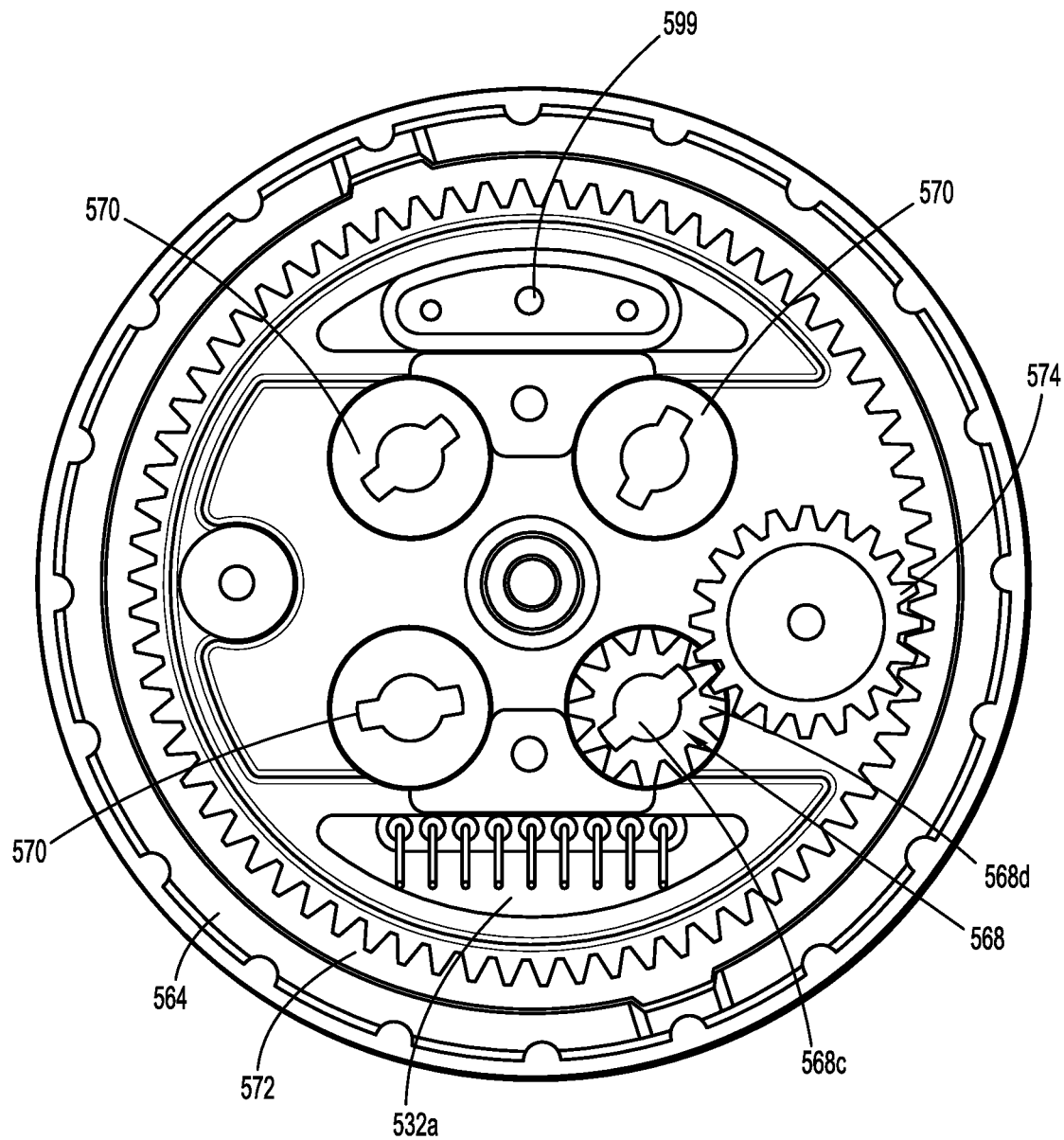
FIG. 45 is an enlarged, top, cross-sectional view of the sterile interface module in the first position.
Figure 46:
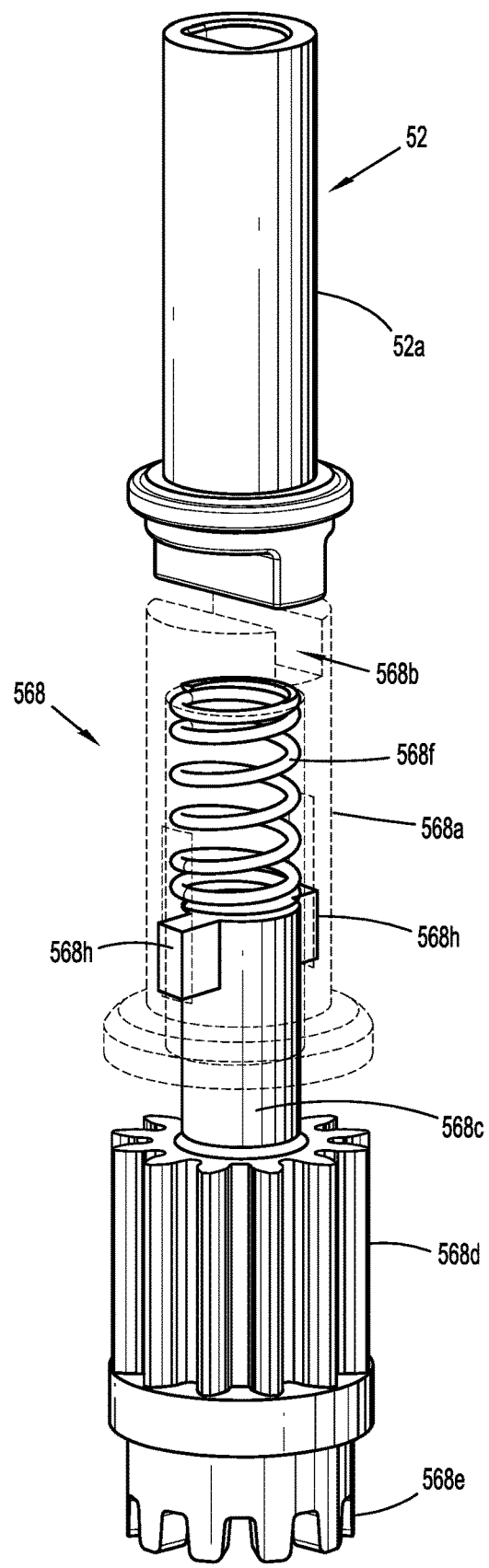
FIG. 46 is an enlarged, perspective view of a drive transfer assembly of the sterile interface module and a motor coupler of a motor assembly of the robotic surgical assembly of FIG. 1, the drive coupler shown in a first state.

With reference to FIGS. 42-44, in an emergency situation, while the rotatable collar 564 of the sterile interface module 530 is in the second position at the second height "H2" with the shoulders 562e, 564b of the upper portion 562a of the body member 562 and of the rotatable collar 562 engaged, the rotatable collar 564 can be rotated about the body member 562, as indicated by arrow "B," to move the rotatable collar 564 axially in the distal direction toward the flange 562h of the intermediate portion 562b of the body member 562 of the sterile interface module 530. In the second position of the rotatable collar 564, the ring gear 572 is longitudinally spaced from the idler gear 574.

As described above, the rotatable collar 564 of the sterile interface module 530 can be moved from the second position to the first position (any number of intermediate positions). For example, should a clinician need to manually control the end effector 252 of the electromechanical surgical instrument 250, for instance, during a power failure, a clinician can rotate the rotatable collar 564 of the sterile interface module 530 relative to the body member 562 of the sterile interface module 530 between the first and second positions (and any number of intermediate positions between the first and second positions) to move the rotatable collar 564 between first and second heights "H1" and "H2" relative to the flange 562h of the intermediate portion 562b of the body member 562 of the sterile interface module 530.

Once the rotatable collar 564 of the sterile interface module 530 is rotated (from the second position toward the first position) through a predetermined angular rotation (e.g., 90 degrees, although the sterile interface module 530, and/or one or more components thereof, can have any suitable configuration to create the desired predetermined angular rotation), the ring gear 572 of the sterile interface module 530 engages the idler gear 574 of the sterile interface module 530 to effectuate rotation of the idler gear 574 as the ring gear 572 rotates and axially advances distally toward the idler gear 574. Rotation of the idler gear 574 rotates the drive gear 568d of the first drive transfer assembly 568 of the sterile interface module 530 independent of the second drive transfer assemblies 570 of the sterile interface module 530 (which generally remain stationary without robotic control thereof). As the drive gear 568d of the first drive transfer assembly 568 rotates in response to rotation of the idler gear 574 of the sterile interface module 530, the first drive transfer assembly 568 of the sterile interface module 530 cooperates with the first drive assembly 256a of the electromechanical surgical instrument 250 to advantageously manually manipulate the end effector 252 thereof (e.g., to move one jaw thereof to open end effector 252 and release tissue grasped therein). It is also contemplated that the rotatable collar 564 of the sterile interface module 530 can be rotated in the opposite direction as desired to manipulate (e.g., close) the end effector 252 of the electromechanical surgical instrument 250.

The manual rotation of the rotatable collar 564 from the second position to the first position (and/or from the first position to the second position), imparts forces through the respective components of the sterile interface module 530 and the electromechanical surgical instrument 250 to manually manipulate the end effector 252 of the electromechanical surgical instrument 250 to position the end effector 252 in a desired orientation/position. For example, the end effector 252 of the electromechanical surgical instrument 250 can be manually manipulated to an open position to release tissue grasped by the end effector 252 so that the electromechanical surgical instrument 250 can be removed from a surgical site while limiting the risks of undesirable tissue damage that would otherwise be present if such manual manipulation were not feasible when a power failure or other similar emergency situation arises.

To remove the electromechanical surgical instrument 250 from the robotic surgical assembly 500, for example, to perform an instrument exchange (e.g., with one of electromechanical surgical instruments 200, 250', or 250"), a clinician can depress the paddles 254a, 254b of the detachment assembly 254. Depression of the paddles 254a, 254b imparts a force on the tabs 566b, 566c of the floating plate 566 of the sterile interface module 530 to move the floating plate 566 in a proximal direction relative to the body member 562 of the sterile interface module 530. As the floating plate 566 moves in a proximal direction, the transfer shafts 568c, 570c of the first and second drive transfer assemblies 568, 570 translate with the floating plate 566 in the proximal direction against biasing forces from the springs 568f, 570f of the first and second drive transfer assemblies 568, 570. Movement of the transfer shafts 568c, 570c of the first and second drive transfer assemblies 568, 570 relative to the body member 562 of the sterile interface module 530 separates the instrument engagement ends 568e, 570e of the transfer shafts 568c, 570c of the first and second drive transfer assemblies 568, 570 from the engagement couplers 258 of the respective first and second drive assemblies 256a-256d of the electromechanical surgical instrument 250. Once the instrument engagement ends or gears or couplers 568e, 570e of the transfer shafts 568c, 570c of the first and second drive transfer assemblies 568, 570 are separated from the engagement couplers 258 of the respective first and second drive assemblies 256a-256d of the electromechanical surgical instrument 250, the proximal end of the instrument housing 253 of the electromechanical surgical instrument 250 can be slid laterally out from the instrument opening 562i of the lower portion 562c of the body member 562.

The electromechanical surgical instrument 250 can be re-attached through the instrument opening 562i of the lower portion 562c of the body member 562 as described above. Alternatively, a different electromechanical surgical instrument such as the instrument 200, the endoscope 250,' or the grasper 250" can be likewise attached as desired.

Figure 58:
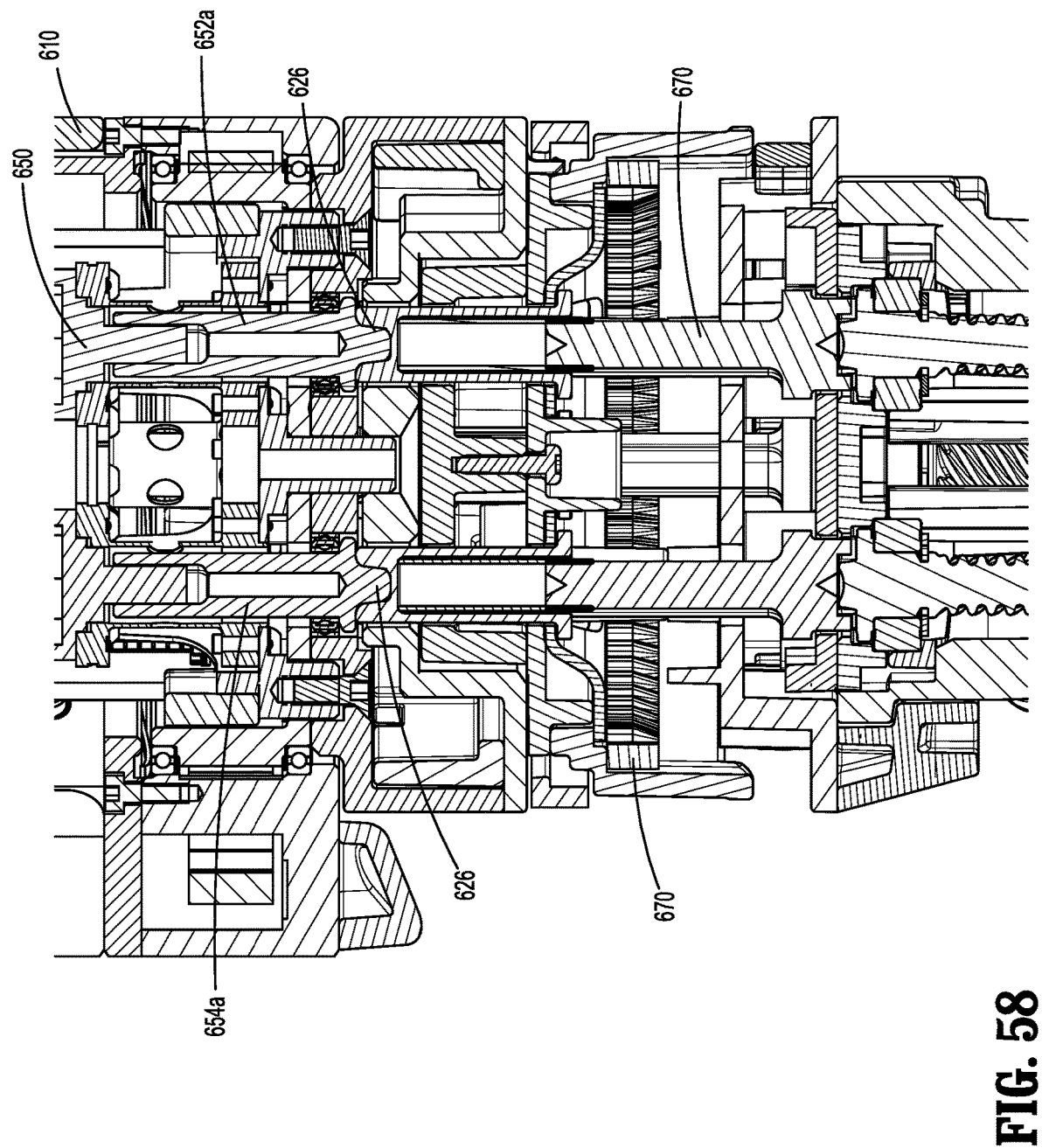
FIG. 58 is another longitudinal, cross-sectional view of the robotic surgical assembly of FIG. 48 including a surgical instrument connected thereto.

Turning now to FIGS. 48-58, a robotic surgical assembly, according to another embodiment of the present disclosure, is generally designated as 600. The robotic surgical assembly 600 is similar to the robotic surgical assembly 500 and thus will only be described in further detail herein to the extent necessary to describe differences in construction and use therebetween. The robotic surgical assembly 600 of the robotic surgical system 1 includes an instrument drive unit or housing 610 supporting a motor assembly or motor pack 650 (FIG. 58). The housing 610 of the robotic surgical assembly 600 includes a connector assembly 640.

Ring member 550 is configured for rotatable attachment to a distal end of the connector assembly 640 (e.g., via snap fit). The sterile drape 552 can be arranged as desired about the housing 610, the robotic surgical assembly 600 and the robotic arms 2, 3 to provide a sterile barrier between the various aforementioned components and/or the surgical site/fluids and the electromechanical surgical instruments 200 (FIG. 2), 250, 250', or 250".

A collar assembly or sterile interface module 630 is provided for selectively interconnecting robotic surgical assembly 600 and any one of the electromechanical surgical instruments 200, 250, 250', or 250".

As seen in FIGS. 49-53, the collar assembly or sterile interface module 630 includes electrical connectors 632a, 632b and an electrical ribbon (not shown) coupled between the electrical connectors 632a, 632b to provide electrical communication between the robotic surgical assembly 600 and any electromechanical surgical instrument, such as electromechanical surgical instrument 250, coupled thereto. The electrical connectors 632a, 632b can be coupled to the sterile interface module 630 by fasteners 697.

With reference to FIGS. 49-56, the sterile interface module 630 includes a body member 662 having an upper portion 662a, an intermediate portion 662b secured to upper portion 662a by fasteners 698, and a lower portion 662c secured to intermediate portion 662b by fasteners 699. The upper portion 662a of the body member 662 defines a helical channel 662d that extends around the upper portion 662a from a shoulder 662e of the upper portion 662a. The upper portion 662a further includes a pair of attachment arms 662f, 662g that extend proximally from the upper portion 662a to secure the sterile interface module 630 to the connector assembly 640 of the housing 610 of the robotic surgical assembly 600. The pair of attachment arms 662f, 662g may be disposed in mirrored relation on opposed sides of the upper portion 662a.

Figure 49:
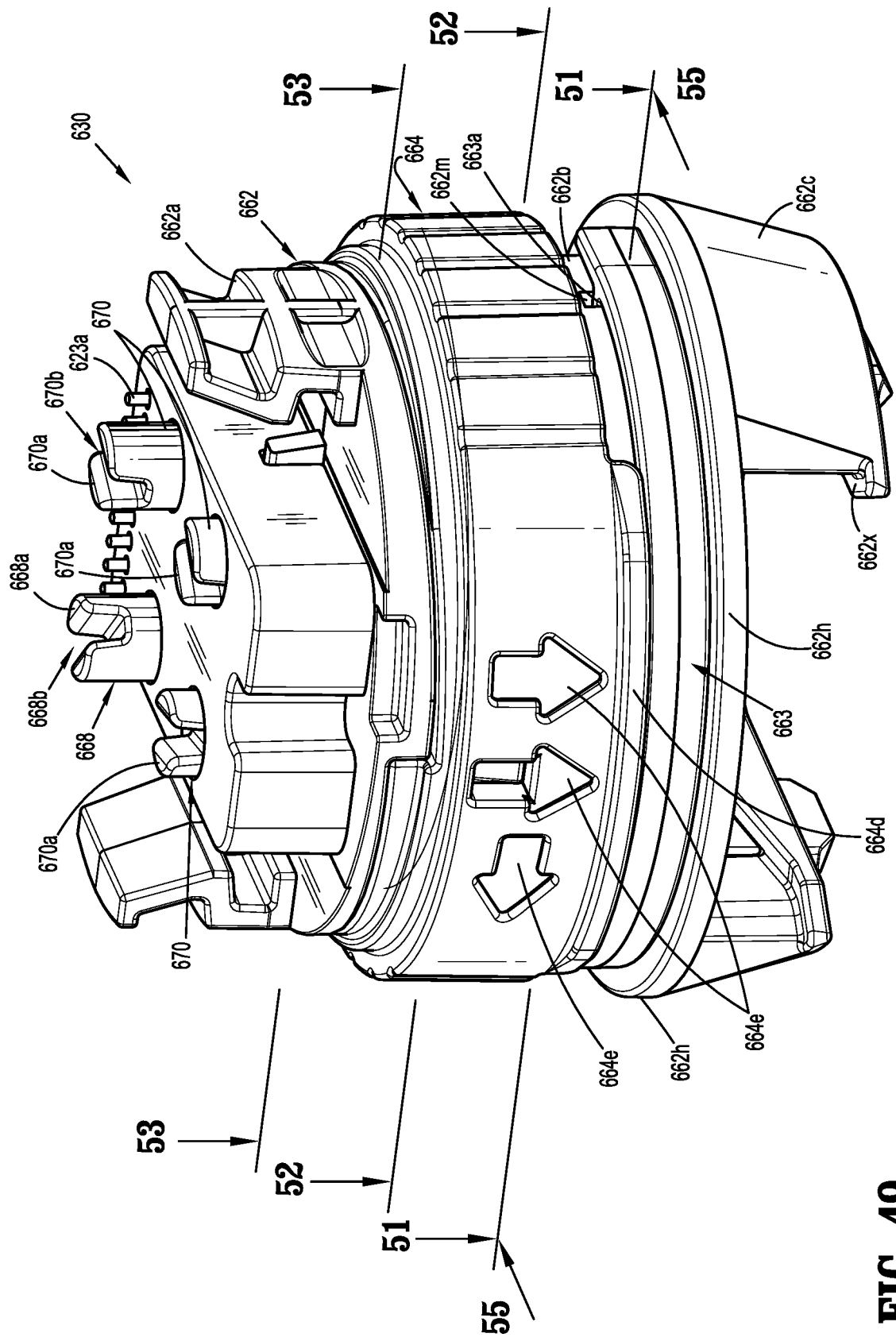
FIG. 49 is a perspective view of a sterile interface module of the robotic surgical assembly of FIG. 48, illustrating a safety clip in position.
Figure 50:
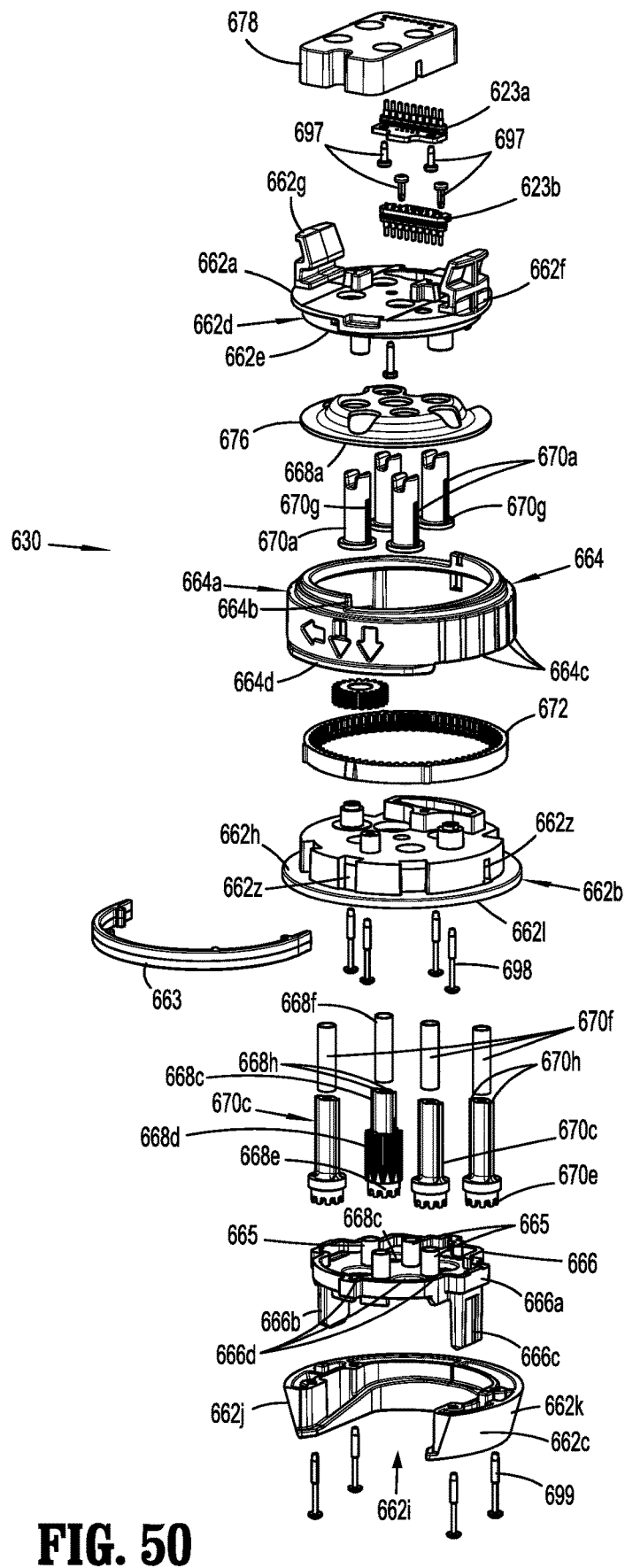
FIG. 50 is a perspective view, with parts separated, of the sterile interface module of FIG. 49.
Figure 51:
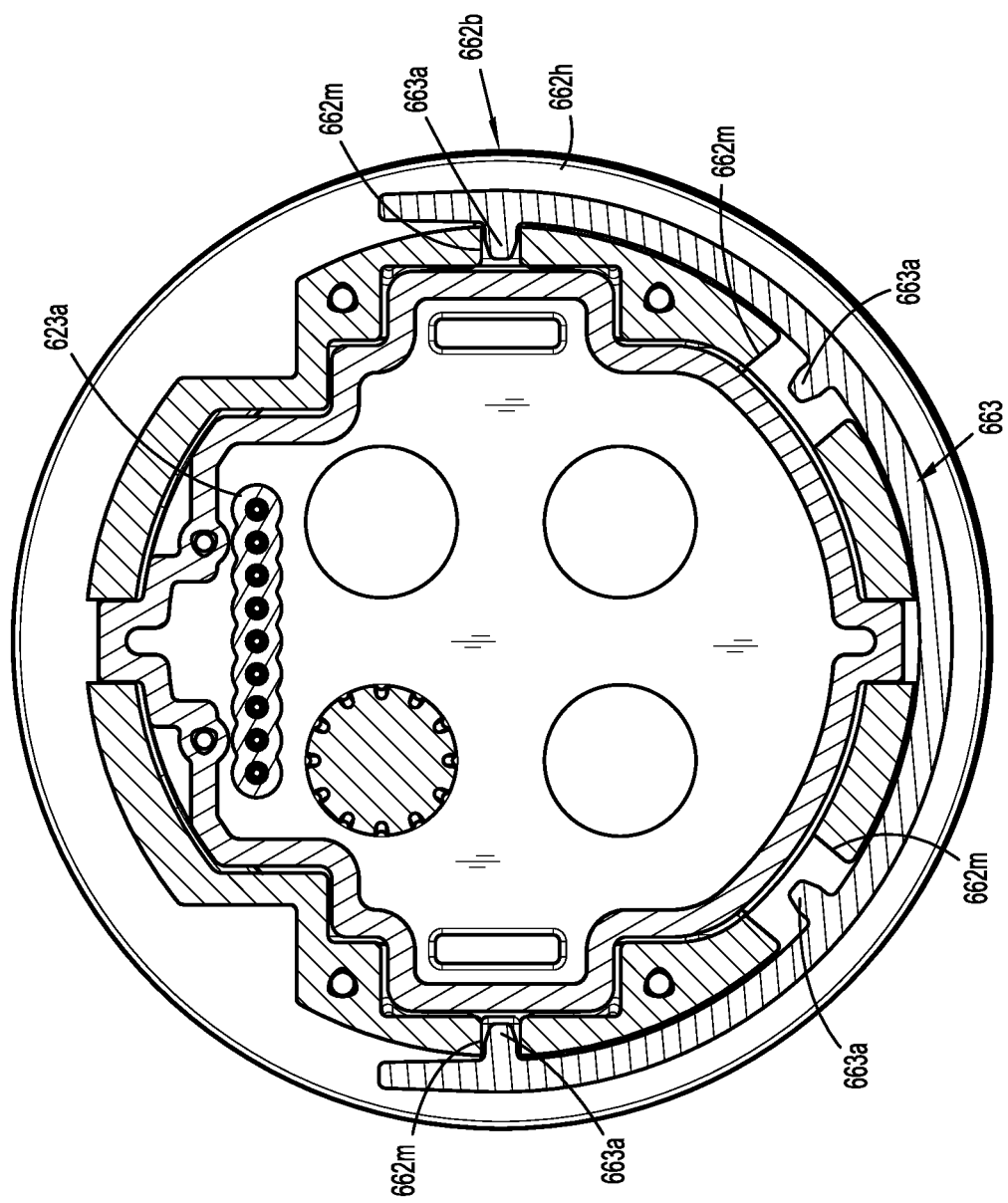
FIG. 51 is a cross-sectional view as taken through 51-51 of FIG. 49.
Figure 52:
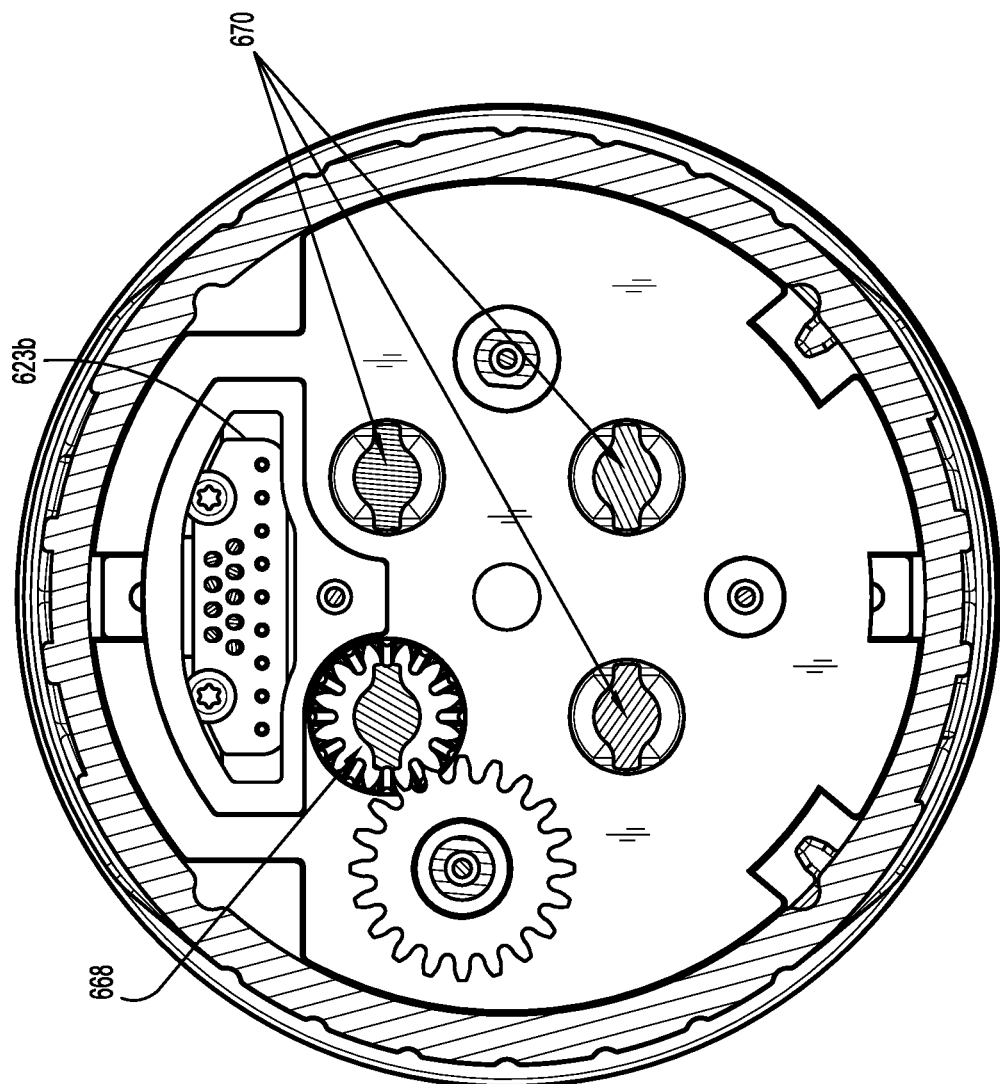
FIG. 52 is a cross-sectional view as taken through 52-52 of FIG. 49.
Figure 53:
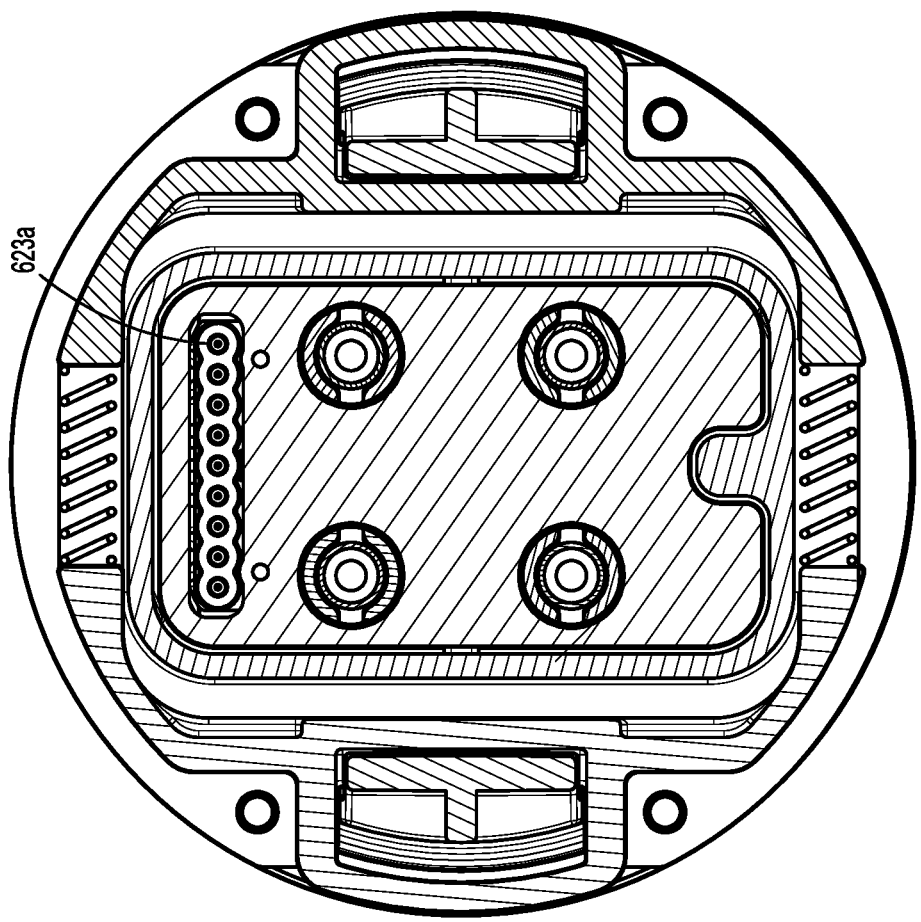
FIG. 53 is a cross-sectional view as taken through 53-53 of FIG. 49.
Figure 54:
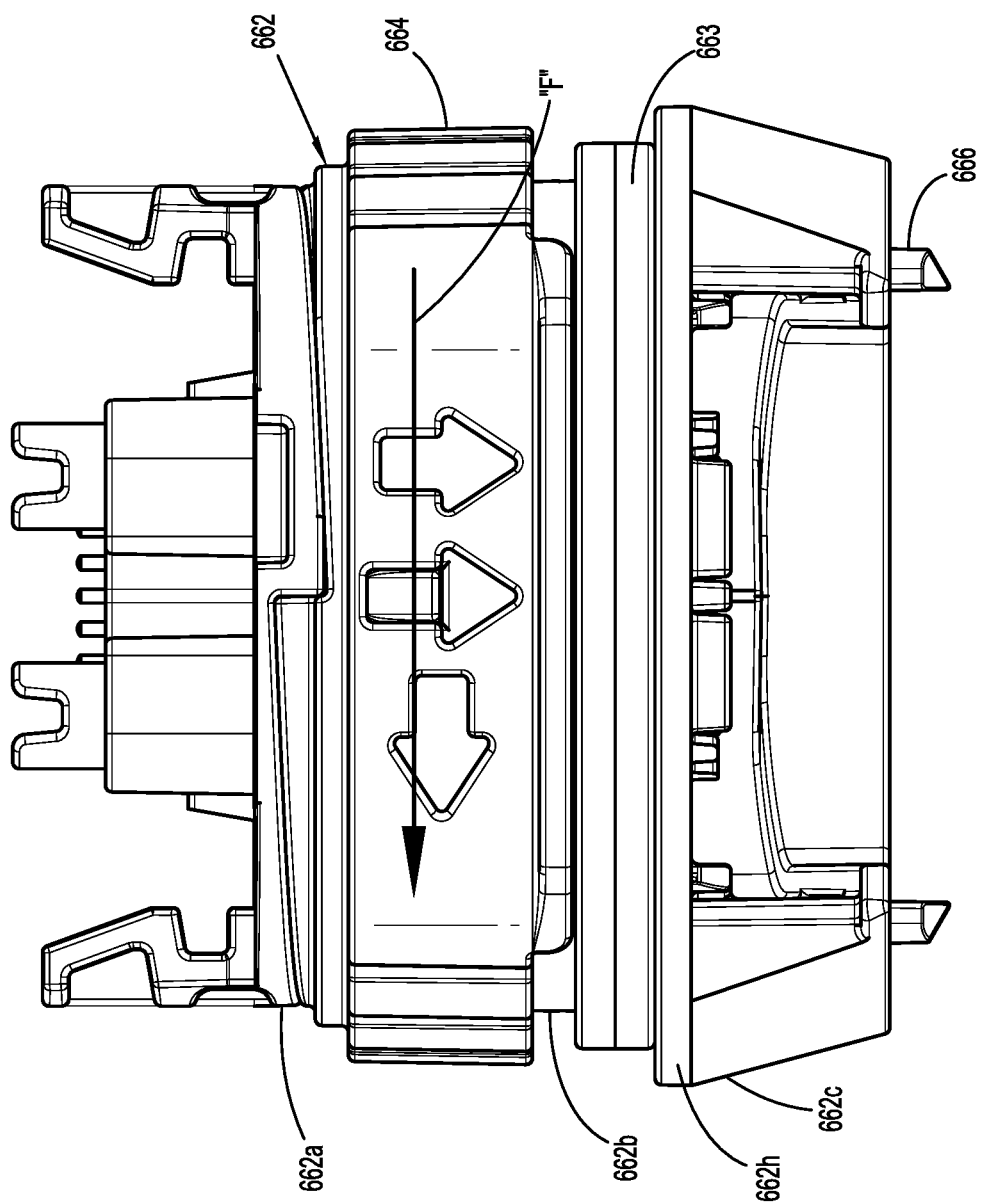
FIG. 54 is a side elevational view of the sterile module interface of FIGS. 48-53.

With reference to FIGS. 49-51, the intermediate portion 662b of the body member 662 includes a flange 662h and rotatably supports a rotatable collar 664 thereon. The intermediate portion 662b defines spaced apart openings 662m in a side surface thereof. A safety clip 663 may snap-fit into clip-receiving recesses 662m of intermediate portion 662b of body member 162 to secure safety clip 663 onto sterile interface module 630 at a location between rotatable collar 664 and flange 662h of intermediate portion 662b of body member 662. The safety clip 663 may take the form of a semi-circular cuff extending greater than 180° and be formed of a resilient material. The safety clip 163 acts like a block or stopper to prevent approximation of rotatable collar 664 toward flange 662h of intermediate portion 662b of body member 662, to thereby inhibit inadvertent approximation of rotatable collar 664 toward flange 662h of intermediate portion 662b. Prior to actuation of rotatable collar 664, as described above, the safety clip 663 must first be removed from between rotatable collar 664 and flange 662h of intermediate portion 662b. The safety clip 663 may include nubs or the like 663a extending radially inward therefrom and which are configured for receipt or disposition within openings 662m formed within intermediate portion 662b of body member 662.

The rotatable collar 664 of the sterile interface module 630 defines a helical channel 664a that extends from a shoulder 664b of the rotatable collar 664. The helical channel 664a of the rotatable collar 664 and the shoulder 664b of the rotatable collar 664 complement the helical channel 662d of the upper portion 662a of the body member 662 and the shoulder 662e of the upper portion 662a of the body member 662. The rotatable collar 664 further includes gripping grooves 664c to facilitate user gripping and/or actuation of the rotatable collar 664 relative to the body member 662 of the sterile interface module 630. The rotatable collar 664 also includes a lip 664d that extends distally from the rotatable collar 664 and is engagable with the safety clip 663 to enable the safety clip to prevent movement of the rotatable collar 664 toward the flange 662h of the intermediate portion 662b as discussed above. The rotatable collar 664 may also include indicia 664e thereon or defined therein (e.g., one or more arrows) to provide information to a clinician. In some embodiments, the indicia may provide operation instruction.

The lower portion 662c of the body member 662 of the sterile interface module 630 is in the form of a semi-annular coupling cuff that is secured to a distal end of the intermediate portion 662b of the body member 662 via fasteners 699. The lower portion 662c of the body member 662 includes a U-shaped body having an instrument opening 662i defined between side arms 662j, 662k and opening distally and laterally. The lower portion 662c further includes a ramp surface 662x (FIG. 49) that complements the ramped camming surfaces of the housing of the electromechanical surgical instruments (e.g., ramped camming surfaces 218 of the housing 212 of the electromechanical surgical instrument 200). The instrument opening 662i is configured to receive an electromechanical surgical instrument, such as electromechanical surgical instrument 250, therein to removably secure the electromechanical surgical instrument 250 to the robotic surgical assembly 600. The side arms 662j, 662k of the lower portion 662c extend distally from the intermediate portion 662b of the body member 662 and are positioned to support the electromechanical surgical instrument 250 within the instrument opening 662i of the lower portion 662c when the electromechanical surgical instrument 250 is received therein (e.g., via side loading).

Similar to the floating plate 566 of the sterile interface module 530, the sterile interface module 630 further includes a floating plate 666 supported between the intermediate portion 662b of the body member 662 and the lower portion 662c of the body member 662. The floating plate 666 is movable between an uncompressed position or extended position and a compressed or retracted position. The floating plate 666 is spring biased distally toward the uncompressed position by springs 665a disposed between the floating plate 666 and the intermediate portion 662b of the body member 662 and by springs of drive transfer assemblies (e.g., 668, 670) of the sterile interface module 630. In the uncompressed position of the lower floating plate 666, the floating plate 666 is spaced a distance "E" (see FIG. 55) from a bottom surface 662e of the intermediate portion 662b. The floating plate 666 includes a base portion 666a and tabs 666b, 666c that extend distally from the base portion 666a. The tabs 666b, 666c extend through the lower portion 662c of the body member 662. The floating plate 666 defines apertures 666d, 666e therein that receive first and second drive transfer assemblies 668, 670 of the sterile interface module 630.

With reference to FIGS. 49-52 and 58, the first and second drive transfer assemblies 668, 670 of the sterile interface module 630 include respective drive couplers 668a, 670a defining coupling ends 668b, 670b engagable with coupling ends 626 of respective motor couplers 652a, 654a of the motor assembly 650 supported within the housing 610. The first drive transfer assembly 668 includes a transfer shaft 668c and the second drive transfer assembly 670 includes a transfer shaft 670c. The transfer shafts 668c, 670c of the respective first and second drive transfer assemblies 668, 670 extend to a respective instrument engagement end or 668e, 670e (e.g., a gear or the like with distally extending teeth) at a distal end thereof. The transfer shaft 668c of the first drive transfer assembly 668 further includes a drive coupler or gear 668d supported proximal to instrument engagement end 668e of transfer shaft 668c.

Respective biasing members or springs 668f, 670f are supported between the drive couplers 668a, 670a and the transfer shafts 668c, 670c of each of the respective first and second drive transfer assemblies 668, 670 such that each spring 668f, 670f is configured to apply spring force to its respective first or second drive transfer assembly 668, 670 upon compression thereof. The biasing members 668f, 670f of the drive transfer assemblies 668, 670 may be compression springs. The drive couplers 668a, 670a of the first and second drive transfer assemblies 668, 670 define side slots 668g, 670g therein that slidably receive wings 668h, 670h extending from the transfer shafts 668c, 670c of the first and second drive transfer assemblies 668, 670. The wings 668h, 670h of the transfer shafts 668c, 670c are configured to slide through the side slots 668g, 670g of the first and second drive transfer assemblies 668, 670 in response to relative movement between one of the transfer shafts 668c, 670c and its respective drive coupler 668a, 670a (e.g., in the manner of an "oldham" coupling).

The sterile interface module 630 further includes a ring coupler or gear 672 supported on an inner surface of the rotatable collar 664 of the sterile interface module 630. The sterile interface module 630 includes an idler coupler or gear 674 supported by the intermediate portion 662b of the body member 662 of the sterile interface module 630. The idler gear 674 is enmeshed with the drive gear 668d of the first drive transfer assembly 668 and selectively engagable with the ring gear 672 (see FIGS. 55 and 56) in response to rotational movement of the rotatable collar 664.

The sterile interface module 630 further includes support plates 676, 678 that are configured to laterally support the first and second drive transfer assemblies 668, 670. The support plate 676 is generally supported between the upper portion 662a of the body member 662 and the intermediate portion 662b of the body member 662.

Figures 55, 56:
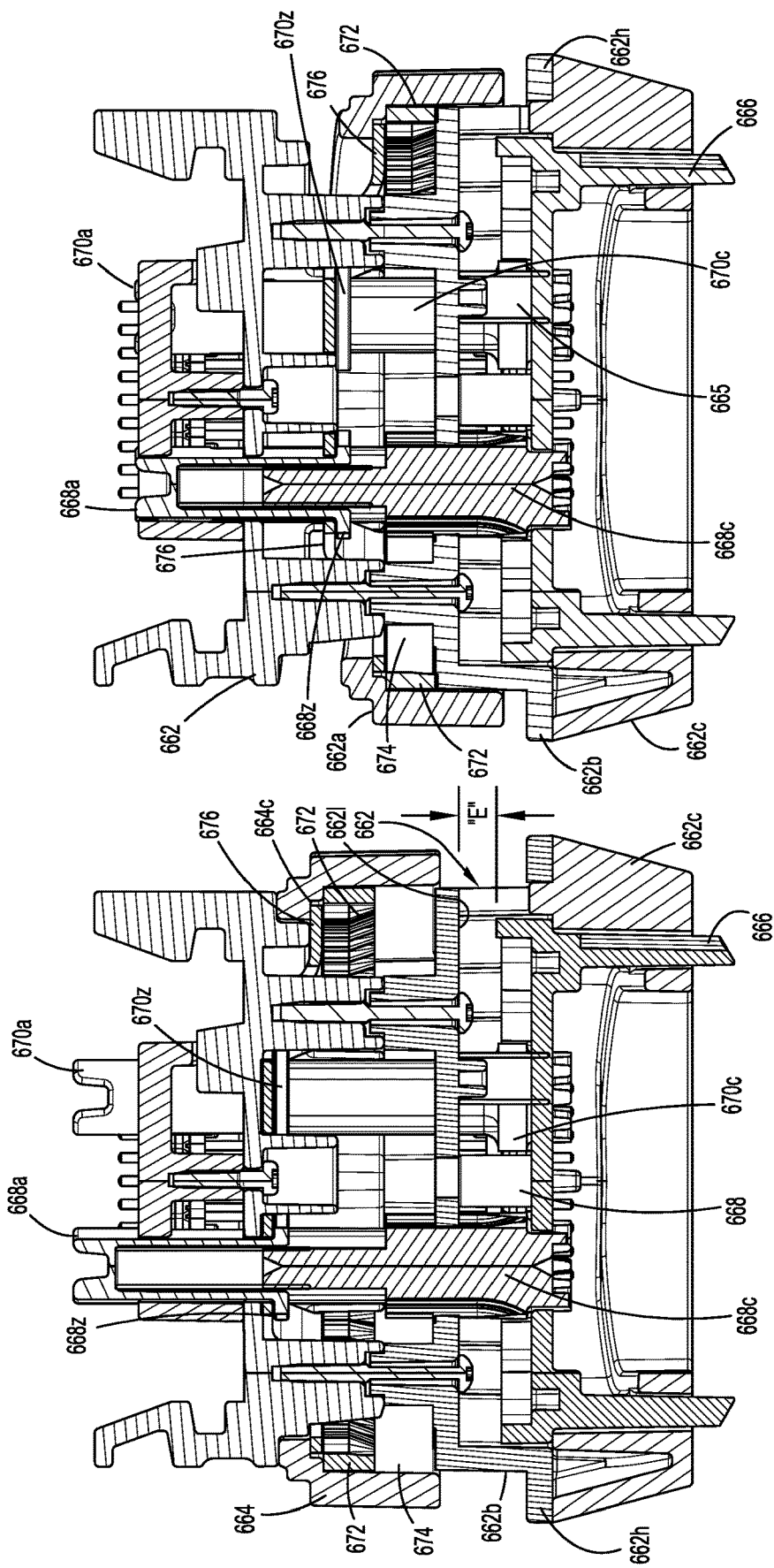
FIG. 55 is a cross-sectional, elevational view of the sterile module interface of FIGS. 48-54, as taken through 55-55 of FIG. 49, illustrating the sterile module interface in a first condition.
FIG. 56 is a cross-sectional, elevational view of the sterile module interface of FIG. 55, illustrating the sterile module interface in a second condition.
Figure 57:
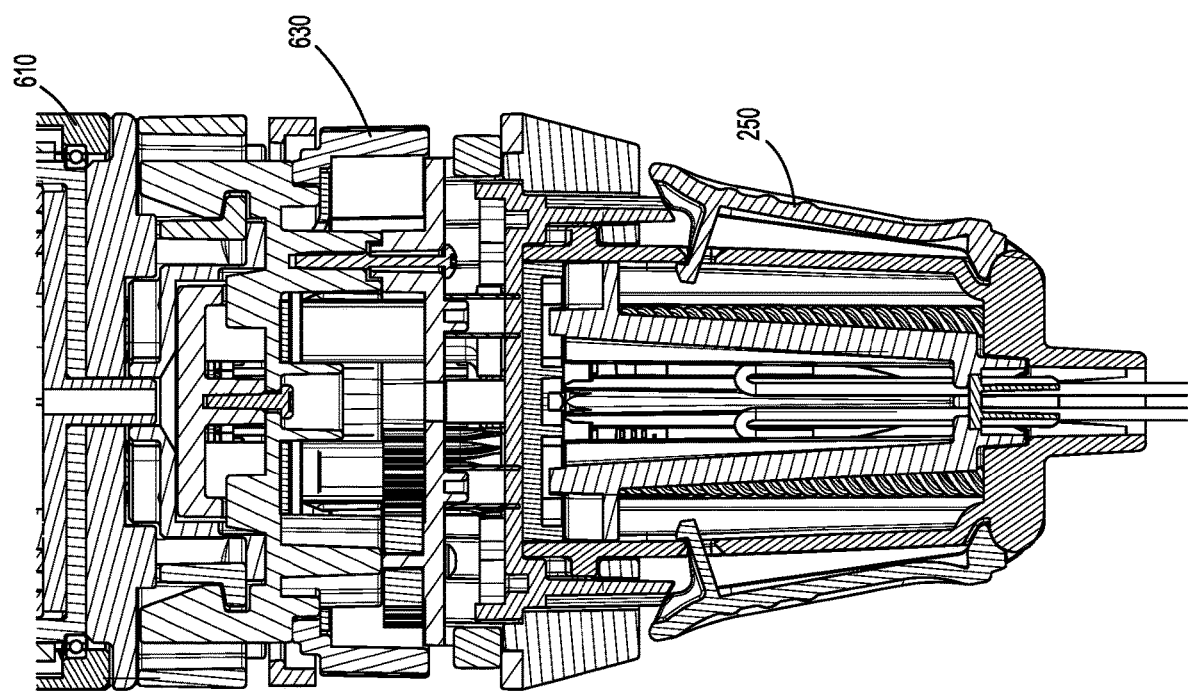
FIG. 57 is a longitudinal, cross-sectional view of the robotic surgical assembly of FIG. 48 including a surgical instrument connected thereto.

As seen in FIGS. 55 and 56, the support plate 676 of the sterile interface module 630 is secured within a support channel 664c defined between the ring gear 672 and inner surfaces of the rotatable collar 664 such that the rotatable collar 664, with the safety clip 663 removed as detailed herein, can rotate about the support plate 676 while axially moving the support plate 676 relative to the upper portion 662a of the body member 662 of the sterile interface module 630. The support plate 676 is coupled to flanges 668z, 670z of the drive couplers 668a, 670a of the first and second drive transfer assemblies 668, 670 to move the drive couplers 668a, 670a axially relative to the transfer shafts 668c, 670c of first and second drive transfer assemblies 668, 670 as the support plate 676 moves axially with the rotatable collar 664 of the sterile interface module 630. Axial movement of the drive couplers 668a, 670a enables the driver couplers 668a, 670a to selectively engage and disengage the driver couplers 668a, 670a to/from the motor couplers 652a, 654a (FIG. 58) of the motor assembly 50 of the housing 610 as the rotatable collar 664 of the sterile interface module 630 moves between first and second positions (and any number of intermediate positions between the first and second positions). The motor couplers 652a, 654a of the motor assembly 650 are engaged with the respective drive couplers 668a, 670a of the sterile interface module 630 while the rotatable collar 664 of the sterile interface module 630 is in the second position (FIGS. 55 and 58), and disengaged while the rotatable collar 664 of the sterile interface module 630 is in the first position (FIG. 56).

To couple an electromechanical surgical instrument, such as electromechanical surgical instrument 250, to sterile interface module 630, the ramped camming surfaces of the housing of the electromechanical surgical instrument (see e.g., the ramped camming surfaces 218 of the housing 212 of the electromechanical surgical instrument 200) are aligned with the corresponding ramp surfaces 662x of the lower portion 662c of the sterile interface module 630. The electromechanical surgical instrument 250 is then transversely moved (e.g., side loaded) relative to robotic surgical assembly 600 until seated on ramp surfaces 662x of the lower portion 662c of the sterile interface module 630 similar as that described above with respect to coupling cuff 176 and the sterile interface module 530.

As electromechanical surgical instrument 250 is transversely moved into the lower portion 662c, as described above, the floating plate 566 is urged toward the compressed position thereof against the spring bias of the first and second drive transfer assemblies 668, 670 and the spring bias of the springs 665 that extend proximally from the floating plate 666. Movement of the floating plate 666 into the compressed position draws the transfer shafts 668c, 670c (and their corresponding instrument engagement ends 668e, 670e) proximally away from the instrument opening 662i of lower portion 662c of the sterile interface module 630 to facilitate insertion of the electromechanical surgical instrument 250 into the instrument opening 662i of the sterile interface module 630. Moving the floating plate 666 to the compressed position helps prevent insertion contact/interference between the instrument engagement ends 668e, 670e of the first and second drive transfer assemblies 668, 670 and corresponding gears or couplers of the first and second drive assemblies 256a-256d of the electromechanical surgical instrument 250.

Once the electromechanical surgical instrument 250 is fully seated within the lower portion 662c of the sterile interface module 630, the floating plate 666 is urged back to the extended position thereof in response to the spring bias of springs 665 and first and second drive transfer assemblies 668, 670 so that the instrument engagement ends 668e, 670e of the first and second drive transfer assemblies 668, 670 of the sterile interface module 630 and corresponding gears or couplers of the first and second drive assemblies 256a-256d of the electromechanical surgical instrument 250 come into registration with one another to couple the electromechanical surgical instrument 250 to the robotic surgical assembly 600 via the sterile interface module 630.

In use, with the robotic surgical assembly 600 secured to one of the surgical robotic arms 2, 3 and any electromechanical surgical instrument 200, 250, 250', 250" secured to the robotic surgical assembly 600, a clinician can perform a surgical procedure by robotically controlling, e.g., the electromechanical surgical instrument 250 with the robotic surgical assembly 600 as desired. In particular, with rotatable collar 664 of the sterile interface module 630 positioned in the second position, the motor assembly 50 can be actuated to so that one or more of the first and second drive transfer assemblies 668, 670 of the sterile interface module 530 cooperate with one or more of the first and second drive assemblies 256a-256d of the electromechanical surgical instrument 250, for example, to operate and/or manipulate the end effector 252 thereof as described herein similar to that described above with respect to robotic surgical assembly 500.

With reference to FIGS. 51, 54-56, and 58, in an emergency situation (e.g. a power failure), the safety clip 663 is manually removed from the sterile interface module 630 while the rotatable collar 664 of the sterile interface module 630 is in the second position with the ring gear 672 longitudinally spaced from the idler gear 674. Once the safety clip 663 is removed, the rotatable collar 664 can be manually rotated about the body member 662, as indicated by arrow "F" (FIG. 54), to move the rotatable collar 664 axially in the distal direction toward the flange 662h of the intermediate portion 662b of the body member 662 of the sterile interface module 630 to separate the drive couplers 668a, 670a of the first and second drive transfer assemblies 668, 670 from the motor couplers 652a, 654a of the motor assembly 650 of the housing 610 similar to that described above with respect to sterile interface module 530.

Further, similar to sterile interface module 530, the rotatable collar 664 of the sterile interface module 630 can be rotated from the second position toward the first position through a predetermined angular rotation. With the ring gear 672 coupled to the rotatable collar 664, such rotation enables the ring gear 672 of the sterile interface module 630 to engage the idler gear 674 of the sterile interface module 630 to cause rotation of the idler gear 674 as the ring gear 672 rotates and axially advances distally toward the idler gear 674. Rotation of the idler gear 674 rotates the drive gear 668d of the first drive transfer assembly 668 of the sterile interface module 630 independent of the second drive transfer assemblies 670 of the sterile interface module 630 (which generally remain stationary without robotic control thereof).

As the drive gear 668d of the first drive transfer assembly 668 rotates in response to rotation of the idler gear 674 of the sterile interface module 630, the first drive transfer assembly 668 of the sterile interface module 630 cooperates with the first drive assembly 256a of the electromechanical surgical instrument 250 to advantageously manually manipulate the end effector 252 thereof similar to that described above with respect to sterile interface module 530.

To remove the electromechanical surgical instrument 250 from the robotic surgical assembly 600, for example, to perform an instrument exchange (e.g., with one of electromechanical surgical instruments 200, 250' or 250"), a clinician can depress the paddles 254a, 254b of the detachment assembly 254 of the electromechanical surgical instrument 250 to release the electromechanical surgical instrument 250 from the robotic surgical assembly 600 similar to that described above with respect to robotic surgical assembly 500. In particular, depressing the paddles 254a, 254b of the detachment assembly 254 of the electromechanical surgical instrument 250 moves the floating plate 666 to move to the compressed position against the bias of the springs of the sterile interface module 630 to enable the electromechanical surgical instrument 250 to be slid laterally out from the instrument opening 662i of the lower portion 662c of the body member 662 thereof similar to that described above with respect to sterile interface module 530.

The electromechanical surgical instrument 250 can be re-attached through the instrument opening 662i of the lower portion 662c of the body member 662 as desired or needed. Alternatively, a different electromechanical surgical instrument such as the instrument 200, the endoscope 250' or the grasper 250" can be likewise attached as desired or needed.

The drive members 380 and/or the connector members "CM" (see FIGS. 15 and 36) of some embodiments of the electromechanical surgical instruments may include any suitable material such as stainless steel, tungsten, polymer or the like. Such material may include one or more coatings, which may include one or more layers. These coatings may include polymeric material such as any suitable poly(p-xylylene) polymer (e.g., parylene or the like). Any of these polymeric materials can be formed by any suitable technique such as chemical vapor deposition or the like. Such coatings are configured to increase reliability and/or the life-cycle of the drive members 380 and/or the connector members "CM." Advantageously, poly(p-xylylene) polymers such as parylene are bio-compatible and provide low-friction and lubricity for application to almost any surface (e.g., a cable). For example, the presently described electromechanical surgical instruments may include drive or connecting members formed of tungsten cables coated with a poly(p-xylylene) polymers such as parylene in order to provide longer instrument life. In addition, such poly(p-xylylene) polymers provide a dielectric barrier. The poly(p-xylylene) polymer coating protects the tungsten cables (and any internal lubricants of the tungsten cables) from washing and/or autoclaving procedures. In addition, the poly(p-xylylene) polymer coating provides a layer of protection between the tungsten cables and the pulleys on which the tungsten cables ride. In certain embodiments, the one or more coatings may include polytetrafluoroethylene (e.g., Teflon) or the like material.

Any of the presently described sterile interface modules, or portions thereof, can be formed of dielectric material (e.g., any suitable polymer) and/or function as a dielectric to prevent current leakage. For example, one suitable polymer may include Polyphenylsulfone (e.g., Radel® R-5100) or the like. In some embodiments, the presently described sterile interface modules are configured to electrically isolate dedicated electrocautery cables, such as electrosurgical cable 599 (see FIG. 45) or the like from other electrical components such as those used for information transmission (e.g., electrical connectors 532a, 632a, electrical ribbon 534, etc.) Further, the electrosurgical cable and/or any electrical component, such as electrical connectors 532a, can be positioned as predetermined spaced locations relative to one another, whereby predetermined distance between such components can act as a dielectric.

In some embodiments, the presently described sterile interface modules, or portions thereof, may be autoclavable.

Figure 59:
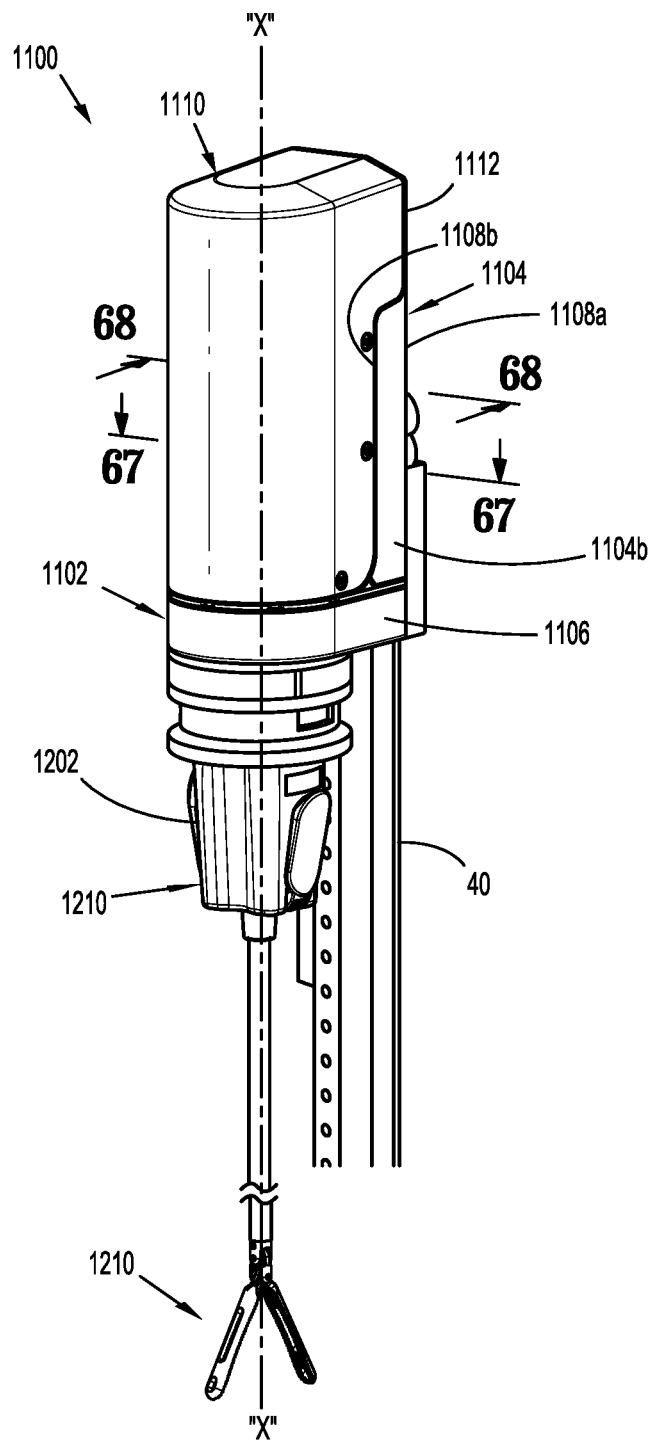
FIG. 59 is a perspective view of another embodiment of the surgical assembly of FIG. 1 including a surgical instrument holder, an instrument drive unit, and a surgical instrument.
Figure 60B:
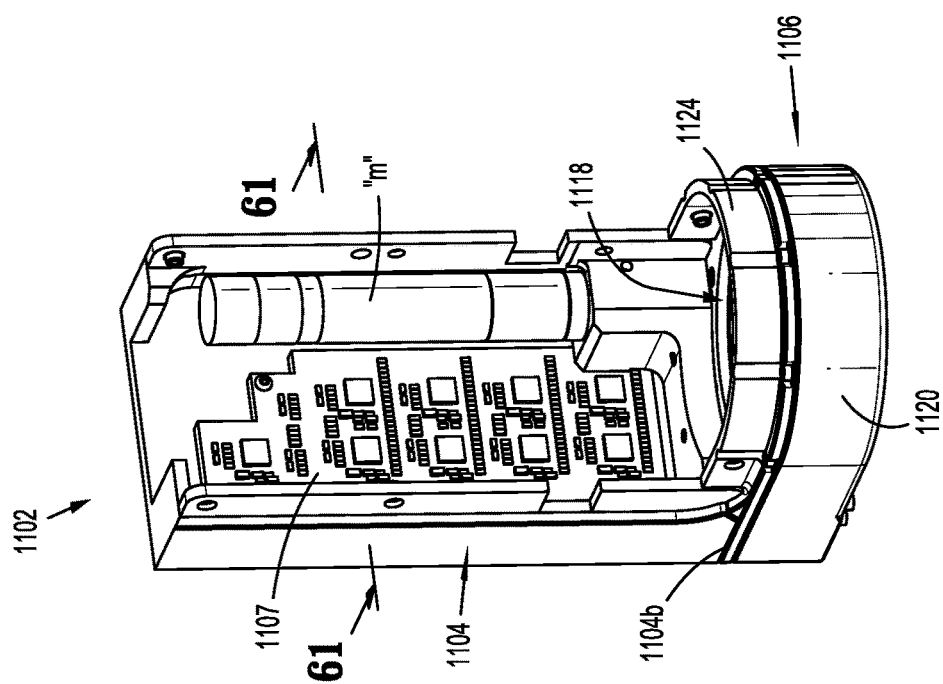
FIG. 60B is a perspective view, with parts assembled, of the surgical instrument holder of FIG. 59.
Figure 60A:
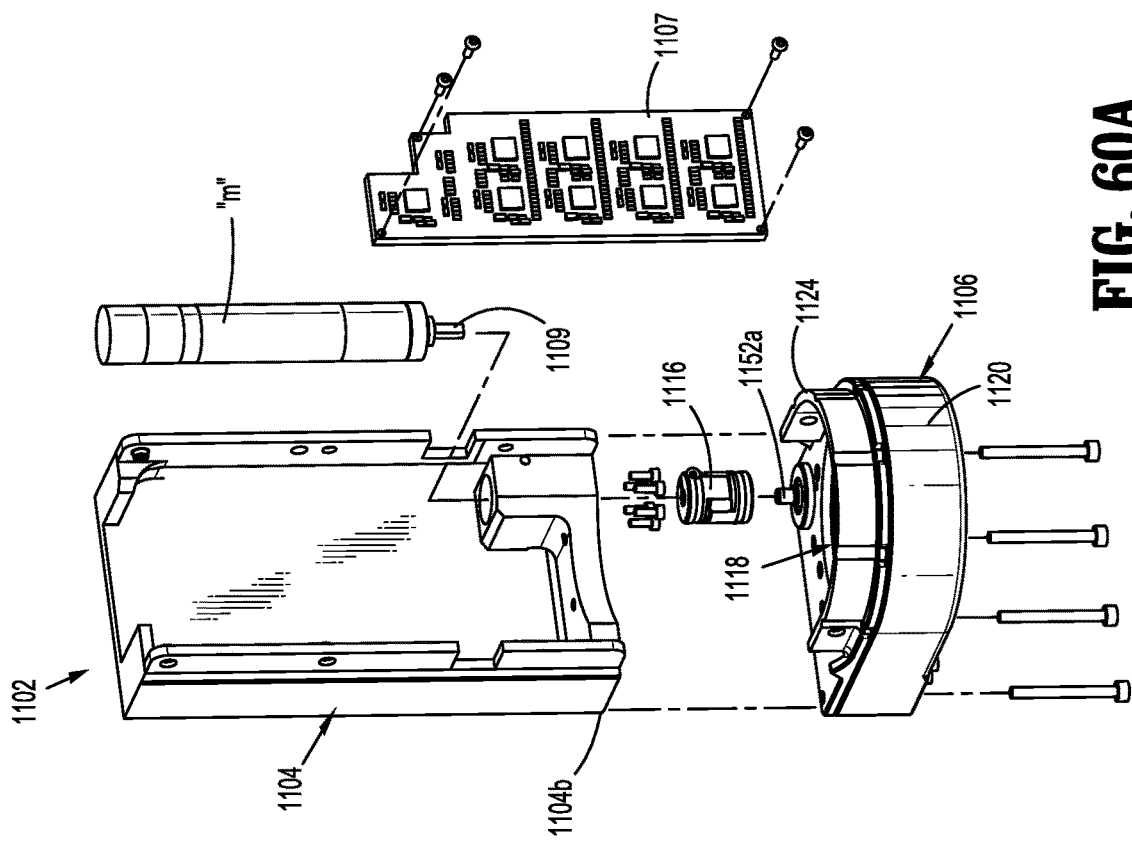
FIG. 60A is a perspective view, with parts separated, of the surgical instrument holder of FIG. 59.

With reference to FIG. 59, one embodiment of a robotic surgical system includes a robotic surgical assembly 1100 coupled with or to one of the robotic arms 2 or 3 (see FIG. 1). The robotic surgical assembly 1100 includes a surgical instrument holder 1102, an instrument drive unit 1110, and an electromechanical surgical instrument such as electromechanical surgical instrument 1200. The instrument drive unit 1110 transfers power and actuation forces from its motors to driven members (not shown) of the electromechanical surgical instrument 1200 to ultimately drive movement of components of an end effector 1210 of the electromechanical surgical instrument 1200, for example, a movement of a knife blade (not shown) and/or a closing and opening of jaw members of the end effector 1210, the actuation or firing of a stapler, and/or the activation or firing of an electrosurgical energy-based instrument, or the like. A motor assembly 1114 (FIGS. 67 and 68) of the instrument drive unit 1110 is rotated by motor "M" supported in the surgical instrument holder 1102 and transfers its rotational motion to the electromechanical surgical instrument 1200.

With reference to FIGS. 59, 60A, 60B, and 61, the surgical instrument holder 1102 of the surgical assembly 1100 functions to actuate a rotation of the motor assembly 1114 (FIG. 68) of the instrument drive unit 1110. The surgical instrument holder 1102 includes a back member or carriage 1104, and an outer member or housing 1106 extending laterally (e.g., perpendicularly) from an end 1104b of a carriage 1104. In some embodiments, the housing 106 may extend at various angles relative to the carriage 1104 and from various portions of the carriage 1104. The carriage 1104 has a first side 1108a and a second side 1108b, opposite to the first side 1108a. The first side 1108a of the carriage 1104 is detachably connectable to the rail 40 of the robotic arm 2 to enable the surgical instrument holder 1102 to slide or translate along the rail 40 of the robotic arm 2 (see FIG. 1). The second side 1108b of the carriage 1104 is configured to non-rotatably support a housing or outer shell 1112 of the instrument drive unit 1110.

The carriage 1104 of the surgical instrument holder 1102 supports or houses a motor, such as, for example, a canister motor "M" therein. The motor "M" receives controls and power from the control device 4 (FIG. 1) to ultimately rotate the motor assembly 1114 of the instrument drive unit 1110, as will be described in detail below. In some embodiments, the carriage 1104 may include a printed circuit board 1107 in electrical communication with the motor "M" to control an operation of the motor "M" of the carriage 1104. The carriage 1104 has a rotatable drive shaft 1109 extending from the motor "M" and longitudinally through the carriage 1104. The carriage 1104 further includes a shaft coupling 1116 non-rotatably connected to a drive shaft 1109 of the motor "M" to transfer rotation of the drive shaft 1109 of the motor "M" to a pulley 1154 of a drive assembly 1150 of the surgical instrument holder 1102.

With reference to FIGS. 60A-64B, the housing 1106 of the surgical instrument holder 1102 defines a channel 1118 therethrough configured to rotatably receive and support the instrument drive unit 1110 therein. The housing 1106 has a generally oblong semicircular shape, but in some embodiments, the housing 1106 may assume a variety of shapes, such as, for example, C-shaped, U-shaped, V-shaped, hook-shaped, or the like. The housing 1106 of the surgical instrument holder 1102 is further configured to house or retain the components of the drive assembly 1150, which will be described in detail below.

With specific reference to FIGS. 62, 63, 64A, and 64B, the housing 1106 of the surgical instrument holder 1102 generally includes a sidewall 1120 defining an enclosure 1122 therein, and a top plate 1124 connected to a top portion of the sidewall 1120. The sidewall 1120 has a first portion 1120a having a semicircular configuration and a second portion 1120b having a square or rectangular configuration. The first portion 1120a of the sidewall 1120 has a top ridge or ledge 1126a extending inwardly into the enclosure 1122 from the top portion of the sidewall 1120. The top ledge 1126a defines a cutout 1128a therein configured for receipt of a portion of a first bearing 1153a of the drive assembly 1150. The first bearing 1153a has an inner diameter of approximately 50-70 millimeters, for example, about 60 millimeters, an outer diameter of approximately 50-70 millimeters, for example, about 66 millimeters, a width of approximately 1-4 millimeters, for example, about 2.5 millimeters, and a mass of approximately 5-15 grams, for example, about 9 grams. The housing 1106 further includes a base 1130 disposed within the enclosure 1122.

The base 1130 is connected to a bottom portion of the sidewall 1120. The base 1130 includes a circular inner surface 1132 that defines the circular channel 1118 therethrough. The circular channel 1118 is configured for receipt of an annular member 1182 of the drive assembly 1150. The base 1130 further includes a bottom ridge or ledge 1126b extending inwardly into the central channel 1118 from the inner surface 1132 of the base 1130. The bottom ledge 1126b defines a cutout 1128b therein configured for receipt of a second bearing 1153b of the drive assembly 1150, similar to the first bearing 1153a described above. The top and bottom ledges 1126a, 1126b of the housing 1106 cooperatively define a groove 1134 therebetween configured for slidable receipt of a belt 1160 of the drive assembly 1150.

The housing 1106 further includes a curved or arcuate wall 1136 extending upwardly from base 1130, and is disposed adjacent the second portion 1120b of the sidewall 1120, partially surrounding the central channel 1118. The arcuate wall 1136 of the housing 1106 has a top ridge or ledge 1138 extending into the enclosure 122 and outwardly from an inner surface 1140 of the arcuate wall 1136. The top ledge 1138 of the arcuate wall 1136 is coplanar with the top ledge 1126a of the first portion 1120a of the sidewall 1120 such that the top ledges 1126a, 1138 provide clearance for a pre-loaded spring (e.g., wave spring).

With reference to FIGS. 61-66, the drive assembly 1150 of the surgical instrument holder 1102 is configured to transfer a rotation of the drive shaft 1109 of the motor "M" of the surgical instrument holder 1102 into rotational motion of the motor assembly 1114 (FIG. 68) of the instrument drive unit 1110 when the instrument drive unit 1110 is operably received within the surgical instrument holder 1102. The drive assembly 1150 includes a driven shaft 1152 rotatably disposed within the housing 1106. The driven shaft 1152 has a proximal end 1152a, and a distal end 1152b. The proximal end 1152a of the driven shaft 1152 extends proximally through the top plate 1124 of the housing 1106. The distal end 1152b of the driven shaft 1152 extends distally through the base 1130 of the housing 1106. The driven shaft 1152 of the drive assembly 1150 is rotatably retained within the housing 1106.

Figure 61:
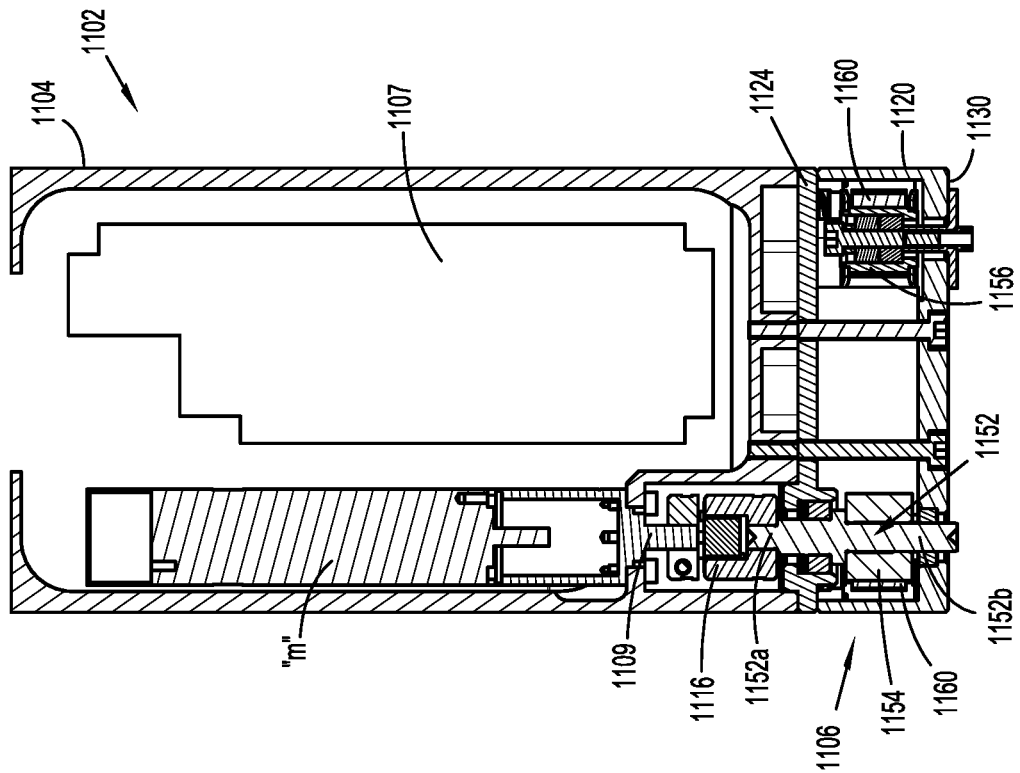
FIG. 61 is a cross-sectional view, taken alone lines 61-61 in FIG. 60B, of the surgical instrument holder.

As illustrated in FIG. 61, the motor "M" of the carriage 1104, the drive shaft 1109 of the carriage 1104, and the driven shaft 1152 of the drive assembly 1150 are each in line with one another. The proximal end 1152a of the driven shaft 1152 is non-rotatably connected to a shaft coupling 1116 of the carriage 1104 such that rotation of the drive shaft 1109 of the motor "M" causes the shaft coupling 1116 to rotate and, in turn, the driven shaft 1152 of the drive assembly 1150 to rotate.

With continued reference to FIGS. 61-66, the drive assembly 1150 includes a first pulley 1154 and a second pulley 1156; each disposed within a space 1142 defined between the arcuate wall 1136 of the housing 1106 and the sidewall 1120 of the housing 1106, and specifically at respective opposing corners 1144a, 1144b of the second portion 1120b of the sidewall 1120. The distal end 1152b of the driven shaft 1152 is non-rotatably connected to the first pulley 1154 such that rotation of the driven shaft 1152 effects rotation of the first pulley 1154 relative to the housing 1106. The first and second pulleys 1154, 1156 may be selectively movable within the housing 1106 to different locations of the housing 1106. The first and second pulleys 1154, 1156 may each be in the form of gears, such as, for example, spur gears having teeth 1158 extending radially from a periphery thereof. In some embodiments, the first and second pulleys 1156 may have smooth outer surfaces without teeth.

The drive assembly 1150 further includes a drive strap or belt 1160 rotatably and/or translatably received within the housing 1106. The belt 1160 is a closed loop and fabricated from a pliable material such that the belt 1160 may be manipulated into any suitable shape. In particular, the belt 1160 takes on the oblong semicircular shape of the housing 1106 upon being received in the housing 1106. In some embodiments, the belt 1160 may be formed from a rigid material and have a permanent oblong semicircular shape corresponding to the shape of the enclosure 1122 of the housing 1106. The belt 1160 may have teeth 1162 extending from an inner surface thereof. The belt 1160 is wrapped around the first and second pulleys 1154, 1156 such that the teeth 1162 of the belt 1160 are in operable engagement with the teeth 1158 of the first and second pulleys 1154, 1156. In this way, rotation of the first pulley 1154 caused by actuation of the motor "M" of the carriage 1104, causes the belt 1160 to rotate around the first and second pulleys 1154, 1156. The second pulley 1156 acts as an idler pulley to guide the belt 1160 around the inner periphery of the sidewall 1120 of the housing 1106. It is contemplated that the second pulley 1156 may be selectively moved to a plurality of positions to effect the tension on/of the belt 1160.

Figure 66B:
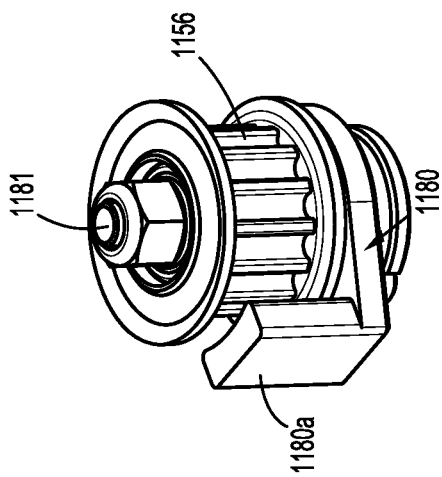
FIG. 66B is a perspective view of the indicated area of detail shown in FIG. 66A.
Figure 66A:
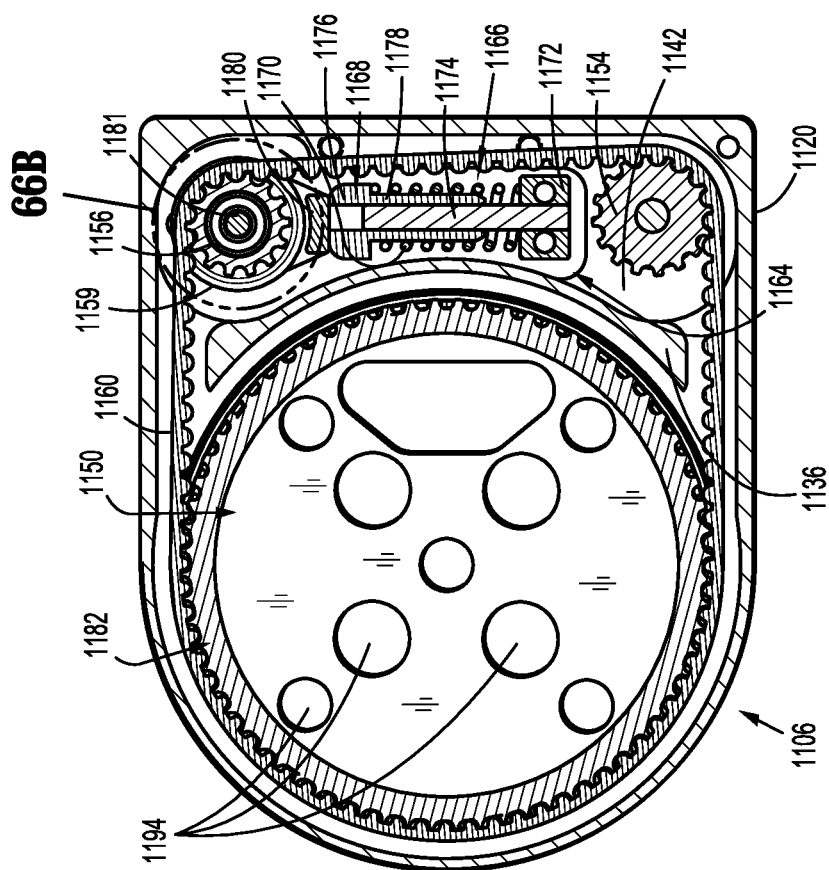
FIG. 66A is a top view of the housing of the surgical instrument holder of FIG. 65B with the addition of a tensioning assembly.

With reference to FIG. 66A, in one embodiment, the drive assembly 150 may include a tensioning assembly 1164 configured to adjust the tension on/of the belt 1160. In particular, the tensioning assembly 1164 may be placed within a space 1142 defined between the arcuate wall 1136 of the housing 1106 and the sidewall 1120 of the housing 1106, and extend between the first and second pulleys 1154, 1156. The tensioning assembly 1164 includes a first shaft assembly 1166, a second shaft assembly 1168, and a coil spring 1170.

The first shaft assembly 1166 is in a fixed position within the housing 1106 and includes a block 1172 disposed adjacent the first pulley 1154, and a shaft 1174 extending from the block 1172 and along an axis intersecting the first and second pulleys 1154, 1156. The second shaft assembly 1168 includes a block 1176 disposed adjacent a pulley sled 1180, and a tubular shaft 1178 extending from the block 1176. With reference to FIG. 66B, the pulley sled 1180 rotatably supports the second pulley 1156 about a shaft 1181 and includes an engagement tab 1180a in contacting relation with the block 1176. The tubular shaft 1178 of the second shaft assembly 1168 has shaft 1174 of the first shaft assembly 1166 extending therethrough and is slidable along the shaft 1174 of the first shaft assembly 1166. The coil spring 1170 is disposed about the tubular shaft 1178 and captured between the blocks 1172, 1176 of respective first and second shaft assemblies 1166, 1168 to resiliently bias the block 1176 of the second shaft assembly 1168 away from the block 1172 of the first shaft assembly 1166. The coil spring 1170 pushes on the block 1176, which pushes on a pulley sled 1180 to bias the second pulley 1156 away from the first pulley 1154 and adjust (e.g., increase) tension in the belt 1160. The pulley sled 1180, and its components, are slidable along the axis defined by the shaft 1174 in response to longitudinal translation of the block 1176 (e.g., to adjust tension in the belt 1160).

To adjust the amount of tension contributed by the tensioning assembly 1164, a plurality of coil springs, each having different spring forces, may be interchanged for the coil spring 1170. Alternately, to adjust the tension in the belt 1160, the tensioning assembly 1164 may be moved to different positions relative to the second pulley 1156.

Figure 62:
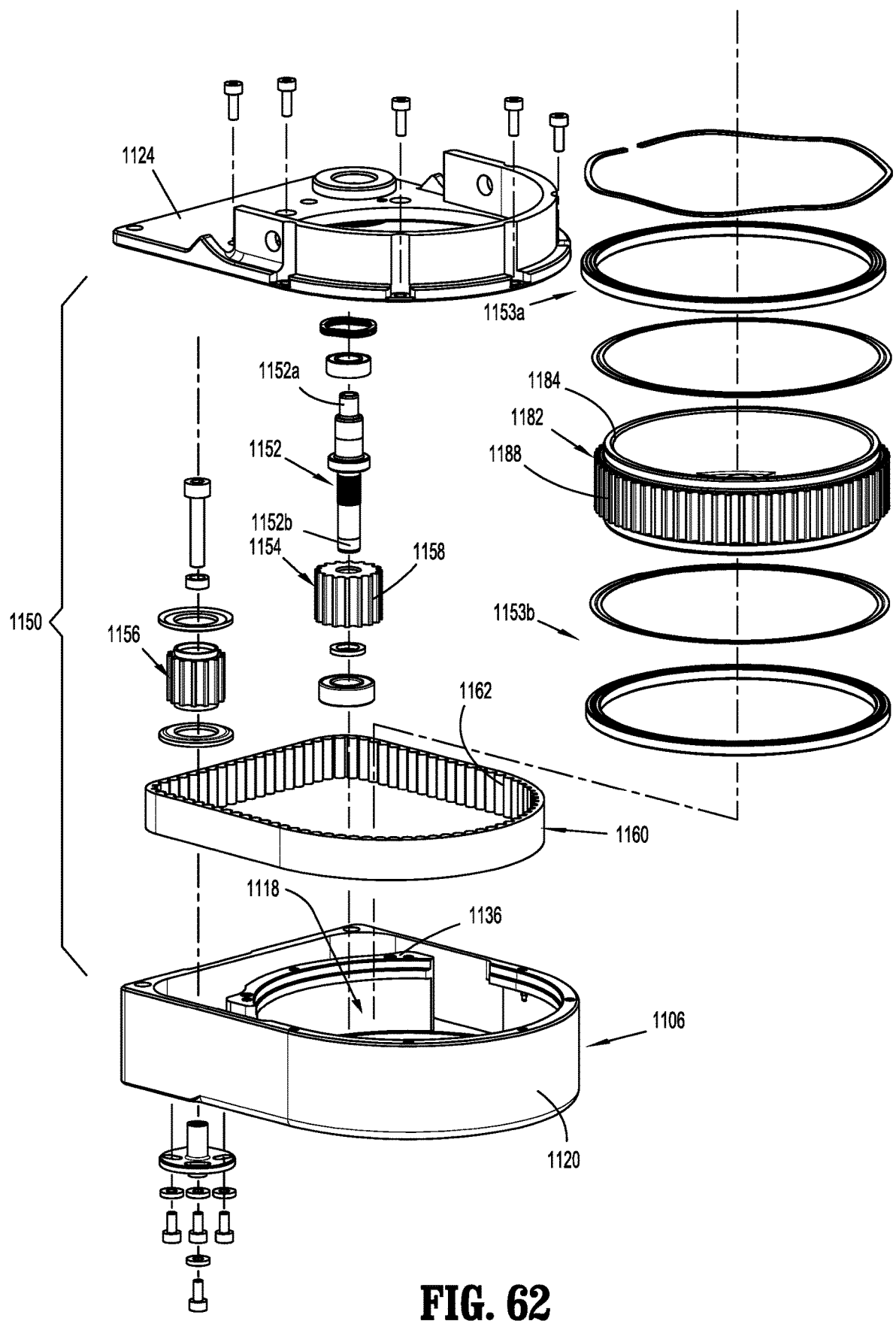
FIG. 62 is a perspective view, with parts separated, of a drive assembly and a housing of the surgical instrument holder of FIG. 60B.
Figure 63:
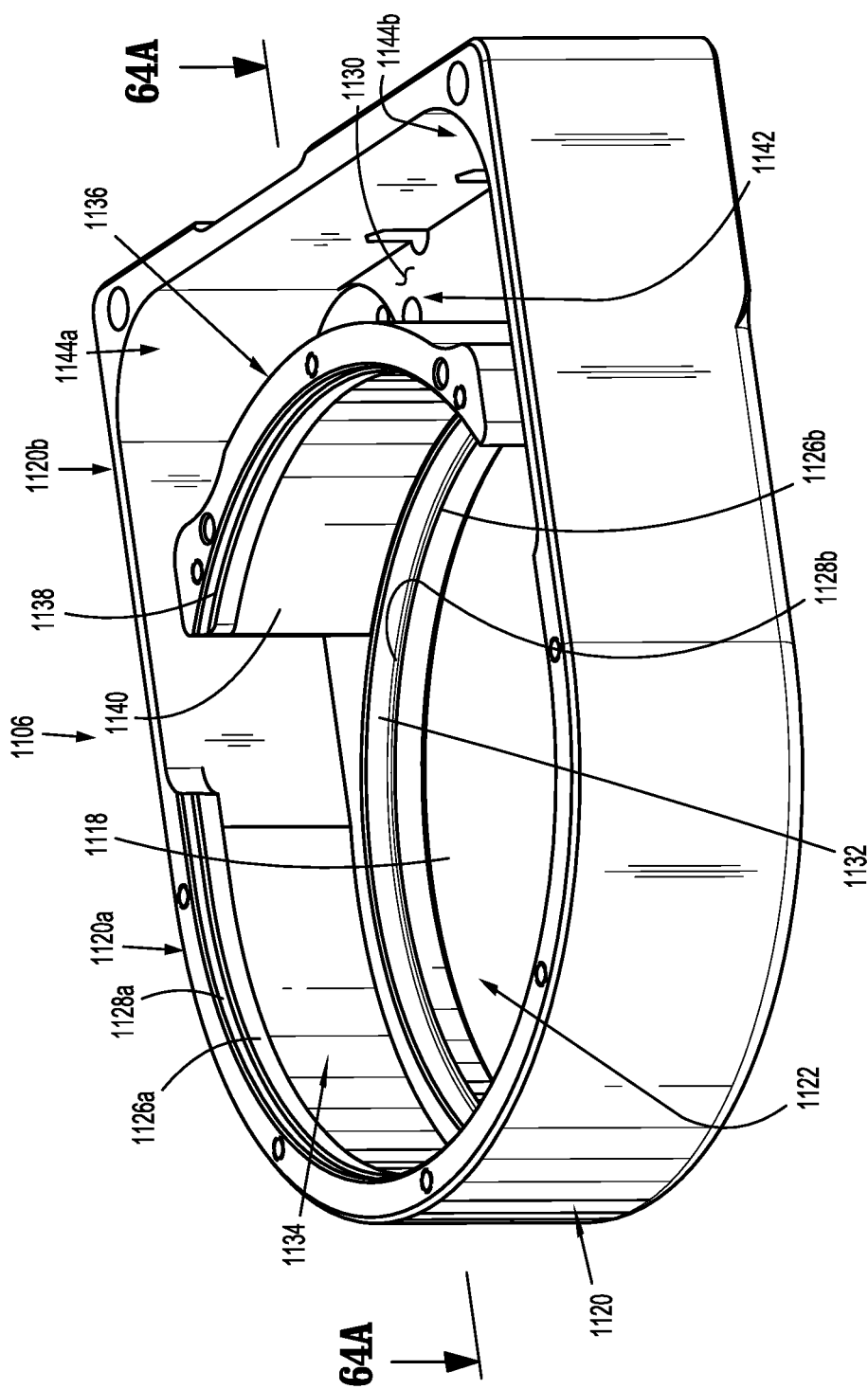
FIG. 63 is an enlarged view of the housing of the surgical instrument holder of FIG. 62.

With continued reference to FIGS. 62, 64B, and 65B, the drive assembly 1150 includes a cup-shaped annular member 1182 rotatably disposed within the channel 1118 of the housing 106 between the first and second bearings 1153a, 1153b of the drive assembly 1150. The annular member 1182 includes a ring 1184, and an annular base plate or disc 1186 disposed within the ring 1184. The ring 184 has a plurality of teeth 1188 extending radially from an outer surface thereof. With the annular member 1182 rotatably seated between the first and second bearings 1153a, 1153b of the drive assembly 1150, the teeth 1188 of the annular member 1182 are in operable engagement with the teeth 1162 of the belt 1160. In this regard, movement of the belt 1160 along the inner periphery of the sidewall 120 of the housing 106 by rotation of the first pulley 154 causes the annular member 1182 to rotate within the channel 1118 of the housing 1106.

In some embodiments, the first pulley 1154 and the belt 1160 do not have teeth for transferring rotational motion between one another. Instead, rotation is transferred between the first pulley 1154 and the belt 1160 via the frictional engagement of a smooth inner surface of the belt 1160 with a smooth outer surface of the first pulley 1154. It is contemplated that each of the components of the drive assembly 1150 may be removable from the housing 1106 to facilitate assembly, repair, and adjustments of the drive assembly 1150.

With reference to FIGS. 64B, 65B, 67, and 68, the annular base plate 1186 of the annular member 1182 and an inner surface 1190 of the ring 1184 of the annular member 1182 cooperatively define a cylindrical cavity 1192 configured for receipt of the instrument drive unit 1110. The annular base plate 1186 defines a plurality of holes 1194 therethrough configured for receipt of various drive shafts (not shown) of the instrument drive unit 1110. With the drive shafts of the instrument drive unit 1110 extending through the holes 1194 of the annular base plate 1186, rotation of the annular member 1182 via belt 1160 results in rotation of the motor assembly 1114 of the instrument drive unit 1110 relative to the housing 1106 of the surgical instrument holder 1102, as will be described in detail below.

To assemble the drive assembly 1150, the belt 1160 is lowered into the housing 1106 to line the inner periphery of the sidewall 1120 of the housing 1106 and extend through the groove 1134 defined between the upper and lower ledges 1128a, 1128b of the housing 106. The first bearing 1153a is pressed onto an upper portion of the annular member 1182 and the second bearing 1153b is pressed onto a lower portion of the annular member 1182. The annular member 1182 with the first and second bearings 1153a, 1153b is lowered into the channel 1118 of the housing 1106 and supported between the upper and lower ledges 1128a, 1128b of the housing 1106. The first and second pulleys 1154, 1156 are installed in opposing corners 1144a, 1144b of the housing 1106 such that the belt 1160 wraps around the first and second pulleys 1154, 1156 and around the annular member 1182. At this stage of assembly, the belt 1160 may be tensioned. The cover plate 1124 is then secured to the top portion of the housing 1106.

Figure 67:
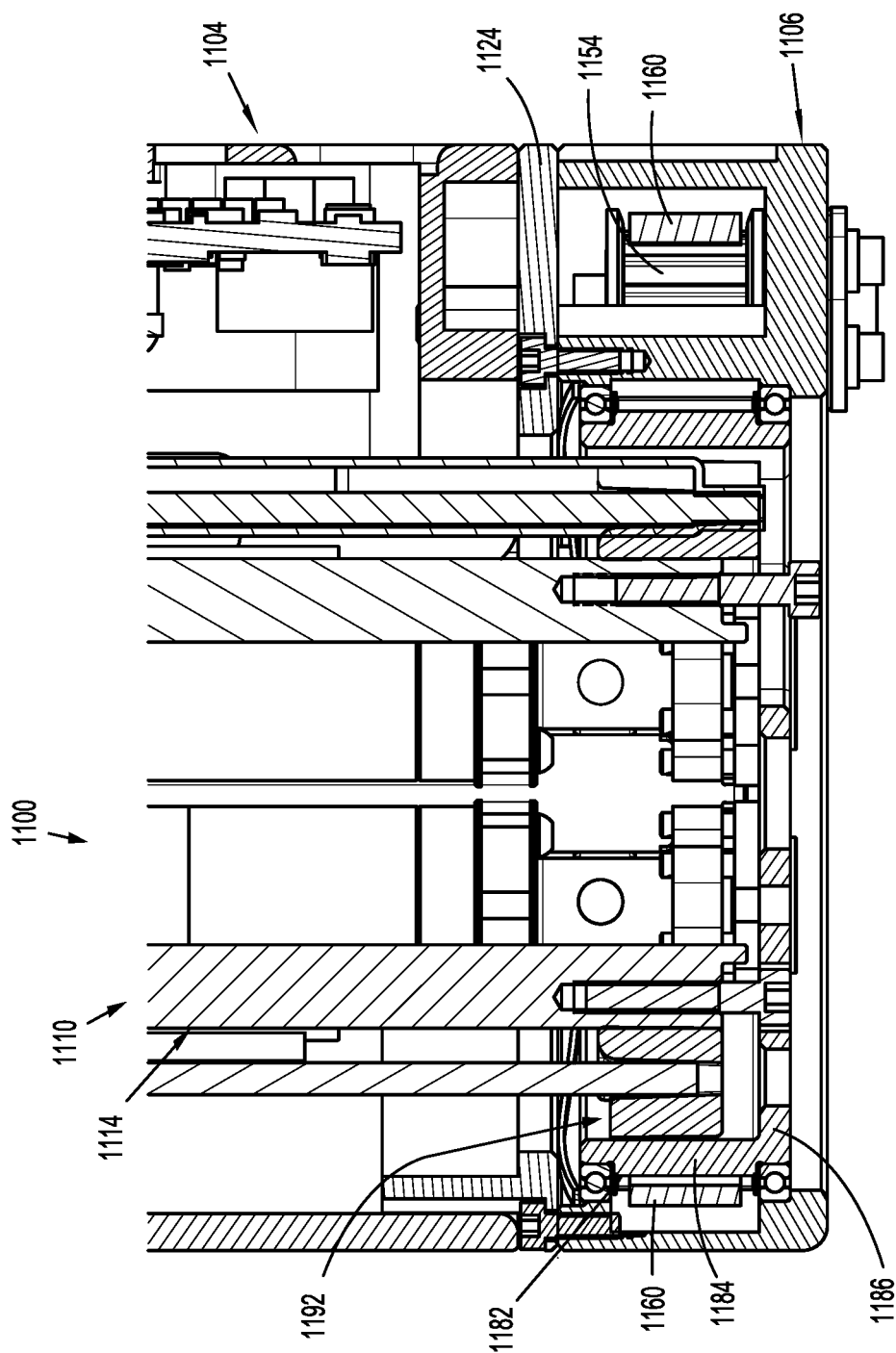
FIG. 67 is a cross-sectional view, taken along lines 67-67 of FIG. 59, of the surgical assembly, illustrating the instrument drive unit disposed in the surgical instrument holder.
Figure 68:
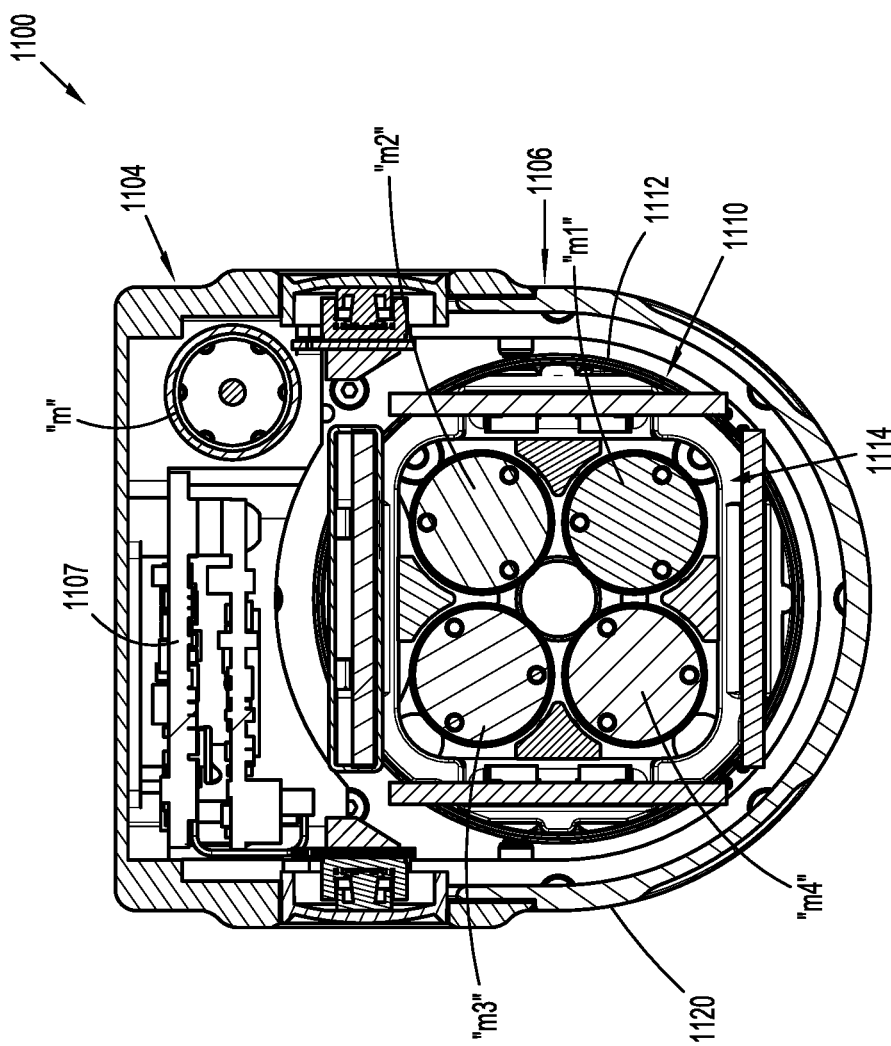
FIG. 68 is another cross-sectional view, taken along lines 68-68 of FIG. 59, of the surgical assembly, illustrating the instrument drive unit disposed in the surgical instrument holder.

With reference to FIGS. 67 and 68, the instrument drive unit 1110 of the surgical assembly 1100 includes an outer housing 1112 and an inner housing or motor assembly 1114 rotatably disposed within the outer housing 1112. The outer housing 1112 is engaged to the second side 1108b of the carriage 1104 of the surgical instrument holder 1102 and houses various components of the instrument drive unit 1110. The outer housing 1112 of the instrument drive unit 1110 has a generally cylindrical configuration, but in some embodiments, the outer housing 1112 may assume a variety of configurations, such as, for example, squared, elongate, tubular, or the like.

The outer housing 1112 of the instrument drive unit 1110 is configured and dimensioned to slidably receive a motor assembly, motor pack or the like 1114 therein. The motor assembly 1114 may include four motors "M1-M4," for example, canister motors or the like, each having a drive shaft (not explicitly shown) having a non-circular transverse cross-sectional profile (e.g., substantially D-shaped, or the like). The four motors are arranged in a rectangular formation such that respective drive shafts thereof are all parallel to one another and all extending in a common direction. As the motors of the motor assembly 1114 are actuated, rotation of the drive shafts of the motors is transferred to gears (not shown) of drive assemblies (not shown) of the surgical instrument 1200 via respective drive transfer shafts (not shown) to actuate various functions of the surgical instrument 1200. In addition, as mentioned above, when the instrument drive unit 1110 is disposed within the annular member 1182 of the drive assembly 1150 of the surgical instrument holder 1102, the drive shafts of each motor of the motor assembly 1114 extend through the holes 1194 of the annular base plate 1186 of the annular member 1182.

In operation, the carriage 1104 of the surgical instrument holder 1102 is attached to the rail 40 of the robotic arm 2. The instrument drive unit 1110 is positioned within the annular member 1182 of the drive assembly 1150 and supported on the side 1108b of the carriage 1104 of the surgical instrument holder 1102 so that the drive shafts (not shown) of the motor assembly 1114 of the instrument drive unit 1110 extend through the respective holes 1194 defined in the annular base plate 1186 of the annular member 1182. The driven shafts (not shown) of the proximal end 1202 (FIG. 59) of the surgical instrument 1200 are non-rotatably connected to the drive shafts of the motor assembly 1114 of the instrument drive unit 1110.

A clinician operating the manual input devices 7, 8 (FIG. 1) of the surgical system may actuate the motor "M" of the surgical instrument holder 1102 to ultimately effect rotation of the surgical instrument 1200 to orient the surgical instrument 1200 in a particular position within a surgical site. In particular, actuation of the motor "M" of the surgical instrument holder 1102 drives rotation of the motor shaft 1109 of the surgical instrument holder 1102, which transfers its rotational motion to the driven shaft 1152 of the drive assembly 150 via the shaft coupling 1116. Rotation of the driven shaft 1152 of the drive assembly 1150 effects rotation of the first pulley 1154 due to the first pulley 1154 being non-rotatably connected to the driven shaft 1152. Since the belt 160 of the drive assembly 1150 is in operable engagement with the first pulley 1154 of the drive assembly 1150, and the annular member 1182 of the drive assembly 1150 is in operable engagement with the belt 1160, rotation of the first pulley 1154 causes the belt 1160 of the drive assembly 1150 to rotate and, in turn, causes the annular member 1182 of the drive assembly 150 to rotate.

With the drive shafts of the motor assembly 1114 of the instrument drive unit 1110 captured in the holes 1194 of the annular base plate 1186 of the annular member 1182 of the drive assembly 1150, rotation of the annular member 1182 of the drive assembly 1150 within the housing 1106 of the surgical instrument holder 1102 drives a rotation of the motor assembly 1114 of the instrument drive unit 1110 relative to the outer shell 1112 of the instrument drive unit 1110. In some embodiments, the motor assembly 1114 of the instrument drive unit 1110 may be non-rotatably received within the annular member 1182 of the drive assembly 1150 via any suitable method, for example, friction fit, non-circular complimentary mating surfaces, or any suitable fastener. In certain embodiments, the motor assembly 1114 is bolted to the annular member 1182. With the proximal end 1202 of the surgical instrument 200 non-rotatably coupled to the motor assembly 1114 of the instrument drive unit 1110, rotation of the motor assembly 1114 of the instrument drive unit 1110 results in rotation of the surgical instrument 200 about its longitudinal axis "X."

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A surgical instrument holder, comprising:
   a carriage configured for engagement with a surgical robotic arm and for supporting an instrument drive unit, the carriage including a motor;
   a housing extending from the carriage and defining a channel; and
   a drive assembly including:
   a pulley rotatably disposed within the housing and in operable engagement with the motor such that actuation of the motor rotates the pulley;
   a belt rotatably disposed within the housing and in operable engagement with the pulley such that rotation of the pulley effects rotation of the belt; and
   an annular member disposed within the channel of the housing and configured for non-rotatable receipt of an instrument drive unit, the annular member in operable engagement with the belt such that rotation of the belt effects rotation of the annular member, wherein the belt is a closed loop and includes teeth extending from an inner surface of the belt, the annular member having teeth extending from an outer surface thereof and in operable engagement with the teeth of the belt.

2. The surgical instrument holder according to claim 1, wherein the annular member includes:
   a ring having the teeth of the annular member extending therefrom; and
   an annular base plate disposed within the ring and defining a plurality of holes therethrough, the ring and the annular base plate cooperatively defining a cavity configured for non-rotatable receipt of an instrument drive unit.

3. The surgical instrument holder according to claim 1, wherein the carriage further includes:
   a rotatable drive shaft extending from the motor; and
   a shaft coupling non-rotatably connected to the drive shaft, wherein the drive assembly further includes a driven shaft having a proximal end non-rotatably connected to the shaft coupling, and a distal end non-rotatably connected to the pulley such that rotation of the drive shaft of the carriage effects rotation of the shaft coupling and in turn rotation of the pulley of the drive assembly.

4. The surgical instrument holder according to claim 3, wherein each of the motor of the carriage, the drive shaft of the carriage, and the driven shaft of the drive assembly are in line with one another.

5. The surgical instrument holder according to claim 1, wherein the carriage further includes a printed circuit board in electrical communication with the motor to control an operation of the motor.

6. The surgical instrument holder according to claim 1, wherein the belt is pliable and configured to travel along an oblong semicircular shape defined by the housing.

7. The surgical instrument holder according to claim 1, wherein the housing includes:
a sidewall defining an enclosure therein;
a base disposed within the enclosure and connected to the sidewall, the base defining the channel of the housing and an arcuate bottom ledge; and
an arcuate wall extending upwardly from the base.

8. The surgical instrument holder according to claim 7, wherein the drive assembly further includes:
a first bearing disposed in the housing, the first bearing being in engagement with the annular member; and
a second bearing disposed on the arcuate bottom ledge of the housing, the second bearing being in engagement with the annular member, wherein the first and second bearings facilitate rotation of the annular member relative to the housing.

9. The surgical instrument holder according to claim 1, wherein the drive assembly further includes another pulley rotatably disposed within the housing and in operable engagement with the belt, the pulleys of the drive assembly being spaced from one another, wherein the belt wraps around the pulleys of the drive assembly and around the annular member.

10. A surgical assembly for use with a surgical robotic arm, comprising:
an instrument drive unit including:
a housing; and
a motor assembly rotatably disposed within the housing; and
a surgical instrument holder including:
a carriage having a first side configured for movable engagement with a surgical robotic arm, and a second side configured for non-rotatably supporting the housing of the instrument drive unit, the carriage including a motor and a printed circuit board in electrical communication with the motor of the carriage to control an operation of the motor of the carriage;
a housing extending from the carriage and defining a channel; and
a drive assembly including:
a pulley rotatably disposed within the housing of the surgical instrument holder and in operable engagement with the motor of the carriage such that actuation of the motor of the carriage rotates the pulley of the drive assembly;
a belt rotatably disposed within the housing and in operable engagement with the pulley such that rotation of the pulley effects rotation of the belt; and
an annular member disposed within the channel of the housing and configured for non-rotatable receipt of the motor assembly of the instrument drive unit, the annular member in operable engagement with the belt such that rotation of the belt causes the annular member to rotate resulting in rotation of the motor assembly of the instrument drive unit relative to the housing of the instrument drive unit.

11. The surgical assembly according to claim 10, wherein the belt is a closed loop and has teeth extending from an inner surface thereof, the annular member having teeth extending from an outer surface thereof and in operable engagement with the teeth of the belt.

12. The surgical assembly according to claim 11, wherein the annular member includes:
a ring having the teeth of the annular member extending therefrom; and
an annular base plate disposed within the ring and defining a plurality of holes that receive drive shafts of the motor assembly therethrough, the ring and the annular base plate cooperatively defining a cavity configured to receive the motor assembly of the instrument drive unit.

13. The surgical assembly according to claim 10, wherein the carriage further includes:
a rotatable drive shaft extending from the motor; and
a shaft coupling non-rotatably connected to the drive shaft, wherein the drive assembly further includes a driven shaft having a proximal end non-rotatably connected to the shaft coupling, and a distal end non-rotatably connected to the pulley such that rotation of the drive shaft of the carriage effects rotation of the shaft coupling and in turn rotation of the pulley of the drive assembly.

14. The surgical assembly according to claim 13, wherein each of the motor of the carriage, the drive shaft of the carriage, and the driven shaft of the drive assembly are in line with one another.

15. The surgical assembly according to claim 10, wherein the belt is pliable and configured to travel along an oblong semicircular shape defined by the housing of the surgical instrument holder.

16. The surgical assembly according to claim 10, wherein the housing of the surgical instrument holder includes:
a sidewall defining an enclosure therein;
a base disposed within the enclosure and connected to the sidewall, the base defining the channel of the housing and an arcuate bottom ledge; and
an arcuate wall extending upwardly from the base.

17. The surgical assembly according to claim 16, wherein the drive assembly further includes:
a first bearing disposed in the housing, the first bearing being in engagement with the annular member; and
a second bearing disposed on the arcuate bottom ledge of the housing, the second bearing being in engagement with the annular member, wherein the first and second bearings facilitate rotation of the annular member relative to the housing.

18. The surgical assembly according to claim 10, wherein the drive assembly further includes another pulley rotatably disposed within the housing, the another pulley being in operable engagement with the belt, the pulleys of the drive assembly being spaced from one another, wherein the belt wraps around the pulleys of the drive assembly and around the annular member.

19. The surgical assembly according to claim 10, further comprising a surgical instrument configured for non-rotatable connection with the motor assembly of the instrument drive unit such that rotation of the motor assembly of the instrument drive unit via the drive assembly of the surgical instrument holder effects rotation of the surgical instrument.

20. A surgical instrument holder, comprising:
- a carriage configured for engagement with a surgical robotic arm and for supporting an instrument drive unit, the carriage including:
  - a motor;
  - a rotatable drive shaft extending from the motor; and
  - a shaft coupling non-rotatably connected to the drive shaft;
- a housing extending from the carriage and defining a channel; and
- a drive assembly including:
  - a pulley rotatably disposed within the housing and in operable engagement with the motor such that actuation of the motor rotates the pulley;
  - a belt rotatably disposed within the housing and in operable engagement with the pulley such that rotation of the pulley effects rotation of the belt;
  - an annular member disposed within the channel of the housing and configured for non-rotatable receipt of an instrument drive unit, the annular member in operable engagement with the belt such that rotation of the belt effects rotation of the annular member; and
  - a driven shaft having a proximal end non-rotatably connected to the shaft coupling, and a distal end non-rotatably connected to the pulley such that rotation of the drive shaft of the carriage effects rotation of the shaft coupling and in turn rotation of the pulley of the drive assembly.

21. The surgical instrument holder according to claim 20, wherein the annular member includes:
- a ring; and
- an annular base plate disposed within the ring and defining a plurality of holes through the annular base plate, the ring and the annular base plate cooperatively defining a cavity configured for non-rotatable receipt of an instrument drive unit.

* * * * *